US005962477A

United States Patent [19]
Mak

[11] Patent Number: 5,962,477
[45] Date of Patent: Oct. 5, 1999

[54] SCREENING METHODS FOR CYTOKINE INHIBITORS

[75] Inventor: Vivian Mak, Menlo Park, Calif.

[73] Assignee: Adolor Corporation, Malvern, Pa.

[21] Appl. No.: 09/097,441

[22] Filed: Jun. 15, 1998

Related U.S. Application Data

[63] Continuation-in-part of application No. PCT/US95/04677, Apr. 11, 1995, which is a continuation-in-part of application No. 08/400,234, Mar. 3, 1995, abandoned, which is a continuation-in-part of application No. 08/271,287, Jul. 6, 1994, abandoned, which is a continuation-in-part of application No. 08/225,991, Apr. 12, 1994, abandoned.

[51] Int. Cl.$^6$ .............................................. A61K 31/445
[52] U.S. Cl. .......................... 514/327; 424/78.05
[58] Field of Search .................... 514/327; 424/78.05

[56] References Cited

U.S. PATENT DOCUMENTS

| | | | |
|---|---|---|---|
| 3,275,510 | 9/1966 | Magid et al. | 167/58 |
| 3,714,159 | 1/1973 | Adriaan et al. | 260/247.1 |
| 3,789,072 | 1/1974 | Bernstein | 260/557 B |
| 3,884,916 | 5/1975 | Janssen et al. | 260/247.7 |
| 3,914,238 | 10/1975 | Soudijn et al. | 260/293.58 |
| 3,950,537 | 4/1976 | DeBenneville et al. | 424/322 |
| 3,996,214 | 12/1976 | Dajani et al. | 260/240 |
| 3,998,832 | 12/1976 | Adelstein et al. | 260/293.54 |
| 4,012,374 | 3/1977 | Wade et al. | 260/239.3 |
| 4,012,393 | 3/1977 | Markos et al. | 260/293.54 |
| 4,013,668 | 3/1977 | Adelstein et al. | 260/293.54 |
| 4,025,652 | 5/1977 | Diamond et al. | 424/322 |
| 4,057,549 | 11/1977 | Adelstein et al. | 260/293.54 |
| 4,060,635 | 11/1977 | Diamond et al. | 424/322 |
| 4,066,654 | 1/1978 | Adelstein et al. | 260/293.69 |
| 4,069,223 | 1/1978 | Adelstein et al. | 260/293.76 |
| 4,072,686 | 2/1978 | Adelkstein et al. | 260/293.69 |
| 4,115,564 | 9/1978 | Diamond et al. | 424/244 |
| 4,116,963 | 9/1978 | Adelstein et al. | 260/293.69 |
| 4,125,531 | 11/1978 | Yen | 546/133 |
| 4,194,045 | 3/1980 | Adelstein | 546/209 |
| 4,203,920 | 5/1980 | Diamond et al. | 260/553 A |
| 4,218,454 | 8/1980 | DeGraw et al. | 424/260 |
| 4,238,390 | 12/1980 | Meienhofer et al. | 260/112.5 |
| 4,269,843 | 5/1981 | DeGraw et al. | 424/260 |
| 4,277,605 | 7/1981 | Buyniski et al. | 546/74 |
| 4,326,074 | 4/1982 | Diamond et al. | 564/47 |
| 4,326,075 | 4/1982 | Diamond et al. | 564/48 |
| 4,328,803 | 5/1982 | Pape | 128/276 |
| 4,371,463 | 2/1983 | Pert et al. | 260/112.5 E |
| 4,384,000 | 5/1983 | Lanier | 424/267 |
| 4,407,794 | 10/1983 | Roques et al. | 424/177 |
| 4,416,886 | 11/1983 | Bernstein | 424/260 |
| 4,430,327 | 2/1984 | Frederickson | 424/177 |
| 4,493,848 | 1/1985 | LaHann et al. | 424/324 |
| 4,517,295 | 5/1985 | Bracke et al. | 435/101 |
| 4,533,739 | 8/1985 | Pitzele et al. | 548/559 |
| 4,626,539 | 12/1986 | Aungst et al. | 514/282 |
| 4,749,706 | 6/1988 | Lawson et al. | 514/282 |
| 4,824,853 | 4/1989 | Wals et al. | 514/327 |
| 4,870,084 | 9/1989 | Eggler et al. | 514/320 |
| 4,871,750 | 10/1989 | Roberts | 514/328 |
| 4,892,735 | 1/1990 | Harrap | 424/435 |
| 4,897,260 | 1/1990 | Ros et al. | 424/59 |
| 4,898,873 | 2/1990 | Wals et al. | 514/327 |
| 4,917,896 | 4/1990 | Peck et al. | 424/449 |
| 4,990,521 | 2/1991 | Van Daele et al. | 514/327 |
| 5,039,642 | 8/1991 | Chrobaczek | 502/155 |
| 5,069,909 | 12/1991 | Sharma et al. | 424/449 |
| 5,100,903 | 3/1992 | Lalinde et al. | 514/327 |
| 5,109,135 | 4/1992 | D'Ambra et al. | 544/73 |
| 5,112,596 | 5/1992 | Malfroy-Camine | 424/2 |
| 5,116,847 | 5/1992 | Gilbert et al. | 514/327 |
| 5,116,868 | 5/1992 | Chen et al. | 514/546 |
| 5,143,938 | 9/1992 | Calvet et al. | 514/653 |
| 5,149,538 | 9/1992 | Granger et al. | 424/449 |
| 5,202,130 | 4/1993 | Grant et al. | 424/617 |
| 5,214,080 | 5/1993 | Iwamura et al. | 523/336 |
| 5,229,127 | 7/1993 | McKinzie | 424/427 |
| 5,236,947 | 8/1993 | Calvet et al. | 514/433 |
| 5,240,932 | 8/1993 | Morimoto et al. | 514/282 |
| 5,242,944 | 9/1993 | Park et al. | 514/466 |
| 5,248,505 | 9/1993 | Garwin | 424/472 |
| 5,273,056 | 12/1993 | McLaughlin et al. | 128/898 |
| 5,273,751 | 12/1993 | Dubroff | 424/427 |
| 5,278,126 | 1/1994 | Katano et al. | 503/201 |
| 5,282,851 | 2/1994 | Jacob-LaBarre | 623/6 |
| 5,286,751 | 2/1994 | Sunshine et al. | 514/570 |
| 5,292,362 | 3/1994 | Bass et al. | 106/124 |
| 5,300,648 | 4/1994 | Emonds-Alt et al. | 546/193 |
| 5,312,899 | 5/1994 | Schiller | 530/331 |
| 5,345,943 | 9/1994 | Hargreaves et al. | 128/742 |
| 5,354,863 | 10/1994 | Dappen et al. | 546/35 |

(List continued on next page.)

FOREIGN PATENT DOCUMENTS

| | | |
|---|---|---|
| 0127154 | 5/1984 | European Pat. Off. . |
| 0350221 | 6/1989 | European Pat. Off. . |
| 0544391 | 8/1992 | European Pat. Off. . |
| 0582727 | 8/1992 | European Pat. Off. . |
| 2100711 | 5/1971 | France . |
| 9213540 | 8/1992 | WIPO . |
| 9527510 | 10/1995 | WIPO . |
| 9709973 | 3/1997 | WIPO . |
| 9732857 | 9/1997 | WIPO . |
| 9733634 | 9/1997 | WIPO . |
| 9827985 | 7/1998 | WIPO . |
| 9842275 | 10/1998 | WIPO . |

OTHER PUBLICATIONS

Abbott, "Peripheral and central antinociceptive actions of ethylketocyclazocine in the formalin test." *Eur. J. Pharmacol.* 142:93–100 (1988).

(List continued on next page.)

*Primary Examiner*—Cecilia J. Tsang
*Attorney, Agent, or Firm*—Stephanie L. Seidman; Heller Ehrman White & McAuliffe

[57] ABSTRACT

The present invention provides a number of screening methods for evaluatiing compounds capable of suppressing cytokine production either in vitro or in vivo. The methods generally involve stimulating the production of a cytokine in a cell, exposing a portion of the cells to a putative cytokine modulating agent and determining subsequent levels of cytokine production in the cells. Additionally, the present invention provides certain compounds identified by this method.

5 Claims, 3 Drawing Sheets

U.S. PATENT DOCUMENTS

| | | | |
|---|---|---|---|
| 5,366,979 | 11/1994 | Lawson | 514/282 |
| 5,369,131 | 11/1994 | Poli et al. | 514/772.4 |
| 5,384,124 | 1/1995 | Courteille et al. | 424/430 |
| 5,387,688 | 2/1995 | Feldman et al. | 546/223 |
| 5,403,867 | 4/1995 | Okumura et al. | 514/573 |
| 5,432,176 | 7/1995 | Walser | 514/252 |
| 5,434,292 | 7/1995 | Saita et al. | 560/51 |
| 5,436,009 | 7/1995 | Jauw et al. | 424/436 |
| 5,437,994 | 8/1995 | Emerson et al. | 435/240.2 |
| 5,446,070 | 8/1995 | Mantelle | 514/772.6 |
| 5,460,821 | 10/1995 | Masiz | 424/449 |
| 5,478,814 | 12/1995 | Packman | 514/53 |
| 5,589,480 | 12/1996 | Elkhoury et al. | 514/282 |
| 5,618,557 | 4/1997 | Wille et al. | 424/449 |
| 5,645,854 | 7/1997 | Masiz | 424/449 |
| 5,646,151 | 7/1997 | Kruse et al. | 514/255 |
| 5,667,773 | 9/1997 | Farrar et al. | 424/78.05 |
| 5,686,106 | 11/1997 | Kelm et al. | 424/463 |
| 5,688,955 | 11/1997 | Kruse et al. | 546/276.4 |
| 5,744,458 | 4/1998 | Kruse et al. | 514/91 |
| 5,760,023 | 6/1998 | Farrar et al. | 514/150 |
| 5,763,445 | 6/1998 | Kruse et al. | 514/255 |
| 5,798,093 | 8/1998 | Farrar et al. | 424/45 |
| 5,811,078 | 9/1998 | Maycock et al. | 424/45 |
| 5,849,761 | 12/1998 | Yaksh | 514/327 |
| 5,849,762 | 12/1998 | Farrar et al. | 514/327 |

OTHER PUBLICATIONS

Adelstein, Gilbert W., et al., "3,3–Diphenyl–3–(2–alkyl–1, 3,4–oxadiazol–5–yl)propylcycloalkylamines, a Novel Series of Antidiarrheal Agents," *Journal of Medicinal Chemistry*, 19:1221–1225 (1976).

Alreja, et al., The formalin test: A tonic pain model in the primate, *Pain*, 20:97–105 (1984).

Andreev et al., "Opoids suppress spontaneous activity of polymodal nociceptors in rat paw skin induced by ultraviolet radiation." *Neuroscience* 58(4):793–798 (1994).

Ansel et al., "Cytokine modulation of keratinocyte cytokines", *J. of Inv. Derm.* 94(6):101–107 (1990).

Antonijevic, et al., Perineurial defect and peripheral opioid analgesia in inflammation, *J. Neurosci.*, 15(1):165–172 (1995).

Awouters et al., "Loperamide: Survey of studies on mechanism of its antidiarrheal activity." *Digestive Diseases and Sciences* 38(6):977–995 (1993).

Awouters et al., "Pharmacology of antidiarrheal drugs." *Ann. Rev. Pharmacol. Toxicol.* 23:279–301 (1983).

Berrebi et al., "Varapamil inhibits B–cell–proliferation and tumor necrosis factor release and induces a clinical response in B–cell chronic lymphocytic leukemia", *Leukemia* 8(12):2214–2216 (1994).

Bianchi and Goi, "On the antidiarrheal and analgesic properties of diphenoxylate difenoxine and loperamide in mice and rats." *Arzeneimittel–Forschung/Drug Research* 27(1),5, 1040–1043 (1977).

Buerkle et al., "Comparison of the spinal actions of the $\mu$–opioid remifentanil with alfentanil and morphine in the rat", *Anesthesiology* 84(1):94–102 (1996).

Burkhardt et al., "Metkephamid (Tyr–D–Ala–Gly–Phe–N–(Me)Met–NH$_2$), a potent opoid peptide: Receptor binding and analgesic properties." *Peptides* 3:869–871 (1982).

Chemical Abstr. 121:57079d (1994), citing Park et al., "Synthesis of caspicinoids: 3–nitrogen–substituted phenylacetamides", *Korean J. Med. Chem.* 3(2): 142–147 (1993).

Chemical Abstr. 96:20297n (1982), citing Belgian Patent BE 886,579 (Jun. 10, 1981).

Chemical Abstr. 100:17470j (1984), citing Iizuka et al., "Pharmacodynamics of a new antidiarrheic nufenoxole", *Jitchuken Zenrinsho Kenkyho* 9(1): 19–41 (1983).

Chemical Abstr. 82:156117x (1975), citing Ger. Offen. DE 2,440,541 (Mar. 6, 1975).

Chemical Abstr. 120:289632m (1994), citing Park et al., Pain reducing effects of 4–amino and 4–(1–piperazinyl) phenylacetamide derivatives, *Korean J. Med. Chem.* 3(2): 116–23 (1993).

Chemical Abstr. 105:208764w (1986), citing Ger. Offen. DE 3,545,981 (Jan. 7, 1985).

Chemical Abstr. 120:116860f (1994), citing Japanese patent JP 05,286,851 (Nov. 2, 1993).

Cortes, et al., Tape stripping–induced hyperalgesia as a model for the evaluation of analgesic agents, *Soc. Neurosci. Abstr.*, 22:1315 (1996).

D'Amour et al., "A method for determining loss of pain sensation." *J. Pharmacol. Exp. Ther.* 72:74 (1941).

Dashwood et al., "Autoradiographic demonstration of [$^3$H] loperamide binding to opioid receptors in rat and human small intestine." *The International Narcotics Research Conference (INRC) '89*, Alan R. Liss, Inc., pp. 165–169 (1990).

DeHaven–Hydkins et al., ADL 2–1294, a peripherally selective opiate analgesic, *Society for Neuroscience Abstracts* 22 (1–3): 1362 (1996).

Database, Derwent Publication 199236, citing patent # 9213540, Analgesic ointment contg. cocaine or novacaine—together with menthol and salicylate ester.

Dubuisson, et al., The formalin test: A quantitative study of the analgesic effects of morphine, meperidine, and brain stem stimulation in rats and cats, *Pain*, 4:161–174 (1977).

Enk et al., "Early molecular events in the induction phase of contact sensitivity", *Proc. Natl. Acad. Sci USA* 89:1398–1402 (1992).

Ferreira et al., "Prostaglandin hyperalgesia: The peripheral analgesic activity of morphine, enkephalins and opioid antagonists." *Prostaglandins* 73:191–200 (1979).

Frederickson et al., "Metkephamid, a systemically active analogue of methionine enkephalin with potent opoid $\sigma$–receptor activity." *Science* 211:603–605 (1981).

Frederickson, "Animal and human analgesic studies of metkaphamid." *Advances in Pain Research and Therapy, vol. 8*, Foley and Inturrsi, Eds., Raven Press, New York pp. 293–301 (1986).

Gasbarrini, G., et al., "Multicenter Double–blind Controlled Trial Comparing idamidine HC1 and Loperamide in the Symptomatic Treatment Acute Diarrhoea," *Drug Res.* 36:1843–1845.

Giagnoni et al., "Loperamide: Evidence of interaction with $\mu$ and $\sigma$ opid receptors." *Life Sci.* 33(Suppl. 1):315–318 (1983).

Goodman et al., *The pharmacological basis for therapeutics*, McMillian, New York, NY, pp. 505–517 (1985).

Gottschlich et al., "The peripherally acting $\kappa$–opiate agonist EMD 61753 and analogues: opioid activity versus peripheral selectivity", *Drugs Exptl. Clin. Res.* XXI(5):171–174 (1995).

Handwerker et al., "Pain and Inflammation." *Proceedings of the VIth World Congress on Pain, Chapter 7*, Bond, et al., Eds., Elsevier Science Publishers BV, Amsterdam, pp. 59–70 (1991).

Heykants, et al., Loperamide (R 18 553), a novel type of antidiarrheal agent, *Arzneim.–Forsch. Drug Res.*, 24:1649–1653 (1974).

Hurwitz, A., et al., "Lopermide effects on hepatobiliary function, intestinal transit and analgesia in mice," *Life Sciences*, 54:1687–1698, (1994).

Jaffe et al., "Abuse potential of loperamide." *Clin. Pharmacol. Ther.* 28(6):812–819 (1980).

Lee, Buyean, et al., "KR–25018: A Novel, Orally Active Analgesic with Non–narcotic Properties," *Arch. Pharm. Res.*, 17:5:304–308, (1994).

Levine et al., "Involvement of the mu–opiate receptor in peripheral analgesia", *Neuroscience* 32(3):571–575 (989).

Mackerer et al., Loperamide binding to opiate receptor sites of brain and myenteric plexus. *J. Pharmacol. Exp. Ther.* 199:131–140 (1976).

Mackerer et al., Review of the involvement of opiate receptors in producing the central and peripheral effects caused by two new antidiarrheal drugs, loperamide and SC–27166. *J. Am. Coll. Toxicol.* 3:81–91 (1984).

Mackerer et al., Antidiarrheal and central nervous system activities of SC–27166 (2–[3–5–methyl–1,3, 4–oxadiazol–2–YL)–3,3–Diphenylpropyl]–2–Azabicyclo [2.2.2]Octane), A new antidiarheal agent, resulting from binding to opiate receptor sites of brain and myenteric plexus, *J. Pharmac. and Exp. Ther.* 203(3):527–538 (1977).

Megans et al., Is in vivo disassociation between the antipropulsive and antidiarrheal properties of opioids in rats related to gut selectivity? *Arch. Int. Pharmacodyn. Ther.* 298:220–229 (1989).

Megans et al., Normalization of small intestinal propulsion with loperamide–like antidiarrheals in rats. *Eur. J. Pharmacol.* 178:357–364 (1990).

Mir, G.N., et al., "In vivo Anitmotility and Antidiarheal Activity of Lipamidine Hydrochloride (WHR–1142A), a Novel Antidiarrheal Agent," *Drug Res.*, 28:II), 1448–1480).

Molina et al., "The peripheral analgesic effect of morphine, codeine, pentazocine and D–propoxyphene", *Brazilian J. Med. Biol. Res.* 16:345–352 (1983).

Nagasaka et al., Peripheral and spinal actions of opioids in the blockade of the autonomic response evoked by compression of the inflamed knee joint. *Anesthesiol.* 85:808–816 (1996).

Niemegeers et al., Dissociation between opiate–like and antidiarrheal activities of antidiarrheal drugs. *J. Pharmacol. Exp. Ther.* 203:527–538 (1979).

Niemegeers et al., "Loperamide (R 18 553), a novel type of antidiarrheal agent", *Arzneim.–Forsch.* (Drug Res.) 24(10):1633–1641 (1974).

Oluyomi, et al., Differential antinociceptive effects of morphine and methylmorphine in the formalin test, *Pain*, 49:415–418 (1992).

Osborne, Richard, et al., "Analgesic Activity of Morphine–6–Glucuronide," *The Lancet*, :828, (1988).

Park, No–Sang, et al., "KR–25003, a Potent Analgesic Capsaicinoid," *Acta Crystallographica* C51:927–929 (1995).

Randall et al., "A method for measurement of analgesic activity on inflamed tissue." *Arch. Int. Pharmacodyn.* 111(4):409–419 (1957).

Reinstein et al., "Suppression of lipopolysaccharide–stimulated releae of tumor necrosis factor by adenosine: evidence of $A_2$ receptors on rat kupffer cells".

Rogers, et al., GR94839, a κ–opioid agonist with limited access to the central nervous system, has antinociceptive activity, *J. Pharmacol.*, 106:783–789 (1992).

Russell et al., "Opiates inhibit the discharges of fine afferent units from imflamed knee joint of the cat." *Neurosci. Lttrs.* 76:107–112 (1987).

Schafer, et al., Inflammation enhances peripheral μ–opioid receptor–mediated analgesia, but not μ–opioid receptor transcription in dorsal root ganglia, *Eur. J. Pharmacol.*, 279:165–169 (1995).

Schinkel, et al., P–Glycogprotein in the blood–brain barrier of mice influences the brain penetration and pharmacological activity of many drugs, *Br. J. Clin. Invest.*, 97:2517–2524 (1996).

Shaw, John S., "ICI 204448: aκ–opioid agonist with limited access to the CNS," *Br. J. Pharmacol.* 96:986–992, (1989).

Shriver et al., "Loperamide." *Pharmacological and Biochemical Properties of Drug Substances*, vol. 3, Goldberg, Ed., American Pharmaceutical Ass'n Press pp. 461–476 (1981).

Smith et al., "Peripheral antinociceptive effects of N–methyl morphine", *Life Sciences* 31(12 & 13):1205–1208 (1982).

Stahl et al., "Receptor affinity and pharmacological potency of a series of narcotic analgesic, anti–diarrheal and neuroleptic drugs." *Eur. J. Pharmacol.* 46:199–205 (1977).

Stein, et al., Unilateral inflammation of the hindpaw in rats as a model of prolonged noxious stimulation: Alterations in behavior and nociceptive thresholds, *Pharmacol. Biochem. Behav.*, 31:445–451 (1988).

Stein, "Peripheral mechanisms of opoid analgesia." *Anesth. Analg.* 76:182–191 (1993).

Stein et al., "Analgesic effect of intraarticular morphine after arthroscopic knee surger." *New Eng. J. Med.* 325(16):1123–1126 (1991).

Stein et al., "Peripheral opioid receptors mediating antinociception in inflammation. Evidence for involvement of Mu, Delta and Kappa receptors." *J. Pharmacol. Exp. Ther.* 248(3):1269–1275 (1989).

Stein, et al., Peripheral effect of fentanyl upon nociception in inflamed tissue of the rat, *Neurosci. Lett.*, 84:225–228 (1988).

Stein, "Peripheral analgesic actions of opioids", *J. Pain and Sympt Mgmt.* 6(3):119124 (1991).

Stein, "Peripheral opioid receptors", *Ann Med* 27:219–221 (1995).

Stokbroekx et al., "Synthetic antidiarrheal agents. 2,2–Diphenyl–4–(–'–aryl–4'–hydroxypiperid ino) butyramides", *J. Med. Chem.* 16(7):782–786 (1973).

Takasuna et al., "Opoid pharmacology of the antinociceptive effects of loperamide in mice." *Behav. Pharmacol.* 5:189–195 (1994).

Thompson et al., "Local analgesia with opioid drugs", *Ann Pharm* 29:189–190 (1995).

Tjolsen, et al., The formalin test: an evaluation of the method, *Pain*, 51:5–17 (1992).

Van der Kooy, Hyperalgesic functions of peripheral opiate receptors. *Ann. N.Y. Acad. Sci.* 467:154–168 (1986).

van Joost et al., "Cyclosporine in atopic dermatitis", *J. Amer Acad of Derm.* 27(6):922–928 (1992).

Wheeler–Aceto et al., Characterization of nociception and edema after formalin–induced tissue injury in the rat: Pharmacological analysis of opioid activity, *UMI Dissertaion Services* pp. 321–336; 398–406, (1995).

Williams et al., "CD28–stimulated IL–2 gene expression in Jurkat T cells occurs in part transcriptionally and is cyclosporine–A sensitive[1]", *J. of Immun.* 148:2609–2616 (1992).

Wuster, Michael, et al., "Opiate Agonist Action of Antidiarrheal Agents in vitro and in vivo—Findings in Support for Selective Action," *Archives of Pharmacology*, 301:187–194, (1978).

Yaksh et al., "Sites of action of opiates in production of analgesia." In, *Progress in Brain Research*, vol. 77, Chap. 28, Elsevier Science Pub., B.V., pp. 371–394 (1988).

Yaksh, "Multiple opioid receptor systems in brain and spinal cord: Part I." *Eur. J. Anaesthesiol.* 1:171–199 (1984).

Yaksh, "The spinal actions of opoids." *Handbook of Experimental Pharmacology*, vol. 104/II Opoids II, Chapter 33, Herz, Ed., Springer–Verlag, Berlin and Heidelberg, pp. 53–90 (1993).

SCREENING METHODS FOR CYTOKINE INHIBITORS

This application is a continuation-in-part of PCT Appln. Serial No. PCT/US95/04677, filed Apr. 11, 1995, which is a continuation-in-part of Ser. No. 08/400,234, filed Mar. 3, 1995, now abandoned which is a continuation-in-part of Ser. No. 08/271,287, filed Jul. 6, 1994, now abandoned which is a continuation-in-part of Ser. No. 08/225,991, filed Apr. 12, 1994, now abandoned the full disclosures of which are incorporated herein by reference.

FIELD OF THE INVENTION

The present invention relates to the field of inflammation and immunology. More particularly, the present invention provides screening methods for the identification of agents which are capable of suppressing cytokine production. Additionally, the present invention provides compositions which are useful as medicaments in the treatment of a variety of acute and chronic, systemic or skin conditions having an inflammatory and/or immunological component.

BACKGROUND OF THE INVENTION

Inflammation represents a cascade of physiological and immunological reactions that nature has designed as the first cellular response to noxious stimuli in an effort to localize toxic materials or prevent tissue injury. Clinically, inflammation is a primary disease under acute conditions or is a manifestation of underlying pathophysiological abnormalities in chronic disease, characterized by classic signs of redness, pain, swelling and loss of function. Inflammatory diseases are a significant cause of morbidity and mortality in humans.

Regardless of the etiology, most forms of inflammation are propagated as a result of the recruitment of humoral and cellular components of the immune system. Current research indicates that a class of proteins known as cytokines, products of immune-competent cells including macrophages, T-lymphocytes, endothelial cells, etc., are crucial in the initiation and maintenance of inflammation. Cytokines are small- to medium-sized (usually less than 30 kDa), hormone-like proteins governing numerous biological responses such as cell growth, cell maturation, and defense against infection. The major cytokines include interferons (IFNs), colony stimulating factors (CSFs), interleukins (ILs), and tumor necrosis factors (TNF and lymphotoxin). Due to their unique biological and extremely potent pharmacological properties, several cytokines have also been considered as therapeutic agents since their discovery in the 1950s. The importance of cytokines biologically and as potential therapeutic agents is well-recognized by the medical and pharmaceutical communities.

With respect to inflammation, TNF, IL-1 and IL-8 have all been characterized as proinflammatory cytokines. The release of these cytokines triggers a cascade of multiple cellular and molecular events including the expression of adhesion molecules, i.e. intercellular adhesion molecule-1 (ICAM-1), E-selectin, etc., the production of secondary inflammatory mediators (prostaglandins, leukotrienes), and growth factors (transforming growth factor alpha, TGF-α). Under acute inflammatory conditions (e.g., endotoxemia), it is well known that TNF is one of the earliest mediators produced, appearing earlier than IL-1 or other cytokines (see, Michalek, et al., *J. Inf. Dis.* 141:55–63 (1980); Freudenberg, et al., *Inf. Immun.* 51:891–895 (1986); Beutler, et al., *J. Immunol.* 135:3972–3977 (1985) and Fong, et al., *J. Exp. Med.* 170:1627–1633 (1989)). Furthermore, administration of TNF to animals reproduces the pathologic effects of endotoxin (see Tracey, et al., *Surg. Gyn. Obstet.* 164:415–422 (1987) and Tracey, et al., *Science* 234:470–474 (1986)). In other correlative studies, the level of TNF observed is a predictive indicator of the outcome in endotoxin shock (see Waage, et al., *Lancet* (1)8529:355–357 (1987)). There are significant overlaps between the current understanding of the pathophysiology leading to the development of acute skin disorders and acute systemic inflammatory conditions like endotoxemia. In both scenarios, TNF production by hematopoietic cells is the primary event which initiates and orchestrates the inflammatory cascade.

In chronic inflammatory conditions, elevated tissue levels of several mediators including the cytokines IL-1, IL-8, GM-CSF, and TNF have been found in the inflamed joints of patients with rheumatoid arthritis (RA) (see Yocum, et al., *Cellular Immunol.* 122:131–145 (1989) and Hopkins, et al., *Clin. Exp. Immunol.* 73:88–92 (1988)). With synovial culture systems, it was demonstrated that TNF regulated the production of GM-CSF and IL-1 in addition to expression of more TNF receptors making TNF seminal in this disease pathogenesis. Similarly, there is an increased level of TNF in the intestinal mucosa (Olson, et al., *J. Pediatric Gastroenterology and Nutrition* 16:241–246 (1993)) and in the feces (Nicholls, et al., *J. Clin. Pathol.* 46:757–760 (1993)) in patients with inflammatory bowel diseases (IBD, includes Crohn's disease and ulcerative colitis). While it is generally recognized that chronic inflammation is a complex cellular and molecular event, it has been suggested that cytokine mediators do not act in parallel, but in series. This view has been verified recently by clinical results demonstrating a clear resolution of both severe RA (Elliott, et al., *Arthritis and Rheumatism* 36:1681–1690 (1993)) and IBD upon administration of anti-TNF antibody. Thus, TNF is found to be the key mediator in these two diseases and, in various other inflammatory conditions including psoriasis, asthma, cancer, infection, and cachexia associated with AIDS and cancer.

In principle, the inflammatory response can be regulated through the use of drugs. Unfortunately, anti-inflammatory drugs presently available produce cytotoxic effects which reflect their initial employment as cancer chemotherapeutics, typically anti-neoplastics. Such drugs effectively kill cells indiscriminately. Corticosteroids are also mainstay anti-inflammatory agents but manifest significant adverse effects, such as inducing Cushingoid features, skin thinning, increased susceptibility to infection, and suppression of the hypothalamic-pituitary-adrenal axis. The use of other immunosuppressive agents such as cyclosporin A also may induce the development of severe side effects, e.g., hypertension and nephrotoxicity.

What is needed in the art are new and more effective methods of treating inflammation which specifically target TNF production and which carry fewer significant and undesirable side effects. Methods which suppress TNF production will find application not only in inflammation of the skin, but also in systemic inflammation. Surprisingly, the present invention provides such methods of suppressing TNF production and treating inflammation.

SUMMARY OF THE INVENTION

Figure 1:
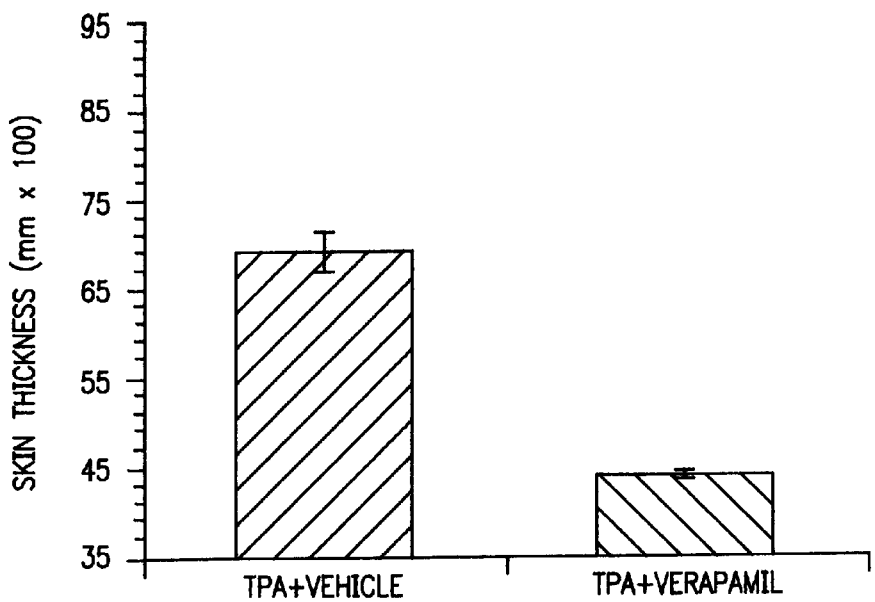
FIG. 1 illustrates the ability of verapamil to suppress inflammation in TPA-treated mouse skin.

The present invention provides screening assays to identify new immune modulating agents, compounds which are effective immune modulating agents and compositions and methods for modulating the inflammatory response.

In one embodiment, the present invention provides a method of screening for skin immune or inflammation modulating agents. In this method, keratinocytes are stimulated to produce at least one cytokine or MHC Class II molecule. A portion of the keratinocytes are then exposed to a putative skin inflammation modulating agent, and a determination is made as to whether the putative agent is effective to modulate the production of the cytokine or MHC Class II molecule in the exposed keratinocytes as opposed to keratinocytes not exposed to the agent.

In a preferred embodiment, the determination is performed by measuring the amount of mRNA corresponding to the cytokine or MHC Class II molecule produced by the keratinocytes. In another preferred embodiment, the amount of cytokine produced or MHC Class II molecule is measured directly. In yet another preferred embodiment, the frequency of transcription of a gene encoding the cytokine or MHC Class II molecule is measured.

The present invention further provides methods of treating a pathological condition mediated by TNF production in a mammal by administering a therapeutically effective amount of a potassium sparing diuretic, antidiarrheal, cyclic AMP modulating agent or a calcium channel blocker to the mammal. Preferred diuretics and antidiarrheals are spironolactone, furosemide, loperamide and diphenoxylate. The calcium channel blocker is preferably a benzoacetonitrile, a dihydropyridine or a benzothiazepinone. More preferably the calcium channel blocker will be administered as a specific optical isomer for those compounds having at least one optical center. The selection of the optical isomer for use in the present invention is such that an optimal modulation of TNF production is achieved. In particularly preferred embodiments, the calcium channel blocker is verapamil, nicardipine or isradipine. In a further preferred embodiment, the calcium channel blocker is verapamil, predominantly as its plus isomer.

In another group of embodiments, the pathological condition which is mediated by TNF production is a systemic inflammatory condition, preferably inflammatory bowel disease, rheumatoid arthritis, cachexia, asthma, Crohn's disease, endotoxin shock, adult respiratory distress syndrome, ischemic/reperfusion damage, graft-versus-host reactions, bone resorption, transplantation or lupus.

In still another group of embodiments, the pathological condition which is mediated by TNF production is multiple sclerosis, diabetes or AIDS.

In one group of embodiments, the pathological condition which is mediated by TNF production is a skin inflammatory condition, preferably psoriasis, atopic dermatitis, UV-induced inflammation, contact dermatitis or inflammation induced by other drugs, including, but not limited to Retin-A.

In yet another embodiment, the present invention includes methods of modulating skin inflammatory response wherein an anti-inflammatory preparation is applied to the skin.

In still another embodiment, the present invention includes methods for treating a non-allergic skin inflammatory condition in a mammal, wherein a TNF inhibitor is administered to a mammal displaying symptoms of such a condition and thereafter the state of the mammal's symptoms is determined.

The present invention also includes methods of modulating and treating inflammatory responses in the skin in which an electric field effective to modulate the production of cytokines in the skin is applied to the skin. In another embodiment, the electric field is applied to the skin in conjunction with a skin inflammation modulating (suppressing or inducing) drug.

The present invention also provides methods for reducing skin adverse reactions, sensitization and irritation associated with the application of a transdermal or iontophoretic delivery device, and/or other drugs to the skin.

Still further, the present invention provides methods for the treatment of ocular inflammation using TNF inhibitors and methods for the treatment of skin sensitization or irritation associated with the use of a cosmetic or skin care product.

DETAILED DESCRIPTION OF THE INVENTION

Table of Contents

I. Definitions
II. The TNF-Mediated Response in Various Diseases
III. Embodiments of the Invention
   A. Screening Assays
     1. In Vitro Assays
       a. Direct Measurement of Cytokine Production
         (1) ELISA
         (2) Radioimmunoassay
         (3) Gel Electrophoresis and Western Blotting
         (4) Immunohistochemistry
         (5) Bioassays
       b. Measurement of Cytokine Gene Expression
         (1) Northern Blotting
         (2) In situ Hybridization
         (3) RT-PCR
         (4) Ribonuclease Protection Assay
         (5) Nuclear Run-On Assay
       c. Transcription of Cytokines
       d. Measurement of MHC Class II Production
         (1) Direct Measurement of MHC Class II Protein Expression
         (2) Measurement of MHC Class II Gene Expression
     2. In Vivo Models
   B. Methods For Modulation of the Inflammatory/Immune or TNF-Mediated Response
     1. Chemical Methods
       a. TNF Inhibitors
         (1) Isomers of Calcium Channel Blockers
       b. Neuropeptide and Neurotransmitter Antagonists
       c. Antihistamines
       d. Immunosuppressants
       e. Other Pharmacological Agents
       f. Formulations and Delivery
         (1) Topical Formulations
         (2) Oral Formulations
         (3) Aerosol Formulations (4) Solutions
(5) Transdermal Patches
(6) Occlusion
(7) Iontophoresis
(8) Sonophoresis
(9) Combinations
g. Dosages and Schedules
2. Occlusion
3. Application of an Electric Field
4. Sonophoresis
5. Combinations
IV. Therapeutic Regimens
A. The Treatment of Sensitization, Inflammation, and Irritation Accompanying Transdermal Drug Delivery
B. The Treatment of Skin Diseases
C. The Treatment of Skin Cancers
D. The Treatment of Wounds
E. The Treatment of Ocular Inflammation
F. The Treatment of Inflammation Asssociated With Cosmetic and Skin Care Products
G. The Treatment of Systemic Inflammatory Conditions
V. Examples
A. Animal Models
B. Determination of Ion Concentrations
C. Determination of Cytokine Levels
D. Induction of Transepidermal Water Loss
E. Inhibition of Proinflammatory Cytokine Production In Keratinocytes
F. Diagnosis and Evaluation
G. The Treatment of Skin Inflammatory Diseases with a Solution of Ions using Iontophoresis
H. The Reduction of Irritation in Conjunction with Topical Drug Administration
I. Treatment of Superficial Wounds and External Cancers
J. Topical Formulations
K. Topical Skin Delivery of Verapamil Formulations
L. Prevention or Reduction of Transdermal Drug Delivery System-induced Irritation
M. Use of Specific Isomers of Calcium Channel Blockers to Modulate TNF-Mediated Conditions
1. Inhibition of TNF Release in Stimulated Cells
2. Verapamil for the Prevention of Skin Inflammation in Mice
3. Verapamil for the Treatment of Skin Inflammation in Humans
4. (+)-Verapamil for the Treatment of Atopic Dermatitis
5. (+)-Verapamil in a Topical Formulation to Treat Psoriasis
6. (+)-Verapamil for the Treatment and Prevention of UV-Induced Inflammation
7. (+)-Verapamil in Combination with Retin-A for the Treatment of Dermatitis
8. (+)-Verapamil for the Treatment of Rheumatoid Arthritis
9. (+)-Verapamil As A Second Active Agent in a Transdermal Patch
10. (+)-Verapamil for the Treatment of Inflammatory Bowel Diseases
11. (+)-Verapamil for the Treatment of Cachexia I. Definitions Unless otherwise stated, the following terms used in the specification and claims have the meanings given below:

The term "optical center" or "chiral center" refers to a center, usually a carbon atom, which has four distinct and different substituents such that chirality can be specified according to the Cahn-Ingold-Prelog system. In this system, each optical center can be defined as having an R- or an S-configuration. Accordingly, molecules which have at least one optical center are termed "chiral molecules." A molecule is chiral if no stable conformation can be superimposed on its mirror image. A molecule having at least one optical center can therefore exist as a racemic pair of enantiomers, each enantiomer rotating polarized light in equivalent but opposite direction. Each of these enantiomers can be termed (+)- or (−)—depending upon whether polarized light is rotated in a clockwise or counter-clockwise direction, respectively. A racemic mixture, often termed a (±)-mixture, can be separated into its "optical isomers," namely the (+)-isomer and the (−)-isomer. Equivalent terms for the (+)-isomer and the (−)-isomer are dextrorotatory (d) and levorotatory (l), respectively. For example, the term "plus isomer" of verapamil means the dextrorotatory form of the two enantiomeric molecules. Equivalent terms are: plus verapamil, (+)-verapamil, (R)-verapamil and positive verapamil. Additionally, the use of any of these terms is meant to include both the compound in its free base form and those forms which include a pharmaceutically acceptable salt.

The terms "preferentially", "predominantly", "substantially" and the like, when referring to one isomer of a racemic pair, mean that precautions or steps have been taken to ensure that the one isomer occurs in a greater percentage compared to the percentage which would occur in the conventionally prepared racemic mixture. The individuals and entities who would take such a step include, but are not limited to, the manufacturer, supplier, pharmacist, and clinician or other practitioner. For example, the term "predominantly (+)-verapamil" or an equivalent phrase means that the plus-verapamil is at least 70%, more preferably at least 80%, and most preferably at least 95% of the verapamil under discussion.

The terms "treatment", "therapy" and the like refer to changes in the recipient's status. The changes can be either subjective or objective and can relate to features such as symptoms or signs of the disease or condition being treated. For example, if the patient notes decreased itching or decreased pain, then successful treatment has occurred. Similarly, if the clinician notes objective changes, such as by histological analysis of a biopsy sample, then treatment has also been successful. Alternatively, the clinician may note a decrease in inflammatory lesions or other abnormities upon examination of the patient. This would also represent an improvement or a successful treatment. Prevention of deterioration of the recipient's status is also included by the term. Therapeutic benefit includes any of a number of subjective or objective factors indicating a response of the condition being treated as discussed herein.

"Healthy skin" or "normal skin" refers to non-lesional skin, i.e., with no visually obvious erythema, edema, hyper-, hypo-, or uneven pigmentations, scale formation, xerosis, or blister formation. Histologically, healthy or normal skin refers to skin tissue with a morphological appearance comprising well-organized basal, spinous, and granular layers, and a coherent multi-layered stratum corneum. In addition, the normal or healthy epidermis comprises a terminally differentiated, stratified squamous epithelium with an undulating junction with the underlying dermal tissue. Normal or healthy skin further contains no signs of fluid retention, cellular infiltration, hyper- or hypoproliferation of any cell types, mast cell degranulation, parakeratoses, etc., and implies normal dendritic processes for Langerhans cells and dermal dendrocytes. This appearance is documented in dermatological textbooks, for example, HISTOPATHOLOGY OF THE SKIN, Lever and Schaumburg-Lever (eds.), J. B. Lippincott Company (1991) and TEXTBOOK OF DERMATOLOGY, Champion et al. (eds.), 5th Ed. Blackwell Scientific Publications (1992), especially Chapter 3 "Anatomy and Organization of Human Skin"; PHYSIOLOGY, BIOCHEMISTRY AND MOLECULAR BIOLOGY OF THE SKIN, VOLS. I AND II, Goldsmith (ed.), Oxford Press (1991), the full disclosures of which are expressly and completely incorporated herein by reference.

"Drug", "pharmacological agent", "pharmaceutical agent", "active agent", and "agent" are used interchangeably and are intended to have their broadest interpretation as to any therapeutically active substance which is delivered to a living organism to produce a desired, usually beneficial effect. In general, this includes therapeutic agents in all of the major therapeutic areas, also including proteins, peptides, oligonucleotides, and carbohydrates as well as inorganic ions, such as calcium ion, lanthanum ion, potassium ion, magnesium ion, phosphate ion, and chloride ion.

"Cytokine" refers to a class of non-antibody proteins released by one cell population on contact with either non-specific stimulus and/or a specific stimulus, for example, an antigen, or a fragment of such a protein which has substantially the same biological activity as the whole protein. Cytokines act as mediators in either autocrine, paracrine, or intracrine fashion, as in the generation of an inflammatory or immune response.

The term "TNF inhibitor," "TNF antagonists" and the like, refers to agents which reduce the production of TNF in any TNF producing cells, including, but not limited to macrophages, monocytes, keratinocytes, neutrophils, mast cells, endothelial cells, activated lymphocytes, NK cells, LAK cells, astrocytes, smooth muscle cells, and other epithelial cell types. Agents in this category demonstrate at least 25% inhibition of TNF production/release at 100 $\mu$M concentration, preferably at 10 $\mu$M, more preferably at 1 $\mu$M, and most preferably at less than 1 $\mu$M concentration. Additionally, preferred agents will demonstrate at least 25% inhibition in more than one cell type at the above concentrations. More preferably, agents will demonstrate at least 25% TNF inhibition in the major cell type involved in the target tissue, for example, epidermal keratinocytes in the inflamed skin. Even more preferred are those agents which provide greater than 40% TNF inhibition, and the most preferred agents provide at least 65% TNF inhibition in all relevant cells types associated with a particular pathological condition.

"Pharmaceutically- or therapeutically-acceptable" refers to a substance which does not interfere with the effectiveness or the biological activity of the active ingredients and which is not toxic to the hosts, which may be either humans or animals, to which it is administered.

"Therapeutically-effective amount" refers to the amount of an active agent sufficient to induce a desired biological result. That result may be alleviation of the signs, symptoms, or causes of a disease, or any other desired alteration of a biological system.

"Non-allergic Skin Inflammatory Condition" refers to an inflammatory condition of the skin which is not solely mediated by a specific antigen. Such conditions include, e.g., irritant contact dermatitis, psoriasis, eczema, pruritus, seborrheic dermatitis, nummular dermatitis, lichen planus, acne vulgaris, comedones, polymorphs, nodulokystic acne, conglobata, senile acne, secondary acne such as solar acne, medicinal acne or professional acne; other types of keratinization disorders, for example, ichthyoses, ichthyosiform conditions, Darier malady, palmoplantary keratodermies, leucoplasies and leucoplasiform conditions and lichen; other dermatologic disorders such as blistery dermatoses and collagen maladies; and extrinsic ageing of the skin, be it photoinduced or not.

"Non-allergic Systemic Inflammatory Condition" refers to an inflammatory condition which is not related to the skin and not mediated solely by a specific antigen. Such conditions include, e.g., inflammatory bowel disease, sepsis, lupus, arthritis, chronic bronchitis, osteoporosis, infection, adult respiratory distress syndrome, and transplantation.

"Allergen" refers herein to a substance which induces symptoms of immediate hypersensitivity by inducing IgE antibody responses and delayed hypersensitivity reaction. Generally, such responses require a sensitization of the immune system to the allergen.

"TNF-mediated conditions" refers to local and systemic physiological disorders where TNF is a primary mediator leading to the manifestation of the disorders. Such conditions includes cachexia (wasting syndrome) in animals and humans afflicted by cancers and various infectious disease, endotoxin shock, acute and chronic inflammatory conditions such as rheumatoid arthritis, inflammatory bowel disease, Crohn's disease, psoriasis, contact dermatitis, adult respiratory distress syndrome, infections, ischemic/reperfusion damage, diseases involving eosinophils (e.g. asthma, allergy, etc.), graft-versus-host reactions, and bone resorption (Beutler B., TUMOR NECROSIS FACTORS, THE MOLECULES AND THEIR EMERGING ROLE IN MEDICINE Raven Press, 1992, and *European Cytokine Network*, 5(2) (1994).

"MHC Class II proteins" or "MHC Class II molecules" refers to transmembrane proteins which bind peptides derived from exogenous antigens in their extracellular domains and are responsible for presenting these immunogenic peptides to class II-restricted T cells. The T cell receptors on the surfaces of the T cells can only recognize and bind to the antigenic peptides on the antigen presenting cell when the peptides are associated with the appropriate class II proteins. In humans, these T cells are CD4 cells. Human MHC Class II proteins include the HLA-DP, -DQ, and -DR variants. These are encoded by polymorphic genes located within the HLA complex on chromosome 6 and are each composed of 2 noncovalently associated polypeptides, $\alpha$ and $\beta$.

Class II proteins are expressed on the surface of only a few cell types, i.e., B cells, macrophages, keratinocytes and dendritic cells, the latter being found in all surface epithelia and include epidermal Langerhans cells. These cell types are also referred to as antigen presenting cells. The dendritic cells express abundant class II and are highly efficient in capturing and presenting antigens and are particularly important in initiating responses against antigens that contact the body surface. When an immunogen is applied to the skin, some Langerhans cells migrate from the site into dermal lymphatics and are carried to the lymph nodes where they present the processed antigens to T cells. In macrophages, the level of class II expression is increased when the macrophage is activated.

The murine class II system is highly analogous to the human situation. Thus, for the purposes of experimentation using animal models, such as rabbits, and, in particular, mouse models, the same general principles and approaches described herein can be applied.

II. The TNF-Mediated Response In Various Diseases

This section includes a discussion of certain factors and events which form a theoretical basis for the embodiments of the invention described herein. However, this discussion is not in any way to be considered as binding or limiting on the present invention. Those of skill in the art will understand that the various embodiments of the invention may be practiced regardless of the model used to describe the theoretical underpinnings of the invention.

TNF, previously known as cachectin, is produced by a large number of cells or tissues including neutrophils, activated lymphocytes, macrophages, NK cells, LAK cells, astrocytes, endothelial cells, smooth muscle cells, mast cells, keratinocytes and other epithelial cell types. This particular cytokine governs a wide variety of biological activities including: cytotoxic effects against tumors, activation of neutrophils, normal proliferation of cells, inflammatory, immunological, and antiviral responses. A membrane-bound form of TNF has been located in lymphocytes or monocytes where it is involved in intracellular signaling and activation.

The specific overproduction of TNF is known to be an important determinant for a number of diseases, infections, and inflammatory conditions including rheumatoid arthritis, cachexia, endotoxin shock, inflammatory bowel disease, Crohn's disease, psoriasis, contact dermatitis, adult respiratory distress syndrome, infections, transplantation, ischemic/reperfusion damage, diseases involving eosinophils (e.g. asthma, allergy, etc.), graft-versus-host reactions, bone resorption, inflammatory bowel disease, multiple sclerosis (MS), diabetes, AIDS and Alzheimer's disease and/or the weight loss associated with Alzheimer patients.

In arthritis, for example, TNF levels correlate with the synovial fluid white blood cell count and with the erythrocyte sedimentation rate (see, Saxne, et al., *Arthritis Rheum.* 31:1041–1045 (1988)). More recent studies in man have shown that anti-TNF antibodies can significantly improve the clinical manifestations of this disease. Patients with active arthritis were treated with chimeric human/mouse monoclonal anti-TNF (see, Elliott, et al., *Arthritis Rheum.* 36:1681–1690 (1993)). After several weeks, significant improvements were seen in the Ritchie Articular Index, the swollen joint count, and in other clinical assessments with corresponding decreases in IL-6 and C-reactive protein.

Multiple sclerosis (MS) is another chronic, inflammatory disease which affects the central nervous system (CNS). Higher levels of TNF are detected in the cerebral spinal fluid of patients with active MS than those with inactive MS (see, Hauser, et al., *Neurology* 40:1735–1739(1990)). In one study, increased TNF and interferon production by monocytes was observed just prior to exacerbation of the disease (see, Beck, et al., *Acta Neurol. Scand.* 78:318–323 (1988)). Further, an anti-TNF monoclonal antibody was successfully used to treat allergic encephalomyelitis (AE) where AE and MS share many characteristics (see, Ruddle, et al., *J. Exp. Med.* 172:1193–1200 (1990)). The incidence, severity and onset of AE in the treated mice all were dramatically reduced.

Insulin resistance is a primary characteristic of non-insulin dependent diabetes mellitus (NDDM). Recently, the induction of TNF mRNA expression was observed in fat tissue using different rodent models of diabetes. Correspondingly, reduction of circulating TNF in obese rats caused a significant increase of the peripheral uptake of glucose. Others demonstrated that TNF directly interferes with the signaling mechanism of insulin through its receptor (see, Hotamisligi, et al., *Proc. Natl. Acad. Sci., USA* 91:4854–4858 (1993)).

TNF and its receptors were measured in serum of HIV-positive patients and from two control groups (see, Aukrust, et al., *J. Infect. Dis.* 169:420–424 (1994)). All HIV-infected patients had significantly elevated levels of the two types of soluble TNF receptors and TNF, which both correlated with reduced CD4+ lymphocytes. The higher amounts of TNF and its receptors indicate activation of the TNF system during HIV infection. Thalidomide, a selective inhibitor of TNF synthesis, suppressed the activation of latent HIV in a monocyte cell line (see, Makonkaweyoon, et al., *Proc. Natl. Acad. Sci., USA* 90:5974–5978 (1993)), and reduced the induction of TNF protein and mRNA. Thalidomide was further demonstrated to inhibit the activation of the virus in monocytes from patients having advanced HIV infection or AIDS.

Another study with homogenized brain tissue correlated the expression of TNF mRNA with cognitive impairment and other related changes in HIV-infected patients (see, Glass, et al., *Neurology* 43:2230–2237 (1993)). Levels of mRNA were significantly greater in patients with HIV-associated dementia than in AIDS patients without dementia, or in seronegative controls. Pentoxifylline (PTX), a drug which blocks TNF release, was tested in HIV-positive patients alone and together with zidovudine (ZDV). The average HIV viral load was increased over baseline after treatment with PIX and ZDV, compared to higher levels in patients given either agent alone (see, Luke, et al., *Int. J. Clin. Pharmacol. Ther. Toxicol.* 31:343–350 (1993)). TNF levels were also correlated with the viral load in patients who had received both drugs.

Chronic inflammatory bowel diseases such as Crohn's disease and ulcerative colitis are of unknown origin yet show an increased production of TNF, IL-1, and IL-6 (see, Braegger, et al., *Ann. Allergy* 72:135–141 (1994)). An increased density of TNF immunoreactive cells in tissue specimens was found with both ulcerative colitis and Crohn's disease suggesting that TNF production probably contributes significantly to the pathogenesis of both Crohn's disease and ulcerative colitis by impairing the epithelial and endothelial membranes or by increasing inflammatory cell infiltration.

As noted above, the largest organ in the body, the skin, also makes TNF. Since skin represents the border to a hostile environment, it needs an arsenal of biological weapons to combat such insults as chemical irritants, bacteria, sunlight and physical trauma. Pro-inflammatory cytokines stand as ready messengers to inform and direct the immune system upon challenge. If these biological weapons become misguided and, in a sense, run astray due to a breakdown in the normal control mechanisms, then disease ensues. Psoriasis is one example of a serious and socially debilitating inflammatory skin disease characterized by a breakdown in the control of proinflammatory cytokines. Other inflammatory skin disorders such as eczema, atopic dermatitis, acne, contact dermatoses, sunburn and even cancers manifest a similar loss of control of the mechanisms that regulate normal cytokine levels in the skin.

Psoriasis is a relatively common skin disease that is thought to be genetically predisposed. This intractable condition is characterized by inflammation and accelerated growth of the epidermis, which results in dull red, scaly plaques that are clearly demarcated from the surrounding uninvolved areas. Abundant scientific and clinical evidence indicates a strong link between the pathogenesis of psoriasis and the localized production of cytokines, and the involvement of TNF is strongly implicated. First, elevated levels of immunoreactive TNF and its receptors have been demonstrated in lesional psoriatic skin by immunohistochemical staining. Further, increased TNF mRNA levels in biopsies and elevated TNF biological activities in suction blister exudates from lesional psoriatic skin have been recently reported. Various clinical studies have demonstrated increased circulating levels of TNF in patients with severe psoriasis, and a decline in circulating TNF levels as drug treatment reduced the lesional severity. In addition, many of the pathophysiological characteristics of psoriasis can be best explained by the presence of local elevated concentrations of TNF. Thus, TNF is one of the most critical cytokines orchestrating the chronic inflammation underlying psoriasis.

Eczema is a generalized term for a dermatitis in which the causative agents are poorly defined. Eczema presents clinically as lesions of variable size not clearly defined from the surrounding normal skin and which are characterized by itching, redness, and scaling. Atopic dermatitis (AD) is a chronically-relapsing form of eczema which appears to be inherited along with other atopic diseases such as asthma. Similarly to eczema, the inflammatory processes involved in the pathogenesis of AD have not been determined although it is usually associated with abnormalities of the immune system. Elevated serum IgE levels have long been considered one of the hallmark features of the disease. Yet, when clinical improvements of AD were observed in patients treated with either cyclosporin A or IFN-γ therapy, a concomitant reduction of serum IgE levels was not seen. Meanwhile, a more recent study of children with AD indicated that circulating TNF levels were increased relative to those of normal children. Elevated IL-8 levels were also found in 41 out of 52 patients suffering from AD where plasma IL-8 levels appear to correlate with the severity of the disease. Since IL-8 is an inducible product of TNF and elevated plasma TNF levels have been found in patients with severe AD, there is strong support that TNF may be involved with initiation and propagation of the chronic inflammatory condition associated with AD.

Allergic contact dermatitis (ACD) is often difficult to distinguish from other types of dermatitis at the clinical or the histological level, yet it has a very distinct cause and mechanism of induction. Exposure to certain environmental agents can elicit the development of an allergy specific for the sensitizing agent. Examples of sensitizers include plant-derived substances such as those in poison ivy and poison oak, metals such as nickel or chromium, or various other chemicals that may be encountered in an occupational setting.

The ACD reaction is marked by an influx of lymphocytes and monocytes into the affected area and is characterized by distinctive swelling, redness, and itching. In contrast to dermatologic diseases such as psoriasis where the etiology is poorly understood, the immunological basis of ACD is known in detail, and the reaction which occurs in humans can be accurately reproduced in various animals. Several elegant studies have clearly demonstrated the critical roles of both IL-1 and TNF in ACD. These experiments have shown that IL-1β is a critical mediator in the sensitization phase of allergic contact dermatitis (neutralization of IL-1β prevents sensitization to various allergens). However, it has been shown recently that epidermal TNF production is critical to Langerhans cell migration to the local lymph nodes where antigen presentation to T-cells takes place during the sensitization phase of ACD. Within 2–24 hours following poison ivy exposure (i.e. ACD), rapid onset of epidermal TNF protein expression was observed with a slower onset of IL-8 expression in sensitized human volunteers. Besides being the first detectable cytokine following an acute challenge, the predominant role of TNF was supported by the ability of anti-TNF antibody to abrogate the ear-swelling response in murine ACD reactions, both at the TNF mRNA level and relative to intensity of the inflammatory reactions. None of these inhibitory responses can be achieved equivalently by administration of antibodies for IL-2, IFN-γ, IL-3 or granulocyte/macrophage colony stimulating factor (GM-CSF). In a separate study, anti-TNF antibody demonstrated a dose-dependent suppression of the in vivo development of contact sensitivity. Since TNF appears to be the primary mediator of host responses, and can up-regulate IL-1 and IL-8 production both in an autocrine and paracrine fashion, it is logical and plausible that TNF plays the leading and central role in acute skin inflammation resulting from ACD.

Irritant contact dermatitis (ICD) is more prevalent than allergic contact dermatitis and can occur as a result of exposure to many different chemicals. This reaction occurs without prior sensitization and does not involve an immunological response specific for the irritating agent. While exposure to low levels of irritants may have no effect on the skin, irritant dermatitis occurs when the intensity or duration of the exposure exceeds the repair capacity of the skin or when the chemical elicits a nonspecific inflammatory response. The understanding of the pathogenesis of irritant dermatitis is incomplete, but the processes involved are readily studied experimentally in cultured cells, in animal models, or in human volunteers. For example, in cultured keratinocytes, agents that are known clinically to be irritating have been shown to stimulate the production of TNF, IL-1, and IL-8. In studies using mice, irritants caused the expression of a similar spectrum of cytokines; a marked infiltration of neutrophils into the irritated areas was also noted, an observation consistent with the effects of TNF-induced IL-8 and related cytokines. However, upregulation of TNF mRNA expression precedes that of IL-1 mRNA expression. In parallel with the clinical symptoms of ICD (induced by 10% sodium lauryl sulfate), an 8–10 fold increase in TNF and IL-6 was observed many hours before the 2–3 fold increase in IL-1β, IL-2 and GM-CSF in the peripheral human skin lymph. Lastly, it has been shown that administration of anti-TNF antibody prevents the development of ICD in mice. These observations indicate the involvement of proinflammatory cytokines, particularly TNF in the development of irritant dermatitis.

Sunburn is a clinical manifestation of over-exposure to UV light. It has been shown that there is an increase in the serum TNF level in man after UV treatment (see, Koch, et al., *J. Exp. Med.* 172:1609–1614 (1991)). Consequently, it has been suggested that the sunburn, fever and loss of appetite following exposure to UV is a result of TNF production.

Additionally, the present invention derives in part from a heretofore unrecognized sequence of cellular events which leads to the skin inflammatory response. This sequence includes the phases of (1) accentuated transepidermal water loss caused by an insult, injury or other chemical or physical stimulus to the skin, (2) a consequent change in the ion gradients normally maintained in the skin, (3) the release of pre-formed cytokines which are stored in the secretory vesicles within the keratinocytes, resulting in full-blown inflammation, and (4) the transduction of signals by keratinocytes to produce and/or secrete additional cytokines. The present invention exploits this heretofore unrecognized sequence of events to provide superior screening methods for anti-inflammatory drugs as well as new superior anti-inflammatory agents, methods and compositions.

The perturbation of the skin's barrier properties typically results from a disorganization of the lipids in the stratum corneum. Although lipids account for only a small percentage of the total stratum corneum weight, they are crucial for the provision of the permeability barrier by the skin. For example, perturbation of the lipid layer through topical solvent treatment has been found to result in a marked disruption in barrier function and thus, an increase in transepidermal water loss (TEWL). See Menon et al. (1985) *J. Lipid Res.* 26:418–427; Grubauer et al. (1989) *J. Lipid Res.* 30:323–334; and Grubauer et al. (1987) *J. Lipid Res.* 28:746–752. Accompanying barrier disruption and the resulting accelerated water transit is a perturbation of ion gradients across the epidermis. See Lo et al. (1990) *Dermatological* (Basel) 180:66–68. Previous studies have demonstrated ion gradients in the epidermis in vivo. For example, a low calcium concentration is found in the basal, proliferating layers, and progressively higher concentrations as one proceeds to the outer differentiated layers. See Menon et al. (1985) *J. Invest. Dermatol.* 84:508–512 and Forslind (1987) *Acta Dermato-Venereol. Suppl.* 134:1–8. Similar profiles are found in the cases of sodium, potassium, sulfur, chloride, and phosphorus ions. See Warner et al. (1988) *J. Invest. Dermatol.* 90:78–85. The increased ion flux caused by the accelerated water transit disrupts these homeostatic ion gradients in the skin.

Significantly, the concentration profiles for sodium, potassium, calcium, and chloride each possess a major inflection point at the stratum corneum-granulosum junction. As discussed above, passive water loss can disrupt these concentration gradients and shift the inflection points. Without wishing to be bound by any particular theory, this increased water loss and the resulting passive ion flux and disruption of the ion gradients and cellular concentrations in the skin provide a signal for the enhancement of secretory granule formation and secretion. Interestingly, in most secretory systems, increases in intracellular calcium concentration stimulate secretion. See Rubin (1970) *Pharmacol. Rev.* 22:389–428, Schoen et al. (1988) *Am. J. Med.* 84:492–502, and Hurwitz L. et al. "Calcium Channels: Their Properties, Functions, Regulation and Clinical Relevance" 1991 by CRC Press, Inc. Again, without wishing to be bound by any particular theory, it appears that decreased intracellular calcium stimulates secretory granule secretion in keratinocytes. This is analogous to the situation in the parathyroid gland where decreased calcium concentrations increased parathyroid hormone secretion. See Brown (1991) *Physiol. Rev.* 71:371–411.

Specifically, preformed lipids; enzymes, including acid phosphatase, proteases, lipases, and glycosidases; and significantly, proteins, including preformed cytokines, such as TNF and IL-1, found in the stratum corneum are released by some secretory granules. For example, the presence of preformed TNF and IL-1 in the upper layers and in the intercellular domain of the epidermis/stratum corneum and in isolated enriched secretory granule (lamellar body) preparation has been confirmed by the inventors using immunohistochemical staining and Western blot analyses.

Again, without wishing to be bound by any particular theory, under normal homeostatic conditions, cornification of the cellular envelope, immobilization in the lipid matrix, and the presence of naturally occurring antagonists in the granulosum-stratum corneum junction could be the protection mechanisms that serve to prevent inward flux of the preformed cytokines produced by the extrusion process and constitutively present in the stratum corneum. In fact, the stratum corneum could function as the excretory or consolidating system for constitutively-produced cytokines. However, under a diseased or distressed state where the cornification and possibly, also the synthesis or the release of natural cytokine antagonists is incomplete, the accelerated extrusion process and thus, the overall high local level of proinflammatory cytokines could initiate and/or propagate the local skin inflammatory and immune responses.

Additionally, it has been found that like the granulocytes, epidermal keratinocytes, monocytic/macrophage cell types, and perhaps also other epithelial and endothelial tissues, initiate their production and/or release of proinflammatory cytokines using a common signaling pathway. This primary signaling pathway may involve one or more ionic species, such as calcium or chloride ions, as the secondary intracellular mediators through which the cellular membrane signal is transduced to the cytosolic domains where either various promotional and regulatory mechanisms are activated to induce production or enhance the release of cytokines such as TNF-$\alpha$ and IL-1. These secondary messenger ions may come either from the influx of extracellular ions through activation of membrane ion channels or from intracellular storage organelles or compartments. Cytokines produced as a result of the gene transcription, translation and release then initiate the inflammatory cascade.

Although much of the discussion herein has centered on techniques for regulating the rate of cytokine production in the skin, the same techniques will be applicable to modulating the formation and release of proinflammatory cytokines in mucosal membranes, such as buccal, nasal, corneal, colonic, ocular and pulmonary membranes. See, e.g., Mackay et al. (1991) *Adv. Drug Del. Rev.* 7:313–338. There are several notable similarities between skin and mucosal membranes. For example, the buccal membrane is stratified in a like manner to the skin, with both tissues comprising polygonal cells at the basal membrane leading to squamous cells at the surface. Additionally, the non-keratinized tissues, such as the floor of the mouth and buccal mucosa, have epithelia, which, like the skin, act as effective rate-limiting steps to absorption. Therefore, the buccal epithelium can be regarded as having less completely differentiated keratinocytes as compared with the epidermis.

III. Embodiments of the Invention

A. Screening Assays

The above-described model of ion-mediated secretory granule extrusion and cytokine regulation has important implications for the development of new technologies for screening assays to identify compounds having desirable anti-inflammatory properties, both for treatment of inflammatory and TNF-mediated conditions, and for prophylactic use. By focusing assays on the production and release of cytokines, such as TNF, IL-1, IL-6 and IL-8, anti-inflammatory compounds may be found which lack the harsh side effects of those compounds currently used to alleviate inflammation. Such assays also provide a means to identify compounds which can enhance the cytokine productions.

Thus, in one aspect, the present invention provides assays for screening putative skin immune modulating agents. The assays of the invention include a variety of formats which are effective in identifying those agents capable of modulating the production of cytokines in keratinocytes or other epithelial tissues. Most generally, the assays of the invention will comprise the steps of (i) inducing production of at least one cytokine or MHC Class II molecule in primary human keratinocytes, i.e., keratinocytes isolated from human tissues or human skin; (ii) exposing a portion of the stimulated cells or tissues to putative skin immune modulating agent; and (iii) determining whether the putative agent is effective to modulate cytokine or MHC Class II molecule expression production by the keratinocytes or tissues exposed to the putative agent as compared to keratinocytes or tissues which have not been exposed to the putative agent.

These assays may include in vitro assay systems or in vivo assay systems. The in vitro systems utilize direct quantitation of the production of cytokines with representative assay techniques including (1) enzyme-lined immunosorbent assays (ELISAs); (2) Radioimmunoassay; (3) gel electrophoresis and/or Western blots; (4) Immunohistochemistry; and (5) Bioassays. Indirect quantitation of the formation of cytokines is also possible using such techniques as (1) Northern blots; (2) in situ hybridization; (3) reverse transcriptase polymerase chain reaction (RT-PCR); (4) ribonuclease protection assays; and (5) nuclear run-on assays.

1. In vitro Assays a. Direct Measurement of Cytokine Production

The present invention also contemplates the direct measurements of cytokine levels in assays for determining immunomodulating agents. These include the direct measurement of protein expression using methods such as (1) ELISA; (2) radioimmunoassay (3) gel electrophoresis or western blotting; (4) immunohistochemistry; and (5) bioassays such as (i) the WEHI 164 and the L929 assays for TNF, (ii) the D10 assay for IL-1, (iii) the B9 assay for IL-6, (iv) the CTLL assay for IL-2, and (v) the neutrophil chemotaxis assay for IL-8.

(1) ELISA

ELISA techniques for evaluating the skin immune response are well-known in the art (see, e.g., Kenney, et al., *J. Immunol.* 138:4236 (1987),which is incorporated herein by reference; and Harlow, supra). The ELISA protocol involves coating the wells of microtiter (ELISA) plates with a monoclonal or polyclonal antibody directed to the cytokine of interest, e.g., an anti-TNF antibody, at a concentration of between about 0.5–15 $\mu$g/ml. The antibody solution is allowed to incubate in the wells for about 12–24 hours at 4° C. in a humid atmosphere. The unbound antibody is washed away, and the open sites are blocked with an inert protein, such as bovine serum albumin (BSA) in PBS, which is allowed to incubate in the wells for 1–3 hours. The blocking solution is discarded and about 50 $\mu$l of the sample keratinocyte supernatant, obtained from the cell pellet of keratinocytes after centrifugation as described above, is added to the ELISA wells. For quantitation the sample solution is serially diluted in PBS buffer. After an incubation period, typically one to five hours at 37° C., preferably one to two hours, more preferably one hour, or about 12 hours at 4° C., the plates are again washed and the second antibody directed to the cytokine, e.g., a polyclonal rabbit anti-TNF antibody, is applied. After an incubation period, typically one to five hours, preferably one to two hours, more preferably one hour, the plates are again washed. A biotin-labeled third antibody, directed against the second antibody, is added (e.g., goat anti-rabbit) and incubated for about 0.5–1 hour at 37° C. After washing the unbound material, horseradish peroxidase-labeled streptavidin is added and incubated for 0.5–1 hour at 37° C. Because the cytokine is situated between two layers of antibodies, this type of assay is often called a sandwich ELISA. Subsequent steps using an o-phenylene diamine (OPD) substrate (e.g. 1 mg/mL OPD/ 0.3% $H_2O_2$/0.1 M citrate buffer) permit color development, with the intensity of color varying according to the amount of TNF specifically bound. Alternatively, the second enzyme may be biotinylated to eliminate the need for a third antibody. Other methods of assay will be apparent to those of skill in the art. The ELISAs for human and murine TNF are quite sensitive, reliably detecting cytokine concentrations of less than 50 pg/mL.

(2) Radioimmunoassay

Radioimmunoassay may also be used to quantitate the production of cytokines in a manner similar to that just described for quantitation by ELISA. Generally, a first cytokine specific antibody is attached to a substrate using standard techniques, such as those described in Harlow or Sambrook, et al., MOLECULAR CLONING: A LABORATORY MANUAL (Cold Spring Harbor 1989), which is incorporated herein by reference. The bound antibody is then exposed to the supernatant taken from keratinocytes cultured with a putative skin anti-inflammatory substance. A second antibody, carrying a radioactive label such as $^{125}$I-modified tyrosine is added to the bound cytokine and allowed to incubate as described above. Typically the labelled antibody has a specific activity of about $5 \times 10^6$ cpm/$\mu$g. The unbound labelled material is washed away and the remaining label quantitated, using standard techniques, e.g., a scintillation counter.

(3) Gel Electrophoresis and Western Blotting

As an alternative, the presence of TNF and other proteins can be assessed by Western blot analysis (see, e.g., Didierjean, et al., *J. Invest. Dermatol.* 92:809 (1989), which is incorporated herein by reference). In addition, Western blot analysis can be used to analyze samples that cannot be accurately tested in the ELISAs and the WEHI assay (below) due to high protein concentration or the presence of various detergents or solubilizing agents (as is the case with skin homogenates and lamellar body preparations).

Generally, this procedure involves electrophoresing the cell supernatant samples on reducing or non-reducing SDS-polyacrylamide gels using standard techniques such as those described in Sambrook. The separated protein in the gel is electrophoretically blotted onto a nitrocellulose membrane, nylon membrane or some other suitable support, again using common techniques. This membrane is first blocked with an inert protein, then incubated with a solution containing an antibody to the protein of interest, such as one of the antibodies described above, to bind to the immobilized protein. Preferably the first antibody is a monoclonal antibody which has been raised against the denatured cytokine or a high-titer polyclonal antiserum. The bound protein-antibody complex is subsequently incubated with a second labelled antibody specific for the first antibody to form a protein-antibody-antibody complex. For example, the second labelled antibody may be labelled with a colorimetric label, e.g., biotin or horseradish peroxidase, or the antibody may be radiolabelled, e.g., with $^{125}$I, $^{35}$S or $^{32}$P. The bound antibody-cytokine complex is then assayed using the method appropriate for the label as described above. Of course, one of skill in the art will recognize that the protein may be purified and identified merely by separation on a suitable gel, such as sodium dodecylsulfate (SDS) gel if the amount of protein in the sample is sufficiently large.

(4) Immunohistochemistry

Similar to Western blotting, immunohistochemistry provides information of a qualitative and quantitative nature.

The strength of this procedure is that it allows visualization and localization of the distribution of a specific cytokine among various cell types or within different regions of a tissue (see, e.g., Griffiths, et al., *Br. J. Dermatol.* 124:519 (1991), which is incorporated herein by reference). In performing this procedure, tissue samples are flash frozen in an embedding compound, e.g., Tissue-Tek OCT (available commercially from Miles, Inc., Elkhart, Ind.), and stored at −70° C. until used. The tissue is then cut into sections, typically 6 μm sections, and placed on microscope slides. The sequence of steps that follow are quite similar to the procedure involved in the development of a Western blot. After fixing the tissue in acetone, the slides are incubated with serum, typically goat serum, to block nonspecific binding sites. The samples are subsequently incubated with a specific antibody directed against the cytokine of interest. After thorough washing, a second, labelled antibody, e.g., a biotinylated antibody, is added and the amount of bound label is quantitated using standard techniques. For example, when a biotinylated antibody is used, avidin conjugated with biotinylated horse radish peroxidase is added, followed by incubation with a chromogenic peroxidase substrate, to initiate a colorimetric reaction. The sample is then counter-stained with hematoxylin. The presence of chromogen, the color of which will depend on the particular substrate being used, is indicative of the presence of the cytokine of interest. Care must by taken, however, to ensure that the staining pattern is specific. A control antibody is used for comparison with the anti-cytokine antibody. Untreated control tissue or cells are also compared to tissues or cells that have been subjected to an inflammatory stimulus.

(5) Bioassays

In addition to the above-described assay methods, several bioassay techniques are available. In contrast to ELISAs which measure the immunologic reactivity of a cytokine using specific antibodies, bioassays utilize a specific biologic effect of a cytokine as the basis for the assay. For example, TNF is cytotoxic for tumor cell lines and IL-1 stimulates T-cell proliferation. The WEHI bioassay for TNF and the D-10 bioassay for IL-1 capitalize on these activities. The actual cell count can be determined at the end of the bioassay incubation period by (a) incorporation of a radioactive precursor (e.g., [$^3$]thymidine), or (b) a colorimetric development of compounds introduced into the cell that are indicative of cellular metabolic activity (e.g., MTT, neutral red, or LDH). The keratinocytes themselves, or the supernatants from the keratinocytes cultured with various stimuli and/or drugs, can be assayed by bioassay in the same way they are used in the ELISAs.

(a) WEHI/L-929 Bioassays

The WEHI and L-929 bioassays allow for the determination of the concentration of biologically active cytokines. The most sensitive TNF bioassay is performed using the WEHI cells, a mouse fibrosarcoma cell line that is exquisitely sensitive to the cytotoxic effects of TNF (see, e.g., Espevik, et al., *J. Immunol. Methods* 95:99 (1986), which is incorporated herein by reference). The L929 cell line is also commonly used in a similar TNF bioassay (see, e.g., Ruff, et al., *J. Immunol.* 125:1671 (1980), which is incorporated herein by reference). In performing the WEHI assay, the supernatant samples are serially diluted across a 96 well plate and the WEHI cells are then added. After an incubation of 16–24 hours, preferably 18–22, and most preferably, 20 hours, MTT (3-[4,5-dimethylthiazol-2-yl]-2,5-diphenyltetrazoliun bromide), typically 20 μl of 5 mg/mL solution in PBS is added to the wells and incubated for 4 hours at 37° C. This reagent is metabolized to a colored end product only by viable cells and thus allows determination of the extent of WEHI cell toxicity. Using a standard curve of serially diluted recombinant TNF, the concentration of TNF in the samples can be calculated. After color development, the percentage of dead cells P can be determined by the formula: where $OD_{supernatant}$ is the optical density of the solution in wells containing supernatant and $OD_{control}$ refers to the optical density of solution in control wells. The optical densities of the solutions is determined using standard methods. Alternatively, the TNF concentration may be determined by comparison with the standard curve using methods well-known in the art.

(b) D-10 Assay for IL-1

IL-1 released from activated keratinocytes can be quantitated using the D-10 assay described by Kurt-Jones, et al., *Proc. Natl. Acad. Sci. USA* 82:1204 (1985), which is incorporated herein by reference. Supernatant from the tested cells is placed in several wells and cultured with (i) $10^6$ A/J or C3H/HeJ thymocytes, (ii) $10^6$ thymocytes and 5 μg/mL phytohemagglutinin (PHA) and (iii) $2 \times 10^4$ D10.G4.1 T cells and 2.5 μg/mL concanavalin A (Con A). The cultures are incubated at 37° C. in a 5% $CO_2$ atmosphere. After 48 hours of incubation, each well is pulsed with 0.2 μCi of $^3$H thymidine. The cells are harvested within 18–24 hours following the addition of the $^3$H thymidine and the amount of $^3$H incorporation by the cells is determined using standard methods. The amount of IL-1 present in the supernatant is determined by comparing the measured incorporation against the amount of incorporation of $^3$H in cells incubated in standard concentrations of IL-1. For example, one unit of IL-1 per milliliter may be defined as the concentration of IL-I required to produce half-maximal proliferation of D10.G4.1 cells. Using this definition, one of skill in the art can determine the IL-1 units of solutions having known IL-1 concentrations for comparison with the IL-1 units determined for the supernatants of keratinocytes incubated with various concentrations of a putative skin immune modulation agent to determine the actual IL-1 concentration of the supernatants.

(c) B-9 Assay for IL-6

The IL-6 bioassay takes advantage of the B-9 cell line, a hybridoma line that is dependent on IL-6 for growth (see, e.g. Aarden, et al., *Eur. J. Immunol.* 17:1141 (1987), which is incorporated herein by reference). The assay is performed quite similarly to the WEHI assay, although the endpoint being examined is the extent of cell proliferation rather than cytotoxicity. Samples to be analyzed for IL-6 are serially diluted across a 96 well plate, and the B-9 cells are added. After a three day incubation at 37° C. in a humidified atmosphere containing 5% $CO_2$, the cells are dosed with MTT as described for the WEHI assay. This reagent is metabolized to a colored end product by viable cells such that the extent of color development is proportional to the degree of proliferation of the cells. The cells may also be incubated with [$^3$H]thymidine ([$^3$H]thd) and the extent of incorporation determined. The concentration of IL-6 in the samples can be calculated by comparing the results of the samples with the results of B-9 cells incubated with known quantities of IL-6.

(d) CTLL Assay for IL-2

The CTLL assay for IL-2 (T-cell Growth Factor, or TCGF) can be used to quantitate the amount of IL-2 present in samples taken from cells incubated with putative anti-inflammatory agents (see, e.g., Gills, S., et al., *J. Immunol.* 120:2027 (1978)). Murine (C57BL/6) tumor-specific cytotoxic T lymphocytes (CTLL 1 and CTLL 2, described by Gills, et al., *Nature*, 268:154 (1977) and *J. Exp. Med.* 146:168 (1977)) are maintained in a IL-2-dependent long-term proliferative culture. The cells are washed free of growth medium using standard techniques and resuspended in Click's medium (Altich Assoc., Hudson, Wash.) supplemented with 2% FCS, 50 units/mL penicillin, 50 μg/mL gentamicin, 16 μg/mL NaHCO$_3$ and 25 μM/mL HEPES and placed in microtiter wells. The supernatant to be assayed is then added to the cells in serial dilutions. The plates are incubated at 37° C. in a humidified atmosphere of 5% CO$_2$ in air. Following 24 hours of culture, 0.5 μCi of $^3$H-thymidine (Schwartz/Mann Inc., Orangeburg, N.J.) having a specific activity of 1.9 μCi/mM is added to each well and the culture continued for another 4 hours. The cultures are harvested onto glass fiber filter strips and the $^3$H-thymidine incorporation is determined using known techniques (Oppenhiem, et al., MANUAL OF CLINICAL IMMUNOLOGY, American Society for Microbiology, Washington, D.C., Rose, Ed. (1976), which is incorporated herein by reference).

(e) Determination of IL-8 or Monocyte Chemotactic Protein from Chemotaxis Assays The neutrophil chemotaxis assay for IL-8 (see, e.g., Standiford, et al., *J. Clin. Invest.* 86:1945 (1990), which is incorporated herein by reference) is also included in the invention as another means of assessing putative immune modulating agents. Similar chemotaxis assays are also available, such as assays for the expression of monocyte chemotactic protein using the monocyte chemotaxis assay (Elner, S., et al., *Lab. Invest.* 64:819, which is incorporated herein by reference). Generally, human monocytes having greater than 95% viability are prepared from peripheral blood by density gradient centrifugation, e.g., using a Ficoll-Hypaque gradient, and suspended at 3×10$^6$ cells/mL in Hanks' balanced salt solution (HBSS). 100–300 μl of supernatant diluted with HBSS or positive control solution of formylmethionylleucylphenylalanine (fMLP) (10$^{-7}$–10$^{-8}$ M,Sigma), or a negative control solution of HBSS alone are placed in duplicate bottom wells of a microchemotaxis chamber, such as that sold by Neuroprobe (Cabin John, MD). A 3–5 μm pore size polycarbonate filter, which is polyvinylpyrrolidone free (Neuroprobe, Cambridge, Mass.) is placed in the assembly and 100–300 μl of monocyte suspension is placed atop each well. After incubation at 37° C. in a humidified atmosphere of 5% CO$_2$ in air for 2 hours, the filters are removed, fixed in methanol, and stained with 2% toluidine blue (Aldrich). Monocytes which migrate to the bottom of the filters are counted in 10 microscopic high-power field (HPF) (×1,000). Chemotactic activity is expressed as the mean number of cells/HPF. Supernatant from keratinocytes incubated in an agent effective to modulate cytokine production will be associated with an increase or decrease in cell/HPF compared to control depending on whether the putative agent is effective to enhance or suppress cytokine production.

b. Measurement of Cytokine Gene Expression

In addition to examining the regulation of cytokines at the level of protein production, assessment of mRNA levels is a valuable indicator of alterations in the level of expression of a particular gene. Although modulation of mRNA and protein levels often occur in tandem, this is not always the case. For example, modifications of the protein after its synthesis may increase its stability without any corresponding changes in the mRNA. Conversely, increases in mRNA production may not translate into increase amounts of protein as (1) the mRNA is unstable; (2) translational interference or bottlenecks in processing prevent a corresponding increase in protein production; or (3) the protein produced is unstable. In addition, some drugs are known to inhibit cytokine production at a post-transcriptional level and leave mRNA expression unaffected. Therefore, examination of transcription provides important information on mechanisms of gene regulation as well as the mechanisms of action of drugs. Techniques such as (a) Northern blotting; (b) in situ hybridization; (c) polymerase chain reaction; (d) ribonuclease protection assays; and (e) nuclear run-on assays are effective means of measuring the production, processing and/or stability of mRNA.

(1) Northern Blotting

Northern blotting has been used to determine the extent of mRNA production of cytokines as an indirect measure of cytokine concentration (see, Kunkel, S. L., et al., *J. Biol. Chem.* 263:5380 (1988), which is incorporated herein by reference). RNA from cells used in an assay is separated on an agarose gel and the separated RNA transblotted onto a nylon or other suitable membrane. The membrane-bound RNA is probed with specific nucleic acid sequences which will bind to the mRNA encoding the amino acid sequences of the cytokines of interest. The probes are labelled, e.g., with $^{32}$p, to allow detection of probe binding to the appropriate mRNA. However, nonradioactive labeling and detection procedures may be used. An example of a non-radioactive labelled probe is one wherein the probe sequence includes digoxigenin (DIG)-labeled deoxyuridyltriphosphate (dUTP). The single stranded DIG-dUTP-labeled probes hybridize with the nucleic acids on the nylon membrane under conditions where the temperature and salt concentrations are carefully controlled. The optimal conditions are sequence-dependent and therefore one of skill in the art will recognize that the choice of appropriate conditions will depend on the circumstances. Generally, stringent conditions are selected to be about 5° C. lower than the thermal melting point (T$_m$) for the specific sequence at a defined ionic strength and pH. The T$_m$ is the temperature at which 50% of the target sequence hybridizes to a perfectly-matched probe at a given temperature and pH. Typically, stringent conditions will be those under which the salt concentration is at least about 0.1–0.4 M at a pH of 7 and a temperature of about 60°–70° C. After several washing steps at different levels of stringency, the blot is developed much like a Western blot, using an anti-DIG antibody followed by color development steps.

(2) In situ Hybridization

Similar to immunohistochemical analysis of level of protein expression, in situ hybridization is a qualitative procedure that allows the direct visualization of cellular mRNA levels in cultured cells or tissue sections (Remick, D. G., et al., *Lab. Invest.* 59:809 (1988), which is incorporated herein by reference). The relative expression of mRNA in different cell populations or in different regions of the tissue can be determined. Cell samples are affixed to microscope slides using standard methods and reagents. The fixed cells are incubated in ethanol, and the sample is hybridized with a DNA probe specific for the cytokine of interest by placing a small volume of the probe on the slide, covering the slide, and incubating the slide overnight in a humidified atmosphere. The probes are labeled, typically with $^{35}S$, but non-radioactive probes labeled with DIG-dUTP as described can also been used. After hybridization, the slides are carefully washed under stringency conditions to remove all non-bound material, and the probe is visualized. For example, where the label is $^{35}S$, the slides are covered with a photographic emulsion and developed after a week-long exposure. For DIG-labeled probes, a color development procedure is performed that is similar to that used for a Western blot. After counterstaining with hematoxylin, the distribution of the probe can be visualized at the level of the light microscope.

(3) RT-PCR

A very sensitive and powerful technique for assessing mRNA levels is reverse transcriptase-polymerase chain reaction (RT-PCR, see, e.g., Erlich, PCR TECHNOLOGY (Freeman 1992), and Kilgus, O., et al., *J. Invest Dermatol.* 100:674 (1993), and U.S. Pat. Nos. 4,683,195, 4,683,202, 4,965,188 each of which is hereby incorporated by reference.) In this procedure, total RNA is isolated from a sample and the mRNA copied to DNA (cDNA) using reverse transcriptase. This cDNA is then added to a PCR reaction containing DNA primers which specifically target the mRNA species of interest. This PCR product is electrophoresed on an agarose gel, stained with a fluorescent dye, and photographed. The intensity of the staining of the PCR product is proportional to the concentration of the product and can be quantitated using a densitometer. Moreover, β-actin, a housekeeping gene whose expression is relatively constant under various treatment conditions, is analyzed in parallel with the cytokine genes. By normalizing the expression of various genes based on β-actin expression, semi-quantitative determination of mRNA concentrations can be achieved by RT-PCR. Primers have been designed, acquired, and prepared that allow the study of several different mRNA species, including human TNF, IL-1α, IL-1β, ICAM-1, IL-8, TGF-β, and β-actin as well as mouse TNF, IL-1α, IL-1β, KC, IL-10, GM-CSF, IFN-γ, and β-actin.

"Polymerases" refers to enzymes able to catalyze the synthesis of DNA or RNA from nucleoside triphosphate precursors. In the amplification reactions of this invention, the polymerases are template-dependent and typically add nucleotides to the 3'end of the polymer being formed. It is most preferred that the polymerase is thermostable as described in U.S. Pat. No. 4,889,819, incorporated herein by reference.

To avoid the problems of PCR contamination, the handling of samples and isolation of DNA may be performed in a hood with laminar air flow, preferably in an area not used for the preparation of DNA template-free PCR cocktails and not used for analysis and cloning of PCR products.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids from biological samples are known in the art.

The cells are resuspended ($10^6$ nucleated cells per 100 μl) in a buffer of 50 mM Tris-HCl (pH 8.3), 50 mM KCl 1.5 mM $MgCl_2$, 0.5% Tween 20, 0.5% NP40 supplemented with 100 μg/mL of proteinase K. After incubating at 56° C. for 2 hr, the cells are heated to 95° C. for 10 min to inactivate the proteinase K and immediately moved to wet ice (snap-cool).

If gross aggregates are present, another cycle of digestion in the same buffer should be undertaken. Ten μl of this extract will be used for amplification.

When the sample contains a small number of cells, extraction may be accomplished by methods as described in Higuchi, "Simple and Rapid Preparation of Samples for PCR", in PCR TECHNOLOGY, Ehrlich, H. A. (ed.), Stockton Press, New York, which is incorporated herein by reference. The cells in the sample are suspended in 20 μl of PCR lysis buffer (10 mM Tris-HCl (pH 8.3), 50 mM KCl, 2.5 mm $MgCl_2$, 0.1 mg/mL gelatin, 0.45% NP40, 0.45% Tween 20) and frozen until use. When PCR is to be performed, 0.6 μl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a-salting out procedure adapted from the method described by Miller et al., *Nucleic Acids Res.*, 16:1215 (1988), which is incorporated herein by reference. Mononuclear cells are separated on a Ficoll-Hypaque gradient. The cells are resuspended in 3 mL of lysis buffer (10 mM Tris-HCl, 400 mM NaCl, 2 mM $Na_2EDTA$, pH 8.2). Fifty μl of a 20 mg/mL solution of proteinase K and 150 μl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 μl of the 20 mg/mL proteinase K solution is mixed in the solution and incubated for another night at 37° C. on a gently rocking or rotating platform. Following adequate digestion, one mL of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 mL tube that contains 4 mL of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air dried. The precipitate is placed in distilled water and dissolved.

Another commonly used procedure for isolating nucleic acids is a modification of the method of Chirgwin et al., *Biochemistry* 18:5294 (1979) and Jonas et al., *Proc. Natl. Acad. Sci. USA* 82:5413 (1985). Briefly, samples are lysed in a nucleic acid extraction buffer (25 mM Tris, pH 8.0, 4.2 M guanidine isothiocyanate, 0.5% Sarkosyl, and 0.1 M 2-mercaptoethanol). Whole tissue is processed by homogenization in this buffer, while cultured cells are scraped into this buffer and pipetted vigorously. The sample is then mixed with equal volumes of an extraction buffer (100 mM Tris, pH 8.0, 10 mM EDTA, and 1% SDS), chloroform:isoamyl alcohol (24:1), and phenol (saturated with 10 mM Tris, pH 8.0, 1 mM EDTA). After vortexing the sample vigorously, it is centrifuged to separate the organic and aqueous phases. The aqueous phase is extracted again with chloroform:isoamyl alcohol and phenol and twice more with chloroform:isoamyl alcohol. The nucleic acid is precipitated from the final aqueous phase by adding a one tenth volume of 3M sodium acetate, pH 5.2, and an equal volume of isopropanol. After incubating the samples overnight at −20° C. or for 1 hour at −70° C., the samples are centrifuged to recover the precipitated nucleic acid. The nucleic acid pellet is washed in 70% ethanol/30% diethyl pyrocarbonate (DEPC)-treated water, repelleted, dried, and solubilized in DEPC water.

Kits are also commercially available for the extraction of high-molecular weight DNA for PCR. These kits include Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA may be determined by spectrophotometric analysis of the absorbance of a diluted aliquot at 260 nm and 280 nm.

In order to perform PCR amplification of RNA, it must first be transcribed into cDNA using a reverse transcriptase enzyme. Many different protocols exists for this reaction, but one that is used commonly is as follows. A solution is heated to 65° C. for 5 minutes to eliminate any secondary structure of the RNA and then immediately frozen by placing on dry ice or by putting in a −70° C. freezer. A mixture is then added to the RNA such that the final concentration of reagents is 20 U/μl Moloney murine leukemia virus reverse transcriptase (such as that available from GIBCO/BRL), 1× buffer (which is supplied with the enzyme by the manufacturer), 1.3 U/μl RNase inhibitor, 50 μg/mL oligo dT, 0.1 mg/mL acetylated bovine serum albumin, 0.5 mM dNTP (a mixture of dATP, dCTP, dGTP, and dTTP each at a concentration of 0.5 mM), and 10 mM dithiothreitol. The reaction mixture is incubated at 42° C. for 1 hour and subsequently at 95° C. for 5 minutes to inactivate the enzymes. This reaction results in the generation of cDNA species for only the mRNA fraction of the total RNA due to the use of an oligo dT primer, which binds to the poly A tail of eukaryotic mRNA. Other species of RNA as well as mRNA can be transcribed into cDNA by using random hexamer oligodeoxyribonucleotide primers. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the RNA template is heat degraded during the first denaturation step after the initial reverse transcription step leaving only DNA template.

After extraction of the DNA, or preparation of the cDNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for an sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology*, 43:63–67; and Radding, 1982, *Ann. Rev. Genetics* 16:405–436, each of which is incorporated herein by reference).

Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis.

Suitable polymerases for use with a DNA template include, for example, *E. coli* DNA polymerase I or its Klenow fragment, $T_4$ DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR TECHNOLOGY, supra.

The PCR method can be performed in a step-wise fashion, where after each step new reagents are added, or in a fashion where all of the reagents are added simultaneously, or in a partial step-wise fashion, where fresh or different reagents are added after a given number of steps. For example, if strand separation is induced by heat, and the polymerase is heat-sensitive, then the polymerase must be replenished following each round of strand separation. However, if, for example, a helicase is used for denaturation, or if a thermostable polymerase is used for extension, then all of the reagents may be added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the temperature of the reaction mixture is cycled through a denaturing region, a primer annealing region, and an extension reaction region. Alternatively, the annealing and extension temperature can be the same. A machine specifically adapted for use with a thermostable enzyme is commercially available from Perkin Elmer Cetus, Inc.

Those skilled in the art will also be aware of the problems of contamination of a PCR by the amplified nucleic acid from previous reactions and nonspecific amplification. Methods to reduce these problems are provided in PCT patent publication [WO 91/05210], incorporated herein by reference. The method allows the enzymatic degradation of any amplified DNA from previous reactions and reduces nonspecific amplification. The PCR amplification is carried out in the presence of dUTP instead of dTTP. The resulting double-stranded, uracil-containing product is subject to degradation by uracil N-glycosylase (UNG), whereas normal thymidine-containing DNA is not degraded by UNG. Adding UNG to the amplification reaction mixture before the amplification is started degrades all uracil-containing DNA that might serve as target. Because the only source of uracil-containing DNA is the amplified product of a previous reaction, this method effectively sterilizes the reaction mixture, eliminating the problem of contamination from previous reactions (carry-over). UNG itself is rendered temporarily inactive by heat, so the denaturation steps in the amplification procedure also serve to inactivate the UNG. New amplification products, therefore, though incorporating uracil, are formed in an effectively UNG-free environment and are not degraded.

(4) Ribonuclease Protection Assay

This procedure uses hybridization of labeled RNA probes to a sample mixture of RNA as a means of quantitating the levels of a specific mRNA species of interest (see, e.g., Zinn, et al., *Cell* 34:865–879 (1983), which is incorporated herein by reference). Briefly, the sequence of the cytokine of interest is cloned into a plasmid specifically designed for the generation of RNA probes. Using a suitable RNA polymerase, such as a bacterial polymerase, RNA corresponding to the sequence of interest is synthesized in the presence of a label; this is typically a $^{32}$P-labeled ribonucleoside triphosphate, but could also potentially be a nonradioactive label, such as DIG-UTP. The probe is then isolated and allowed to hybridize with the mRNA in the sample of interest. Following hybridization, a ribonuclease is added, with this enzyme degrading any unhybridized, single-stranded RNA. The resulting mixtures is then run on a gel to separate the fragments by size and subjected to autoradiography or color development. Only labeled probe that has bound to the corresponding RNA species in the sample will remain intact and will be detectable on the gel. This method is quite sensitive as well as quantitative.

(5) Nuclear Run-on Assay

Nuclear run-on assays are a powerful tool that can be used to explore the transcriptional activity of a cytokine gene and answer questions regarding whether the increase in steady-state mRNA levels as assessed by Northern blot is due to an increase in the transcription of the gene or due to an increase in the stability of the mRNA (see, e.g., Zuckerman, et al., *Immunology* 73:460–465 (1991), which is incorporated herein by reference). A cDNA specific for the cytokine of interest is fixed to a solid support, e.g., nitrocellulose or nylon membrane, using standard techniques. Cells are then stimulated with putative pro-inflammatory agents in the presence of a ribonucleoside triphosphate labeled with, e.g., $^{32}$P, $^{35}$S, $^{125}$I or with DIG-UTP. The cells are lysed using standard techniques, e.g., using 0.5% NP-40 in 10 mM Tris, pH 7.4, 10 mM NaCl, 3 mM $MgCl_2$. The nuclei may be stored. The nuclei of the cells are isolated and the actively transcribed RNA containing the label is applied to the cDNA-containing membrane. After hybridization and washing, the blot is subjected to autoradiography or color development.

c. Transcription of Cytokines: Identification of Cytokine-Specific Transcriptional Regulatory Elements The present invention also contemplate the identification of transcriptional regulatory elements related to proinflammatory cytokines and the use of such regulatory elements to identify agents effective to suppress or enhance the transcription of DNA sequences encoding proinflammatory cytokines. DNA sequences within or flanking a cytokine gene which is preferentially expressed in keratinocyte cells contain DNA sequence motifs which function to enhance or drive transcription of the cis-linked gene in keratinocytes. These sequences are termed cytokine-specific transcriptional regulatory sequences. Such sequences are isolated and evaluated for their capacity to enhance or drive transcription of an operably linked reporter gene (e.g., chloramphenicol transferase, CAT) in keratinocytes and substantially not in other cell types. Minimal functional sequences are defined by deletion analysis and/or linker-scanning mutagenesis and the like, followed by assay of transcriptional activity demonstrating transcription in transfected keratinocyte cells but not in other cell types which have also been transfected with minimal reporter constructs.

The enhancer region may be derived from the 5' flanking region of a cytokine gene, where the cytokine gene selected is normally expressed in primary human keratinocytes. The enhancer region will include at least that portion of the 5' flanking region which is bound by the transcription factors induced by cytokines which are produced as a result of stimulation of the keratinocyte.

The enhancer region can be obtained by isolation and purification from a suitable genomic library, optionally using certain conserved sequences as identification probes which are well-known in the art. Alternatively, the conserved sequences themselves may be synthesized by well known means, such as using commercially available gene synthesizers, and incorporated into the DNA constructs by conventional means.

Suitable marker genes will produce a detectable signal upon stimulation which indicates that the cytokine transduction pathway of the keratinocyte has been induced. Conveniently, a detectable signal will be visibly or optically detectable to facilitate screening of multiple samples simultaneously, for example using multiple-well microtiter plates. Particularly suitable are marker genes which produce a visible change within the culture media of the cultured cells, such as chromogenic (color) signals, fluorescent signals, luminescent signals, and the like. The use of the firefly luciferase (Luc) gene is preferred. Other suitable marker genes include β-galactosidase and chloramphenicol acetyl-transferase.

The enhancer region and the marker gene will be incorporated into a suitable DNA construct by conventional recombinant DNA techniques in order to facilitate introduction into the starting keratinocytes. Usually, for easy construction, the DNA construct will be prepared from a bacterial plasmid where the enhancer, the marker gene, and usually a suitable promoter region, will be sequentially introduced in proper reading frame so that binding of a nuclear regulatory protein to the enhancer region will result in increased expression of the marker. The plasmid will usually include at least one antibiotic resistance gene to facilitate construction of the plasmid as well as screening of transfected cell lines to identify those which have stably incorporated the plasmid DNA.

The DNA plasmid as a whole, or portions thereof including the enhancer, promoter, marker gene, and optionally antibiotic resistance gene, will be introduced by conventional transfection techniques into the starting keratinocytes. Suitable techniques include the use of reagents that improve chemical permeability, electroporation, and the like. After transfection, the keratinocytes will be screened based on antibiotic resistance to identify those cells which have received the transfected DNA. The transfected cell lines will be further screened to confirm that stimulation of the keratinocytes results in expression of the marker phenotype, e.g. color, fluorescence, or luminescence. The transfected cell lines may be periodically tested over time in order to identify those where the DNA construct has been stably incorporated.

The construction of a suitable recombinant reporter plasmid containing nucleic acid sequences from −326 to +46 of the human IL-2 gene directing transcription of the firefly luciferase gene is described in Durand, et al., *Mol. Cell Biol.* 8:1715–1724 (1988), the disclosure of which is incorporated herein by reference. This plasmid is designated pIL-2-Luc.

d. Measurement of MHC Class II Production

The level of expression of MHC class II proteins on stimulated cells (keratinocytes, Langerhans and other dendritic cells) treated and untreated with the putative modulating agent can also be compared to determine the modulating effectiveness of the putative agent. MHC class II production can be assayed by the methods described below.

Stimulation of MHC Class II Expression

Keratinocytes express and macrophages and B lymphocytes increase expression of surface MHC class II molecules when activated, for example by γ-interferon.

(1) Direct Measurement of MHC Class II Protein Expression

(a) FACS Analysis

MHC class II expression on the cell surface can be monitored by fluorescence activated cell sorter (FACS) analysis by staining cells directly with anti-MHC class II antibodies conjugated with fluorochromes or indirectly via a secondary antibody that binds the anti-MHC antibody wherein the secondary antibody is fluorochrome-conjugated. Unconjugated or fluorochrome-conjugated anti-MHC class II monoclonals are also readily available commercially, for example from Becton-Dickinson (San Jose, Calif.), Sera-Lab (England), Dako Corp. (Carpinteria, Calif.), Coulter Cytometry (Hialeah, Fla.) and others. Methods of conjugating fluorochromes to immunoglobulins and staining cells for FACS analysis are well known immunological lab procedures and are described for example in Johnstone, A. and Thorpe, R. IMMUNOCHEMISTRY IN PRACTICE (Blackwell Scientific Publications, Boston, 1982) or in Harlow and Lane, ANTIBODIES A LABORATORY MANUAL, Chapters 9 and 10, (Cold Spring Harbor Laboratory, Cold Spring Harbor, N.Y., 1988). The fluorochromes commonly used are rhodamine, fluorescein, phycoerythrin (PE) and Texas red. Typically, the isothiocyanate derivatives of fluorescein and rhodamine are used.

Briefly, an exemplary procedure for FACS analysis of class II proteins involves the following: cells (e.g. keratinocytes) in suspension are incubated with anti-MHC class II antibody in solution such as PBS or media, at 4° C. for about 20 minutes to 1 hour. The cells are washed to remove unbound antibody. If the MHC antibody is not directly conjugated with fluorochrome, the cells are further incubated in the same manner with a secondary reagent labeled with fluorochrome. The secondary reagent can bind to or is specific for the primary antibody and is typically an anti-isotype antibody. For example, if the primary MHC antibody is a mouse IgG, the appropriate secondary antibody is one which reacts with mouse IgG. Again, unbound antibody is washed off. As negative control, a non-specific antibody of the same isotype as the anti-MHC antibody is used. The treated cells are then passed through a FACS machine which will measure the intensity of the fluorescence which directly correlates with the number of MHC class II molecules detected on the cell surface.

(b–c). Western Blotting and Immunohistochemistry

These procedures have been described supra under Direct Measurement of Cytokine Production, with the exception that the detecting first or primary antibody is specific for MHC class II molecules instead of a cytokine. The anti-MHC class II antibodies can be enzymes such as horseradish peroxidase, alkaline phosphatase or β-galactosidase. For staining tissue sections, fluorochrome labeled antibodies can also be used and the staining visualized under a fluorescence microscope. For Western Blotting, the cells are lysed in detergent to solubilize the MHC class II proteins which are membrane proteins. Appropriate detergents include 1% NP40, deoxycholate and CHAPS. The solubilized class II proteins are isolated for electrophoresis by immunoprecipitation with anti-class II antibodies which are preferably directly coupled to beads such as Staphylococcus protein A-conjugated sepharose beads. Alternatively, immunoprecipitation can be performed using a secondary reagent such as a polyclonal antiserum to the primary antibody, coupled to beads. Immunoprecipitation and immunoblotting procedures are well known in the art and are described in ANTIBODIES A LABORATORY MANUAL, cited above.

(2) Measurement of MHC Class II Gene Expression

The modulating agent may regulate class II protein production at the transcriptional or post-transcriptional level. Therefore examination of transcription provides information on the mechanism of gene regulation by the drug. The following techniques for measuring transcription rates, processing and stability of mRNAs, such as (a) Northern Blotting; (b) in situ hybridization; (c) PCR; (d) ribonuclease protection assays; and (e) nuclear run-on assays have been described supra. The relevant cDNAs, probes for Northern blots and oligonucleotide primers for PCR will be specific to MHC class II gene sequences which can be accessed through the GenBank database. Oligonucleotides can be synthesized on an Applied Bio Systems oligonucleotide synthesizer according to specifications provided by the manufacturer. Total or polyA mRNA is isolated by standard procedures as described in Sambrook et al. MOLECULAR CLONING, A LABORATORY MANUAL, 2nd edition, (Cold Spring Harbor Laboratory, Cold Spring Harbor, N.Y., 1989.)

2. In vivo Models

Animal models that are widely viewed to reflect human skin disorders and to have predictive ability in assessing the efficacy of various treatments for these disorders can be utilized to evaluate the procedures described herein.

Various animal models have been developed for known irritant contact dermatitis and allergic contact dermatitis. The majority of these models employ mice or rats, e.g., hairless mice or Balb/c mice. However, a new hairless strain of guinea pig has been shown to provide a good alternative for investigating both cutaneous pharmacology and delivery. See MODELS IN DERMATOLOGY, Maibach and Lowe (eds.) Basel, Karger (1989), which is incorporated herein by reference. Typically, these models involve either the topical or systemic administration of a known irritant (e.g., sodium lauryl sulfate) or allergen (e.g., poison ivy antigen, urushiol) to the animal. A specific treatment regimen can be applied prior to the irritant or allergen challenge, concurrently with, and/or subsequent to the challenge.

Several accepted animal models for skin disease are known, each useful to study different aspects of skin disease, for example, immediate-hypersensitivity reaction, delayed-type hypersensitivity reaction, non-immunologic contact urticaria, and the like. See NON-STEROIDAL ANTI-INFLAMMATORY DRUGS: PHARMACOLOGY OF THE SKIN, Henby and Lowe (eds.), Basel, Karger (1989). With respect to skin irritation models in animals, inflammation and hyperplasia can be induced by topical application of a phorbol ester such as 12-O-tetradecanoylphorbol-13-acetate (TPA) and delayed allergic type contact hypersensitivity can be induced using dinitrochlorobenzene (DNCB) as described in Diezel, et al., *J. Invest. Derm.,* 93:2 p. 322 (1989), which is incorporated herein by reference. Further, compromised skin barrier can be modeled by topical acetone treatment. TPA causes epidermal inflammation and hyperplasia by activating protein kinase C, a key regulator of epidermal growth and inflammation. The pathophysiologic alterations to the skin induced by TPA bear many similarities to the pathophysiologic alterations observed in psoriatic skin. Skin challenged with DNCB several days after sensitization has been observed to exhibit immunologic reactions similar to those observed in clinical cases of allergic contact dermatitis. Acetone treatment of the skin is known to cause physiologic alterations as a result of disruption of the stratum corneum barrier. Such alterations are commonly observed in skin diseases.

In addition to the use of normal mice where skin inflammation is induced via topical application of a specific stimulating agent, relevant skin disease model can also be developed in immune-compromised mice such as athymic nude mice (See Fogh J. et al. THE NUDE MOUSE IN EXPERIMENTAL AND CLINICAL RESEARCH, Academic Press, 1982) and in severe combined immune-deficient (SCID) mice (See Hendrickson Z. A. "The SCID Mouse: Relevance as an Animal Model System for Studying Human Disease," *Am. J. Pathology,* 143:1511–1522, 1993). In these immune-compromised, or immune-deficient mice, excised psoriatic lesional skin is transplanted to the back of the animal. Once healed completely, these xenografts can be used to model psoriasis in man. Similar approach can be applied to the development of other skin diseases, as well as infections.

The most common model for various skin cancers relies on the administration of a cancerous cell line or the implantation of cancerous tissue onto the athymic mouse or SCID mouse. The compromised immune system of this animal will allow the development of cancers or tumors, often on the animal's back, for testing the efficacy of a regimen for treating cancer.

Traditionally, different aspects of wound healing, such as angiogenesis, wound contraction, and connective tissue rearrangement, have been investigated using in vitro and in vivo models. See CLINICAL AND EXPERIMENTAL APPROACHES TO DERMAL AND EPIDERMAL REPAIR: NORMAL AND CHRONIC WOUNDS, Barbul et al. (eds.), Wiley-Liss (1991), which is incorporated herein by reference.

B. Methods for Modulating Inflammatory/Immune Conditions or TNF-Mediated Response 1. Chemical Methods a. TNF Inhibitors In one aspect, the present invention provides methods for treating pathological conditions mediated by TNF production in a mammal using pharmacological agents to regulate the formation, release and biological reactions of TNF and other proinflammatory cytokines or other immunomodulatory substances. The pharmacological agents which are useful in this aspect of the invention are from a broad range of agents known in the literature for other diverse activities. The known activities have lead to the agents being classified as calcium channel blockers, diuretics, antidiarrheals, phosphodiesterase inhibitors and β-agonists. We have now discovered that within each of these groups are representative members which inhibit TNF production and which are now identified as TNF inhibitors by the screening methods described herein. Thus, the methods of treatment provided by the present invention use those calcium channel blockers, diuretics, antidiarrheals, phosphodiesterase inhibitors and β-agonists which also inhibit TNF production.

The following discussion of chemical classes, each of which contain members useful in the present invention, is not meant to be limiting to those members.

One group of pharmacological agents which are useful in the present invention are the calcium channel blockers. Calcium channel blockers or calcium antagonists are compounds that affect intracellular calcium ion concentration and the physiological action of calcium in the cell. There are two main classes of calcium channels, i.e., the voltage-gated and the ligand-gated calcium channels (see Hurwitz L. et al. CALCIUM CHANNELS: THEIR PROPERTIES, FUNCTIONS, REGULATION, AND CLINICAL RELEVANCE, CRC Press, 1991). Based on the degree of depolarization required to activate the channel, the voltage-gated calcium channel class can be further divided into high-threshold (including L-, N- and P-channels) or low-threshold (T-channel) channels. On the other hand, the ligand-gated calcium channels are regulated by specific ligand such as cAMP, binding to the receptor. There are other calcium permeable channels that are not sensitive to the selective calcium channel blockers, which there are no known physiological regulatory mechanism.

Calcium channel agonists and antagonists thus, can be classified based on their binding to a specific site of a channel which has multiple binding site (e.g. L-channel) or based on their respective chemical structures. The three largest classes of L-channel blockers are benzoacetonitriles such as verapamil (see, e.g. WO91/02497 to Sharpe, et al., which is incorporated herein by reference), benzothiazepinones such as diltiazem [CAS-42399-41-7], and 1,4-dihydropyridines such as nifedipine [CAS-21829-25-4] where each has their respective binding site on the L-channel. For verapmil, the best known structural analogs are gallopamil [CAS-16662-47-8], methoxyverapamil, tiapamil and devapamil; dihydropyridine derivatives include nifedipine, nivaldipine, nimodipine, nicardipine, isradipine, amlodipine, nitrendipine, felodipine and nisoldipine (see, e.g. Bacon et al. (1989) *Biochem. Biophys. Res. Comm.,* 165:349–354; and WO 90/09792 to Granstein, et al., both of which are incorporated herein by reference). Another class of L-channel blockers are the 1,3-diphosphonates, represented by belfosodil. Other L-channel blockers that do not conform into the three structural classes described above are McN6186-11, MDL 12,330 A, trans-diclofurine, tetrandrine, HOE 166, SR-7037, SR 33557 and fluspirilene. Compounds with T-channel activity include amiloride, dimethadione, felodipine, cinnarizine, tetramethrin, phenytoin, ethosuximide, amiodarone (see, THE MERCK INDEX, 11th Ed. (Merck & Co. 1989), which is incorporated herein by reference). Compounds with calcium channel blocking properties secondary to other activities includes pimozole, diazopam, cyproheptadine, imipramine, phenobarbital, benextramine, etc., (see, Hurwitz, L., et al., supra, pages 195–249, which are specifically incorporated herein by reference). Still other calcium channel blockers include piperazine derivatives such as cinnarizine, flunarizine, and lidoflazine; and others such as bencyclane, etafenone, and perhexiline; N,N-diacylpiperazines such as described in U.S. Pat. No. 5,292,726 to Wallace, et al.; morpholine and thiomorpholine tachykinin receptor antagonists, such as described in EP 577,394 to Dorn, et al.; isopetasin and oxopetasin, see, DE 4,208,300 to Brune; conotoxin peptides, e.g., conotoxin GVIA and ω-conotoxin MVIIA as described in GB 2,262,886 to Bond, et al.; 5-hydroxy-furanones, see, U.S. Pat. No. 5,171,863 to Garst, et al.; 1,2-dithiole-3-thiones, see, EP 576,619 to Burgot, et al.; monolide, see Wheeler, et al., *J. Biol. Chem.* 262(14):6531–6538 (1987). Each of the above-cited references is incorporated herein by reference.

Some of the most common calcium channel blockers which are useful in the present invention include, in addition to verapamil, e.g., Etafenone (1-Propanone, 1-[2-[2-(diethylamino)ethoxyphenyl]-3-phenyl-), [CAS-90-54-0], Cinepazide maleate (Piperazine, 1-[2-oxo-2-(1-pyrrolidonyl)ethyl]-4-[1-oxo-3-(3,4,5-trimethyoxylphenyl)-2-propenyl]-, (Z)-2-butenedioate (1:1)), [CAS-26328-04-1), Trapidil ([1,2,4] Triazolo[1,5-a]pyrimidin-7-amine, N,N-diethyl-5-methyl), [CAS-15421-84-8], Diltiazem (1,5 - Benzothiazepin4(5H)-one, 3-(acetyloxy)-5-[2-(dimethylamino)ethyl]-2,3-dihydro-2-(4-methoxyphenyl)-, (2S-cis)-[CAS-42399-41-7 and 33286-22-5], Dilazep (Benzoic acid, 3,4,5-trimethoxy-, (tetrahydro-1H-1,4-diazepine-1,4(5H)-diyl)di-3,1-propanediyl ester [CAS-35898-87-4], Lidoflazine (1-Piperazineacetamide, 4-[4,4-bis(fluophenyl)butyl]-N-(2,6-dimethylphenyl), [CAS-3416-26-0], Nifedipine (4-2'-nitrophenyl)-2,6-dimethyl-3,5-dicarbomethyl-1,4-dihydropyridine) [CAS-21829-25-4], Fantoferone (Benzeneethyanamide, 3,4-dimethoxy-N-methyl-N-[3-[4-[[2-(1-methylethyl)-1-indolizinyl]sulfonyl] phenoxy]propyl] [CAS-114432-13-2], KT-362 (1,5-Benzothiazepine, 5-[3-[[2-dimethoxyphenyl]ethyl]amino]1-oxopropyl]-2,3,4,5-tetrahydro-, (E)-2-butenedioate(1:1), [CAS-105394-80-7], WK-269 (3-(3,4-dihydro-2H-benzo(b) pyranyl)-5-methyl-1,4-dihydro-2,6-dimethyl4-(2,3-dichlorophenyl)-pyridine-3,5-dicarboxylate), KW-3407 (1,2-Ethanediamine, N'-(5,11-dihydro-7-methoxy[1] benzoxepino[3,4-b]pyridin-5-yl)-N,N-diethyl-, (E)-2-butaenedioate (2:3) [CAS-115750-37-3], SR-33805A (3-isopropyl-2-[4-[3-[N-[2-(3,4-dimethoxyphenyl)ethyl]-N-methylamino]propoxy]phenylsulfonyl]-1-methylindole oxalate) Felodipine (3,5-Pyridinedicarboxylic acid, 4-(2,3-dichlorophenyl)-1,4-dihydro-2,6-dimethyl-, ethyl methyl ester [CAS-72509-76-3], Ranolazine (1-Piperazineacetamide, N-(2,6-dimethylphenyl)-4-[2-hydroxy-3-(2-methoxyphenoxy)propyl]-, (±) [CAS-95635-55-5 and 95635-56-6], Isradipine (3,5-Pyridinecarboxylic acid, 4-(4-benzofurazanyl)-1,4-dihydro-2,6-dimethyl, methyl 1-methylethyl ester) [CAS-75695-93-1 and 88977-22-4], Iacidipine (3,5-Pyridinedicarboxylic acid, 4-[2-[3-(1, 1-dimethylethoxy)-3-oxo-1-propenyl]phenyl]-1,4-dihydro-2,6-dimethyl-, diethyl ester, (E)-) [CAS-103890-78-4], Nexopamil, NKY-722 (3,5-Pyridinedicarboxylic acid, 1,4-dihydro-2,6-dimethyl-4-(3-nitrophenyl)-, 2,2-dimethyl-3-[4-(2-propenyl)-1-piperazinyl]propyl methyl ester, dihydrochloride [CAS-117241-46-0], Barnidipine (3,5-Pyridinedicarboxylic acid, 1,4-dihydro-2,6-dimethyl-4-(3-nitrophenyl)-, methyl 1-(phenylmethyl)-3-pyrrolidinyl ester, [S-(R*,R*)]-) [CAS-104713-75-9, 104757-53-1 and 71863-56-4], Amidipin (Acetamide, 2-(diethylamino)-N-(6,11-dihydrodibenzo[b,e]thiepin-11-yl)-, S,S-dioxide) [CAS-90405-00-8], Bepridil (1-Pyrrolidieneethanamine, b-[(2-methylpropoxy)methyl]-N-phenyl-N-(phenylmethyl)), [CAS-64706-54-3, 74764-40-2, and 74764-74-3) SA-3212 (2H-1,4-Benzothiazin-3(4H)-one, 2-[2-[3-[[2-(1,3-benzodioxol-5-yloxy)ethyl]methylamino]propoxy]-5-methoxyphenyl]-4-methyl-, (S)-, (E)-2-butenedioate (1:1)) [CAS-116476-17-6] RWJ-22726 (N-benzyl-N-methylaminoethyl 10-(2,3-dichlorophenyl)-3,4,5,6,7,10-hexahydro-8-methyl-1,1-dioxo-2H-thiacyclo-octeno[3,2-b] pyridinecarboxylate), SR-33805 (2-n-butyl 3-[4-(3-di-n-butylamino-propoxy)benzol]5-methylsulphonamidobenzofuran HCL), AJ-2615 (1-Piperazinebutanamide, N-(6,11-dihydrodibenzo[b,e] thiepin-11-yl)4-(4-flurophenyl)-, (Z)-2-butenedioate (1:1)) [CAS-103379-03-9], Benidipine (3,5-Pyridinedicarboxylic acid, 1,4-dihydro-2,6-dimethyl-4-(3-nitrophenyl)-, methyl 1-(phenylmethyl)-3-piperidinyl ester, (R*,R*)-(±)-) [CAS-105979-17-7 and 81599-74-5], CD-832, CS-905 (3,5-Pyridinedicarboxylic acid, 2-amino-1,4-dihydro-6-methyl-4-(3-nitrophenyl)-, 3-[1-(diphenylmethyl)-3-azetidinyl] 5-(1-methylethyl)ester, (±)-) [CAS-123524-52-7], Dopropidil (Pyrrolidine, 1-[1-[(2-methylpropoxy)methyl]-2-[[1-(1-propynyl)cyclohexyl]oxy]ethyl]) [CAS-79700-61-1 and 117241-47-1], Elgodipine (3,5-Pyridinedicarboxylic acid, 4-(1,3-benxodioxol-4-yl)-1,4-dihydro-2,6-dimethyl-, 2-[[(4-flurophenyl)methyl]methylamino]ethyl 1-methylethyl ester, (±)) [CAS-121489-04-1], Fasudil (1H-1,4-Diazepine, hexahydro-1-(5-isoquinidinolinylsulfonyl) [CAS-103745-39-7 and 1056284-07-7], Flosatidil (Carbamic acid, [2-(dimethylamino)ethyl][2-[[2-(methylthio)phenyl][[3-(triofluoromethyl)phenyl]methyl]amino]-2-oxoethyl]-, 2-methylpropyl ester) [CAS-113593-34-3 and 113593-35-4) Gallopamil (N-Benzeneacetonitrile, a-[3-[[2-(3,4-dimethoxyphenyl)ethyl]methylamino]propyl]-3,4,5-trimethoxy-a-(1-methylethyl)) [CAS-16662-47-8], LR-A/ 113 (cis-(+)-3-aceto-2,3-dihydro-5-[2-(N-isopropyl-N-methyl-N-methyl-amino)ethyl]-2-(4-methoxyphenyl)-1,5-benzothiazepin4-(5H)-one HBr), LU-49938 ((2(S)-5-[N-methyl-N-(n-hexyl)]amino-2-(3,4,5-trimethoxy-phenyl)-2-idopropyl-valeronitrile HCL), NH-2716, Nicardipine (3,5-Pyridinedicarboxylic acid, 1,4-dihydro-2,6-dimethyl-4-(3-nitrophenyl)-, methyl 2-[methyl(phenylmethyl)amino]ethyl ester) [CAS-55985-32-5 and 54527-84-3], Nictiazem (3-Pyridinecarboxylic acid, 5-[2-(dimethylamino)ethyl]-2,3, 4,5-tetrahydro-2-(4-methoxyphenyl)-4-oxo-1,5-benzothiazepin-3-yl ester, cis-(+)) [CAS-95058-70-1 and 109545-09-7], Semotiadil (2H-1,4-Benzodiazepin-3(4H)-one, 2-[2-[3 [[2-(1,3-benzodioxol-5-yloxy)ethyl] methylamino]propoxy]-5-methoxyphenyl]4methyl-, (R), [CAS-118476-13-2 and 116476-14-3], Rec 15-2375 (3,5-Pyridinedicarboxylic acid, 1,4-dihydro-2,6-dimethyl-4-(3-nitrophenyl)-, 2-[3,3-diphenylpropyl)methylamino]-1,1-dimethylethyl methyl ester [CAS-100427-26-7], Ro-10-5976 (Acetic Acid, methoxy-, 2-[2-[[3-(1H-benzimidazole-2-yl)propyl]methylamino]ethyl]-6-fluoro-1,2,3,4-tetrahydro-1-(1-methylethyl)-2-naphthalenyl ester, dihydrochloride, (1S-cis)-[CAS-11666-63-8], WK-269 3-(3, 4-dihydro-2H-benzo(b)pyranyl)-5-methyl-1,4-dihydro-2,6-dimethyl-4-(2,3-dichlorophenyl)-pyridine-3,5-dicarboxylate), YM-430 (4((S)-2-hydroxy-3-phenoxypropylamino) butyl methyl-2,6-dimethyl ((s)4-(m-nitrophenyl))-1,4-dihydropyridine-3,5-dicarboxylic acid), Belfosdil (Phosphonic Acid, [2-(2-phenoxyethyl)-1,3-propanediyl]bis-, tetrabutyl ester) [CAS-103486-79-9], Benidipine (3,5-Pyridinedicarboxylic acid, 1,4-dihydro-2,6- dimethyl-4-(3-nitrophenyl)-, methyl 1-(phenylemthyl)-3-piperidinyl ester, (R*, R*)-(±)-) [CAS-105979-17-7 and 91599-74-5], Brinazarone (Methanone, [4-[3-[(1,1-dimethylethyl)amino]propoxy]phenyl][2-(1-methylethyl)-3-indolizinyl]-) [CAS-89622-90-2], CD-349 (3,5-Pyridinedicarboxylic acid, 1,4-dihydro-2,6-dimethyl-4-(3-nitrophenyl)-, 2-(nitrooxy)propyl 3-(nitrooxy)propyl ester) [CAS-88594-08-5], Cilnidipine (3,5-Pyridinedicarboxylic acid, 1,4-dihydro-2,6-dimethyl-4 -(3-nitrophenyl)-, 2-methoxyethyl 3-phenyl-2-propenyl ester) [CAS-102106-21-8], Clentiazem Maleate (1,5-Benzothiazepin-4(5H)-one, 3-(acetyloxy)-8chloro-5-[2-(dimethylamino)ethyl]-2,3-dihydro-2-(4-methoxyphenyl)-, (2S-cis)-, (Z)-2-butenedioate (1:1)) [CAS-96128-92-6], CS-905 (3,5-Pyridinebicarboxylic acid, 2-amino-1,4-dihydro-6-methyl-4-(3-nitrophenyl)-, 3-[1-(diphenylmethyl)-3-azetidinyl] 5-(1-methylethyl)ester, (±)) [CAS-123524-52-7], Efonidipine (3-Pyridinecarboxylic acid, 5-(5,5-dimethyl-1,3,2-dioxaphosphorinan-2-yl)-1,4-dihydro-2,6-dimethyl-4-(3-nitrophenyl)-, 2-(phenyl(phenylmethyl)amino)ethyl ester, P-oxide) [CAS-111011-63-3, 111011-53-1 and 111011-76-8), Furnidipine (ethyl 2-[4-(Phenylsulfonyl)-1-piperidinyl] ethyl 1,4-dihydro-2,6-dimethyl-4-(2-nitrophenyl)-3,5-pyridinedicarboxylate) [CAS-138661-03-7], KP-873 ((±)-2-(4-diphenylmethyl-1-piperizinyl)ethyl-methyl-1,4-dihydro-2,6-dimethyl-4-(3-ethynylphenyl)-3,5-pyridinedicarboxylate 2HCL), Minidipine (3,5-Pyridinedicarboxylic acid, 1,4-dihydro-2,6-dimethyl-4-(3-nitrophenyl)-, 2-[4-(diphenylmethyl)-1-piperizinyl]ethyl methyl ester) [CAS-89226-50-6 and 89226-75-5], Oxodipine (3,5-Pyridinedicarboxylic acid, 4-(1,3-benzodioxol-4-yl)-1,4-dihydro-2,6-dimethyl-, ethyl methyl ester) [CAS-90729-41-2], Panolidipine (3,5-Pyridinedicarboxylic acid, 4-(2-fluoro-5-nitrophenyl)-1,4-dihydro-2,6-dimethyl-, 2,2-dimethyl-3-[methyl(phenylmethyl)amino]propyl methyl ester) [CAS-96515-73-0 and 96515-74-1], Pranidipine (3,5-Pyridinedicarboxylic acid, 1,4-dihydro-2,6-dimethyl-4(3-nitrophenyl)-, methyl 3-phenyl-2-propenyl ester, (E)) [CAS-99522-79-9], SM-6586 (methyl 1,4-dihydro-2,6-dimethyl-3-[3-((N-methyl)aminomethyl)-N-(phenylmethyl)-1,2,4-oxadiazol-5-yl]-4-(3-nitrophenyl)pyridine-5 carboxylate), SQ-33351 ([3R-[1(S*), 3a, 4a]]-3-(acetyloxy)-1,3,4,5-tetrahydro-4-(4-methoxyphenyl)-1-(2-pyrrolidinylmethyl)-6-(trifluoromethyl)-2H-1-benzazepine-2-one HCL) [CAS-128509-69-3], TJ-15, Vintoperol (21-Nor-1,14-secoeburnamenin-20-ol, 14,15-dihydro, (3a)-(±)) [CAS-58451-76-6], Flunarizine (Peperizine, 1-[bis(4-fluorophenyl)methyl]-4(3-phenyl-2-propenyl)-, (E)) [CAS-52468-60-7], Amlodipine (3,5-Pyridinedicarboxylic acid, 2-[(2-aminoethoxy)methyl-4-(2-chlorophenyl)-1,4-dihydro-6-methyl-, 3-ethyl 5-methyl ester [CAS-88150-47-4, and 111470-99-6], L-Anipamil ((−)a-dodecyl-3-methoxy-a-[3-[2-(3-methoxyphenyl)ethyl]methylamino] propylbenzeneacetanitrile), Nivadipine (3,5-Pyridinedicarboxylic acid, 2-cyano-1,4-dihydro-6-methyl4-(3-nitrophenyl)-, 3-methyl 5-(1-methylethyl)ester) [CAS-75530-68-6], AHR-16462B (Piperidine, 4-[bis(4-fluorophenyl)methyl]-1-(2-naphthalenylmethyl)-, hydrochloride) [CAS-134142-91-9], NB-818 (3,5-Pyridinedicarboxylic acid, 2-[[(aminocabonyl)oxy]methyl]-4-(2,3-dichlorophenyl)-1,4-dihydro-6-methyl-5-methyl 3-(1-methylethyl) ester) [CAS-94739-29-4], S-312-d (Thieno[2,3-b]pyridine-5-carboxylic acid, 4,7-dihydro-6-methyl-3-(2-methylpropyl)-4-(3-nitrophenyl)-, methyl ester, (+)) [CAS-120056-57-7].

In addition, many antianginals, cerebral, coronary and peripheral vasodilators, diuretics (such as the benzothiadiazine derivatives, pteridines, and sulfonamide derivatives), antidiarrheals such as loperamide (4-(p-chlorophenyl)-4-hydroxy-N,N-dimethyl-α,α-diphenyl-1-piperidine butyramide HCL [CAS-53197-11-6 and 34552-83-5]), fluperamide and diphenoxylate, and their derivatives (see, e.g., U.S. Pat. Nos. 5,116,847, 2,898,340, 4,443,460, 3,081,303, 3,585,204 and 4,853,387, all of which are incorporated herein by reference) and other opiate receptor antagonists, and antihypertensives possess pharmacological properties suitable for use in the present invention. Surprisingly, loperamide was found to suppress TNF production in stimulated THP-1 cells in a dose-dependent manner, suppressing TNF production by about 42% at a concentration of 10 μM. Loperamide (10 μm) also showed effectiveness in suppressing TNF production in stimulated RAW cells (62% inhibition at 10 ng/mL LPS), and TPA-induced skin swelling response in mice.

Preferred compounds useful in the present invention include the loop diuretics and thiazides. Loop diuretics, e.g., furosemide, ethacrynic acid and bumetanide, are known to affect kidney function by blocking the re-absorption of sodium chloride (NaCl) in the medullary and cortical portions of the thick ascending limb of Henle's loop; thereby, reducing the osmotic gradient in the renal medulla and impairing the concentrating and diluting capacities of the kidney. Current clinical indications for the use of loop diuretics include hypertension, chronic congestive heart failure, acute pulmonary edema, nephrotic syndrome, chronic renal failure, chronic liver disease, brain edema and hyponatremic states. Thiazides (e.g., chlorthalidone, quinethazone, metolazone, indapamide, chlorothiazide, hydrochlorothiazide, bendroflumethiazide, cyclothiazide, hydroflumethiazide methychlothiazide, polythiazide, and trichloromethiazide) were among the first diuretic drugs discovered in the late 1950s. The mode of action and clinical indications of these drugs are substantially similar to the loop diuretics. See, *Drug Evaluations* (Subscription), Vol. II: "Renal-Urologic Drugs", American Medical Association (Winter 1993).

Certain diuretics have unexpectedly demonstrated anti-inflammatory properties; furosemide decreased TNF production by about 49% in LPS (10 ng/ml)-stimulated RAW cells. Another class of preferred compounds is the potassium-sparing diuretics, such as spironolactone, triamterine, etozolin (Acetic Acid, [3-methyl-4oxo-5-(1-piperidinyl02-thiazolidinylidene]-, ethyl ester [CAS-73-09-6]) and amiloride. Generally, these compounds are known to interfere with sodium re-absorption in the cortical collecting duct of the kidney. However, these different compounds achieve diuresis through diverse mechanisms. Triamterine and amiloride interfere with electrolyte transport. Spironolactone, on the other hand, is an competitive antagonist of aldosterone. Spironolactone has also been employed as a treatment for hirsutism (see, Re 32,112 to Shapiro) and acne (see, U.S. Pat. No. 4,543,351 to Messina). However, spironolactone has been found unexpectedly to possess anti-inflammatory properties. As described below, spironolactone was found to decrease LPS-stimulated TNF production in THP-1 cells by 46%.

Sodium channel antagonists also can be used in conjunction with the present invention. Such antagonists include alprafenone ((R,S)-1-(4-methylphenyl)-3-[3'-(2-hydroxy-3-tert-pentylaminopropoxy)-4'-methoxyenyl]-1-propanone HCL); bidisomide (1-Piperidinebutanamide, a-[2-[acetyl-(1-methylethyl)amino]ethyl]-α-(2-chlorophenyl), (±)) [CAS-116078-65-0]; bisaramil (benzoic acid, 4-chloro-, 3-methyl-7-ethyl-3,7-diazabicyclo[3.3.1]non-9-yl ester, syn)[CAS-89194-77-4 and 96480-44-3]; ceracaine (1-(2-methocyphenoxy)-2,3-bis(2-diethylaminoethoxy)propane dicitrate); cibenzoline (1-H-imidazole, 2-(2,2-diphenylcyclopropyl)-4,5-dihydro) [CAS-53267-01-9]; CV-6402 (2,2'-[(2-amino-ethyl)imino]diethanol bis (butylcarbamate) 2HCL); EGIS-3966 (Cyclohexanone, 2-(phenylmethylene)-[3-[bis(1-methylethyl)amino]-2-hydroxypropyl]oxime, (E,E)-(±)-, (E)-2-butendioate (12:1)) [CAS-135338-31-7]; flecainide acetate (benzamide, N-(2-piperidinylmethyl)-2,5-bis(2,2,2-trifluoroethoxy)-monoacetate) [CAS-54143-56-5 and 54143-55-4]; FPL-13210 ((R*, S*)-(±)-2-(2-bromo-α-hydroxybenzyl)-5-(dimethylamino)-N,N-dimethyl-2-phenylpentanamide); GYKI-38233 (Hydrazinecarboximidamide, 2-(2,6-dimethylphenyl)-N,N-dimethyl-monohydrochloride) [CAS-100751-82-4; Hoe-694; indecainide (9H-fluorene-9carboxamide, 9-[3-[(1-methylethyl)amino]propyl]) [CAS-74517-78-5 and 73681-12-6]; ipazilide (1H-pyrazole-1-acetamide, N-[3-(diethylamino)propyl]-4,5-diphenyl-) [CSA-115436-73-2 and 1154436-74-3]; LG-6-101 (1-propanone, 1-[3-[2-methoxy-3-[(2-methylpropyl)amino] propoxy]-4-methyl-2-thienyl]-3-phenyl-, hydrochloride) [CAS-132798-26-6]; LG-6-102 (1-propanone, 1-[2-[2-methoxy-3-(propylamino)propoxy]phenyl]-3-phenyl-, hydrochloride) [CAS-132798-30-2]; moracizine (Carbamic acid, [10-[3-(4-morpholinyl)-1-oxopropyl]-10H-phenothiazin-2-yl]-, ethyl ester) [CAS-31883-05-3 and 29560-58-5]; Org-7797 (Estra-1,3,5(10)-triene-3,16-diol, 17-(methylamino)-(16a, 17b)-(Z)-2-butenedioate (1:1) (salt)) [CAS-80177-51-1]; PD-85639 (N-[3-(2,6-dimethyl-1-piperidinyl)propyl]-α- phenylacetamide); penticainide (2-pyridineacetamide, α-[2-bis(1-methylethyl)amino] ethyl]-α-(2-methoxylpropyl)) [CAS-78833-03-1]; Pilsicainide (1H-Pyrrolizine-7α(5H)-acetamide, N-(2,6-dimethylphenyl)tetrahydro) [CAS-88069-67-4 and 88069-49-2]; pirmenol (2-pyridinemethanol, α-[3-(2,6-dimethyl-1-piperidinyl)propyl]-α-phenyl-cis-(±)) [CAS-68252-19-7, and 61447-94-9]; propafenone (1-propanone, 1-[2-[2-hydroxy-3-(propylamino)propoxy]phenyl]-3-phenyl-[CAS-54063-53-5]; quinidine sulfate (cinchonan-9-ol, 6'-methoxy-, (9S)-, sulfate (2:1) 9-salt)) [CAS-50-54-4]; recainam (Urea, N-(2,6-dimethylphenyl)-N'-[3-[(1-methylethyl)amino]propyl]-[CAS-74738-24-2, 74752-07-1, and 74752-08-2); RO-22-9194 ((±)-2-amino-N-(2,6-dimethylphenyl)-N-[3-(3-pyridinyl)propyl]propanamide 2HCL); ropitoin (2,4-imidazolidinedione, 5-(4-methoxyphenyl)-5-phenyl-3-[3-(4-phenyl-1-piperidinyl) propyl]) [CAS-56079-81-3 and 56079-80-2]; RS-2135 ((3aR, 12R, 12aR, 12bS)-12-amino-2,3,3a,4,11,12,12a,12b-octahydro-10-hydroxyisoquino[2,1,8-lmacarbazol-5-1(H)-one HCL 1.5 hydrate) [CAS-133775-36-7]; S-1389 (2-propanol, 1-[3,6-dichloro-2-[1-(1H-imidazol-1-yl) ethenyl]phenoxyl]-3-[(1-methylethyl)amino-, monohydrochloride) [CAS-94899-83-9]; α-carpertide (Atriopeptin-21 (rat), N-L-arginyl-8-L-methionine-21a-L-phenylalanine-21b-L-arginine-21c-L-tyrosine) [CAS-95896-08-5]; anaritide (atriopeptin-21, N-L-arginyl-8-L-methionine-21a-L-phenylalanine-21b-L-arginine-21c-L-tyrosine) [CAS-95896-08-5 and 85637-73-6]; CRE-10904 (phenol, 2-[2-(4fluorophenoxy)ethyl]) [CAS-132194-67-3]; CV-2198 (1-benzyl-4-chloro-2-(4-dimethylamino) phenylimidazole-5-acetic acid); furosemide, (benzoic acid, 5-(aminosulfonyl)-4-chloro-2-[(2-furanylmethyl)amino]- [CAS-54-31-9]; isogladine (1,3,5-triazine-2,4-diamine, 6-(2,5-dichlorophenyl)) [CAS-57381-26-7, 57381-33-6, adn 57381-28-9]; M-17055 (7-chloro-2,3-dihydro-1-(2-methylbenzoyl)-4(1H)-quinolinone-4-oxime-O-sulfonate potassium salt) [CAS-114417-20-8]; MD-39-AM (4-Anilino-2-(methylthio)pyrido[2,3-d]pyrimidine) [CAS-72564-74-0]; metipamide (Benzoic acid, 3-(aminosulfonyl)-4-chloro-, 2-methyl-2-phenylhydrazine [CAS-85683-41-6]; piretanide benzoic acid, 3-(aminosulfonyl)-4-phenoxy-5-(1-pyrrolidinyl)) [CAS-55837-27-9]; α-carperitide (Atriopeptin-21, N-L-arginyl-8-L-methionyl-21a-L-phenylalanine-21b-L-arginine-21c-L-tyrosine [CAS-95896-08-5]; R-56865 (2-benzothiazolamine, N-[1-[4-(4-fluorophenoxy)butyl-4-piperidinyl]-N-methyl) [CAS-104606-13-5]; N-1197 (6,10,14,18,22,26,30,34,38-Tetracontanonaenamide, 3,7,11,15,19,23,27,31,35,39-decamethyl) [CAS-93790-39-7] and analog N-1509 (the decaenamide [CAS-93772-48-6]; Carsatrin (4-[bis(4-fluorophenyl)methyl-α-[(5H-purin-6-ylthio)methyl]-piperazineethanol) [CAS-125363-87-3]; and BDF-9148 (4-[3'-1-(diphenylmethyl)-azetidine-3-yl(oxy)-2'-hydroxypropoxy]-1H-indole-2,-ontrile) [CAS-120838-81-5].

Agents that elevate intracellular cyclic AMP (cAMP) levels also have been demonstrated to have a significant suppressive effect on TNF release. See Kunkel et al. (1986) *Biochem. Biophys. Res. Commun.* 137:404–410. Using an in vitro culture of mouse peritoneal macrophages, $PGE_2$ was found to effectively suppress lipopolysaccharide (LPS)-stimulated TNF production. The increase in intracellular cAMP levels produced upon interaction of $PGE_2$ with its receptor was postulated to be the mechanism accounting for the observed inhibitory effect. In additional studies, $PGE_2$ was found to suppress TNF expression at the levels of both transcription and translation. See Kunkel et al. (1988) *J. Biol. Chem.* 263:5380–5384 and Spengler et al. (1989) *Infect. Immunity* 57:2837–2841. Furthermore, this effect was mimicked by dibutyryl cAMP, a nondegradable analog of cAMP, and forskolin, an adenylate cyclase activator, thus confirming the involvement of cAMP in the observed $PGE_2$ inhibitory effect on TNF.

β-Adrenergic agonists and other substances which cause a receptor-mediated activation of adenylate cyclase (both G-protein activators and α-receptor agonists) also can be used to increase intracellular cAMP levels. Commonly used β-adrenergic agonists (or β-agonists) include albuterol, terbutaline, metaproterenol, isotharine, carbuterol, fenoterol, quinterenol, rimiterol, salmefamol, soterenol and tretoquinol (see Goodman and Gilman's THE PHARMACOLOGICAL BASIS OF THERAPEUTICS for additional references). In studies using whole blood and THP-1 cells stimulated with LPS, the β-adrenergic agonists epinephrine and isoproterenol were found to cause a dose-dependent inhibition of TNF release. See Severn et al. (1992) *J. Immunol.* 148:3441–3445. This effect was reversed by β-, but not α-, adrenergic antagonists and was associated with elevated intracellular cAMP levels. Additionally, keratinocytes possess β-adrenergic receptors which mediate an elevation in intracellular cAMP levels upon stimulation with epinephrine, norepinephrine, or isoproterenol. Surprisingly, selected β-agonists also suppress TNF production in THP-1, RAW and keratinocytes.

The net intracellular cAMP level can also be increased by inhibiting the cAMP degradation. To this end, several inhibitors of phosphodiesterases (PDEs), the enzyme that degrades cAMP to 5'-AMP will find use in the methods described herein. Examples of PDE inhibitors include type IV phosphodiesterase inhibitors (the isozyme family specific for cAMP), such as rolipram, RO 20-1724; methylxanthines such as pentoxifylline (a non-specific PDE inhibitor, see, e.g., European Patent Application No. 544,391 A1 to Eitan, et al.), theophylline, theobromine, and isomethylxanthine; pyrrolidinones and phenyl cycloalkane and cycloalkene derivatives, described in PCT publications Nos. WO 92/19594 and WO 92/10190). Surprisingly, RO 20-1724 showed inhibitory activity against TNF and was more effective than non-specific PDE inhibitors such as pentoxifylline.

(1) Selected Isomers of Calcium Channel Blockers

Two of the three major structural classes of calcium channel blockers exist in optically active forms. Verapamil and diltiazem each have at least one optical center and accordingly can be separated into their respective enantiomers to determine the levels and types of activity associated with each. Nifedipine, a dihydropyridine, has a plane of symmetry which bisects the symmetrically substituted dihydropyridine ring and therefore exists as a single isomer. For other dihydropyridine agents which are not symmetrically substituted, optical isomers will exist due to the chirality associated with the C-4 position of the dihydropyridine.

The benzoacetonitriles, (e.g., verapamil and its analogs) are coronary vasodilators with calcium channel blocking activity. Conventionally, verapamil is used predominantly to treat selected cardiac arrhythmias and hypertension in humans. It has also found application in the therapy of ocular hypertension and glaucoma. See U.S. Pat. No. 4,981, 871.

As to their clinical pharmacology, the benzoacetonitriles are calcium ion influx inhibitors (slow-channel blockers or calcium ion antagonists). Their pharmacological effects occur by modulating the influx of calcium ions across the cell membrane of arterial smooth muscle as well as in conductile and contractile myocardial cells. In addition to having effects on the blockade of calcium channels, the benzoacetonitriles appear also to block a-receptors. This may also account for their vasodilatory effect.

The mechanism of action for the calcium channel blockers in their conventional usage as an anti-anginal agent is incompletely understood, but involves at least the following. The agent dilates the main coronary arteries and arterioles and is a potent inhibitor of coronary artery spasm. Also, the agent reduces oxygen utilization by reducing the total peripheral resistance (afterload) against which the heart works.

In addition to being useful in angina, some calcium channel blockers (e.g., verapamil) are used an anti-arrhythmic agents. In particular, verapamil has been found to prolong the refractory period within the atrio-ventricular (AV) node and slows AV conduction. Furthermore, some of the calcium channel blockers have antihypertensive effects because of their ability to decrease systemic vascular resistance.

Verapamil has also been described as an effective agent for lowering intraocular pressure such as occurs in ocular hypertension, and glaucoma. In these conditions, verapamil is typically administered topically to the eye, such as in drops. See, for example, U.S. Pat. No. 4,981,871 to Abelson.

For verapamil, the coronary vasodilatory activity has been attributed primarily to the minus isomer ((−)-verapamil, see Gilman et al. (eds) in GOODMAN AND GILMAN'S: THE PHARMACOLOGICAL BASES OF THERAPEUTICS, 8th Ed., Pergamon Press pp. 816–817 (1990)). Similarly, for diltiazem, vasodilating action is stereospecific for the d-cis isomer (also called the cis-(+) isomer, see Sato, et al., *Arzneimittel-Forsch.* 21:1338 (1971)).

Quite surprisingly, we have now found that calcium channel blockers can inhibit TNF production and can be used for the treatment of pathological conditions mediated by TNF production. Still more surprisingly, we have discovered that anti-inflammatory properties are associated with both isomers of a racemic pair. Thus, a specific optical isomer of a calcium channel blocker can be selected to provide a desired therapeutic benefit while minimizing other pharmacological activities which are typically associated with the other isomer. For example, (+)-verapamil is the less cardiovascularly active isomer of verapamil, yet has now been found to provide inhibition of TNF production which is equivalent to (−)-verapamil. As a result, the use of (+)-verapamil to treat inflammation is not associated with undesirable side effects which have been imputed to either (−)-verapamil or racemic verapamil. For diltiazem, another calcium channel blocker, the minus isomer (as the less cardiovascularly active isomer) will be preferred. However, optimal modulation of TNF production will not always be associated with inhibition of TNF production. For some conditions, such as infection and wound healing, elevated TNF production is beneficial to enhance the body's immune response to fight infections, and to facilitate removal of degenerated tissue and to promote regeneration of newer tissue in the wound healing processes.

Thus in one aspect, the present invention provides methods of treating pathological conditions mediated by TNF production using therapeutically effective amounts of a calcium channel blocker. In, preferred embodiments, for calcium channel blockers having one or more optical centers, a specific optical isomer of the calcium channel blocker is used. The specific optical isomer is preferably the isomer which is the less cardiovascularly active isomer. Alternatively, the specific optical isomer can be selected to provide optimal modulation of TNF production. In other preferred embodiments, the calcium channel blocker is a benzoacetonitrile, a dihydropyridine or a benzothiazepinone, more preferably as a specific optical isomer. Still further preferred are those embodiments in which a benzoacetonitrile, preferably verapamil, is present predominantly as its plus isomer.

In one group of embodiments, the pathological condition is a skin inflammatory condition, preferably psoriasis, atopic dermatitis, UV-induced inflammation, contact dermatitis or inflammation induced by Retin-A. For these conditions, the preferred calcium channel blockers are those described above.

In another group of embodiments, the pathological condition is a systemic inflammatory condition, preferably inflammatory bowel disease, rheumatoid arthritis, cachexia, asthma, Crohn's disease, endotoxin shock, adult respiratory distress syndrome, ischemic/reperfusion damage, graft-versus-host reactions, bone resorption, transplantation or lupus. For the treatment of these TNF-mediated conditions in a mammal, a therapeutically effective amount of a calcium channel blocker is administered to the mammal. As with the more general methods and for the treatment of skin inflammatory conditions, the preferred calcium channel blockers are benzoacetonitriles, dihydropyridines or benzothiazepinones, more preferably as a specific optical isomer. Still further preferred are those embodiments in which a benzoacetonitrile, preferably verapamil, is present predominantly as its plus isomer.

In still another group of embodiments, the pathological condition is multiple sclerosis, diabetes or AIDS, and the method comprises administering to the patient afflicted with one of the conditions, a therapeutically effective amount of a calcium channel blocker. The preferred calcium channel blockers are benzoacetonitriles, dihydropyridines or benzothiazepinones, more preferably as a specific optical isomer. Still further preferred are those embodiments in which a benzoacetonitrile, preferably verapamil, is present predominantly as its plus isomer.

In another aspect, the present invention provides methods of reducing skin adverse reactions associated with the application of transdermal devices to a selected area of the skin, comprising administering to the selected area of the skin an amount of a calcium channel blocker effective to reduce the adverse reaction in conjunction with the application of transdermal devices. The administration of the calcium channel blocker to the skin can be made either prior to, contemporaneously with, or subsequent to the application of the transdermal patch. In preferred embodiments, the calcium channel blocker is a benzoacetonitrile, a dihydropyridine or a benzothiazepinone. In instances in which the calcium channel blocker has at least one optical center, a specific optical isomer is preferred, more preferably either that isomer which is the less cardiovascularly active isomer or the isomer which provides optimal modulation of TNF production. In particularly preferred embodiments, the calcium channel blocker is a benzoacetonitrile, predominantly as its plus isomer, most preferably verapamil, predominantly as its plus isomer.

In yet another aspect, the present invention provides a method of reducing skin sensitization and irritation associated with the iontophoretic delivery of a therapeutic agent, comprising administering a therapeutically effective amount of a calcium channel blocker in conjunction with the iontophoretic delivery of the therapeutic agent. The administration of the calcium channel blocker to the skin can be made either prior to, contemporaneously with, or subsequent to the iontophoretic delivery of the therapeutic agent. In preferred embodiments, the calcium channel blocker is a benzoacetonitrile, a dihydropyridine or a benzothiazepinone. As with the methods associated with the application of a transdermal patch, above, the calcium channel blocker will preferably be a specific optical isomer (when the CCB has at least one optical center). More preferably that isomer is either the less cardiovascularly active isomer or the isomer which provides optimal modulation of TNF production. In particularly preferred embodiments, the calcium channel blocker is a benzoacetonitrile, predominantly as its plus isomer, most preferably verapamil, predominantly as its plus isomer.

In still other aspects of the present invention, methods are provided for the treatment of ocular inflammation in a mammal and for reducing skin sensitization or irritation arising from the use of a cosmetic or skin care product. In each of these methods, an effective amount of a calcium channel blocker is administered to the mammal to reduce the inflammation, sensitization or irritation associated with the condition. Preferred calcium channel blockers are those which have been described above.

For all of the methods above, the formulations, the route of administration, the dosages and schedules for treatment will vary depending on, for example, the particular condition and its severity; the age, weight, and clinical condition of the recipient patient; and the experience and judgment of the clinician or practitioner administering the therapy. More complete discussions are below.

The calcium channel blockers which are useful in the present invention are either commercially available or can be isolated or prepared according to literature methods. Using the Chemical Abstracts Services (CAS) registry numbers provided above for a number of calcium channel blockers, one of skill can locate the appropriate reference materials to isolate or prepare the desired compound. Alternatively, THE MERCK INDEX, 11th Ed. (Merck & Co. 1989), previously incorporated herein by reference, provides references to papers describing the synthesis of many CCBs.

Plus verapamil is an example of an agent used in one preferred embodiment of the invention. However, the invention is not so limited. Verapamil is one example of a basically substituted phenyl acetonitrile compound. See, for example, U.S. Pat. No. 3,261,859 to Dengel, assigned to Knoll, for additional examples. Therein several closely related compounds are disclosed, any of which are applicable to the invention. Because it has been intensely studied clinically and marketed commercially, verapamil is possibly the best understood of the compounds of its class. Accordingly, the use of (+)-verapamil represents a preferred, but not a sole, embodiment of the invention. Other "inactive" isomers of verapamil analogs and other CCBs will possess similar anti-inflammatory activity without the cardiovascular effects associated with their respective "active" isomers.

The preparation of verapamil, a preferred compound for use in the present invention, is described in U.S. Pat. No. 3,261,859. Example 6 therein teaches verapamil specifically, which is referred to as "D365" in that patent.

For synthesis and configuration of the enantiomers of verapamil, see Ramuz, *Helv. Chin. Acta,* 58:2050 (1975). For a comprehensive description, see Z. L. Chang, *Analytical Profiles of Drug Substances,* 17:643–674, K. Florey, Ed. (Academic Press, NY 1988).

Verapamil as a racemate is commercially available, for example, under the trade name CALAN® from G. D. Searle and Company, and under the trade name ISOPTIN® from Knoll Pharmaceutical Company. Verapamil is available in an oral dosage form, an oral form with sustained release, and an injectable form which is typically used intravenously. If desired, the practitioner may use one of these commercial products as a starting material and preferentially isolate the plus isomer for use according to the invention. Alternatively, the separated isomers of verapamil are also commercially available Research Biochemicals International, Natick, Mass., U.S.A.).

While calcium channel blockers and verapamil have been used above to illustrate the methods of the present invention, one of skill in the art will understand that any of the above-described TNF inhibitors could also be used in any of the methods of treatment. Nevertheless, other classes of TNF inhibitors are discussed below.

b. Neuropeptide and Neurotransmitter Antagonists

Since the release of Substance P has been suggested to trigger mast cell degranulation, macrophage and lymphocyte activation and adhesion molecule expressions, Substance P antagonists (e.g.; spantide) or neurokinin-1 receptor antagonists (e.g., CP-96,345) can be administered to ameliorate the effect of this neuropeptide. Additionally, since acetylcholine is one of the most potent neurotransmitters released from activated neuroterminals, anticholinergic substances such as atropine, ipratropium bromide, and the like can be effective in alleviating the immediate skin inflammation/immune response.

Additionally, mast cell mediator release inhibitors, such as cromolyn sodium or sodium cromoglycate and tiacrilast can serve as pharmacological agents useful in the methods described herein.

c. Antihistamines

Histamine can be released either from degranulating skin mast cells or peripheral nerve endings during the skin's inflammatory/immune response. Histamine is known to produce the redness, wheal, and flare reactions in the skin. In addition, it has been suggested that histamine can work in synergy with TNF to further amplify the keratinocyte activation process through ICAM-1 and MHC Class II molecule expression.

Antihistamines are compounds which can block the binding of histamine to the histamine receptors. The histamine receptors comprise a family of receptors with diverse pharmacological properties and are typically classified as H-1, H-2, and H-3 receptors. Although the involvement of the other receptors should not be excluded, it is the inhibition of histamine binding to the H-2 receptor that is of particular interest in the skin's inflammatory/immune response. Thus, compounds known to be H-2 antagonists, such as cimetidine, and the like, either alone or in combination with iontophoresis, can be utilized in the methods described herein.

d. Immunosuppressants

The first evidence suggesting efficacy for the treatment of inflammatory skin disorders with immunosuppressants came from the systemic administration of cyclosporin A to psoriatic patients. Although its use is fraught with nephro- and hepatic toxicity, cyclosporin A has been employed in the treatment of many inflammatory skin disorders. Recently, it has been demonstrated that topical application of immunosuppressants, such as FK-506, was effective in inhibiting skin inflammatory reactions in an allergic contact dermatitis model. Other immunosuppressants, such as corticosteroids (see, e.g., American Medical Association (1992) *Drug Evaluations* (Subscriptions), Section 1), azathioprine (Imuran®), bromocriptine (Parlodel®), chlorambucil (Leukeran®), colchicine, cyclophosphamide (Cytoxan® or Neosar®), cyclosporine (Sandimmune®), dapsone, methotrexate (Folex® or Mexate®), and fluorouracil (Adrucil®); rapamycin; and FK-520-like macrolide antibiotics will also find use in the methods of this invention.

e. Other Pharmacological Agents

Other embodiments will be drawn to the pharmacological intervention of the biological and pharmacological effects of the proinflammatory cytokines, neuropeptides, neurotransmitters, and secretory granule exocytosis processes. Examples of suitable pharmacological agents for these purposes include: $\beta_2$-agonists, such as isoproterenol, bitolterol mesylate (Tornalate®), isoetharine hydrochloride (Bronkosol®), metaproterenol sulfate (Alupent® or Metaprel®), and pirbuterol acetate (Maxair®); protein kinase C inhibitors, such as sphingosine; phospholipase C inhibitors; vitamin $D_3$ and analogs, such as MC-903; proton-pump inhibitors; 5-hydroxy tryptamine antagonist, such as piperone; and other inhibitors of IL-1 induced IL-8 production.

Some embodiments of the invention will be drawn to the delivery of the "counter-ion", i.e., the ion which is implicated in the intracellular and intercellular mechanisms, e.g., ion pumps, transport systems, and ion channels, which control the concentrations and gradients for a given ion. For example, potassium ion will be administered to modulate the calcium ion concentrations and gradients, and vice versa.

Additional pharmacological agents for use in the present invention include inorganic calcium transport inhibitors such as lanthanides, for example, $La^{+3}$, either as an aqueous solution of $LaCl_3$ or any liquid or semisolid formulation containing lanthanide ion (e.g., as the citrate, versenate, or other salt) delivered either passively or by iontophoresis (see, e.g., Diezel et al. (1989) *J. Invest. Dermat.* 93:322–326); agents that mediate sodium ion transport, such as amiloride (see, e.g., Gallo and Granstein (1989) *Arch. Dermatol.* 125:502–506); and substances which block depolarization-induced calcium ion influx through both L- (i.e., dihydropyridine-sensitive) and T-channels in human neuroblastoma cells, such as menthol (see Sidell et al. (1990) *J. Cell. Physiol.* 142:410–419) and any other agents which can directly or indirectly modulate the intracellular ion concentrations. The above-cited references are each incorporated herein by reference.

In addition, intracellular ion modulating agents useful in the present invention may include compounds which interfere with ion-protein interactions such as calmodulin antagonists. Calmodulin is a calcium-binding protein which appears to be a ubiquitous intracellular calcium receptor, playing a part in the majority of the calcium-regulated processes studied in eucaryotic cells. Among the compounds known to be calmodulin antagonists are calmidazolium, chlorpromazine, melitin, ophiobolin A, phenoxybenzamine (also an alpha blocker), trifluoperazine, W-5, W-7, W-12, and W-13. Other calmodulin antagonists include imidazo-(1, 2-A)-pyridine analogs (see U.S. Pat. No. 5,22449808 to Kozai, et al.), (ethylenedinitrilo)-tetraacetic acid (EDTA), 6-(2-alk(en)-oxy-phenyl-2-(1H)-pyridinone and pyridine-thione analogs (see U.S. Pat. No. 5,254,571 to Coates, et al.), peptides such as those described in Japanese Patent Application Serial No. 1,006,294, anthracycline derivatives such as those described in European Patent Application Serial No. 280,167 to Hoffman et al., pyrrolobenzoxazepine derivatives such as those described in U.S. Pat. No. 4,758,559 to Wasley, et al., pyridine derivatives such as those described in U.S. Pat. Nos. 4,795,814 to Nishitani, et al., and 5,034, 395 and 5,137,889 to Nagami, et al., phenothiazine, thioxanthene, butyrophenone, diphenylbutylamine, dibenzodiazepine, benzodiazepine, dibenzazepine and napthalenesulphonamide derivatives such as those described in U.S. Pat. Nos. 4,654,323 and 4,777,171 to Beitner, 2,6-dialkyl4-phenyl-3,5,-dicarboxylic acid esters, such as those described in U.S. Pat. Nos. 5,034,395 and 5,137,889 to Nagami, et al., and n-trans-cinnamyl-N'-4,4'-difluoro-benzhydryl-piperazine and its derivatives (see German Patent Nos. 3,410,848 A and 3,410,848 C to Materazzi, et al.) The above listed patents and patent applications are incorporated herein by reference.

Still further, any pharmacological agent that can inhibit secretory organelle exocytosis (extrusion) processes, i.e., compounds which modulate intraorganelle pH, will find use in the methods claimed herein. Examples of such pharmacological agents include dual cyclooxygenase-lipoxygenase inhibitors, such as those described in PCT publication No. WO 92/10190; ion channel blockers; compounds that modulate microtubule assembly, for example, colchicine, vinca alkaloids such as vincristine (see Caidbey et al. (1975) *Arch. Dermatol.* 111:33) and plasma or vacuolar proton pump inhibitors such as omeprazole, N-ethyl maleimide, diethyl stilbestrol, and the like.

Additional pharmacological agents that can be delivered topically, transdermally, or iontophoretically, according to the methods described herein include other cytokines, peptides, oligosaccharide, proteins and oligonucleotides capable of suppressing the production of TNF, for example, IL-6, TGF-α, IL4, and IL-10; anti-TNF antibodies (see, e.g., Beutler et al. (1985) *Science* 229:869–871; Tracey et al. (1987) *Nature* 330:662–664; and Hinshaw et al. (1990) *Circ. Shock* 30:279–292) TNF-inhibitors and soluble TNF receptors; antioxidants, for example, butylated hydroxyanisole; 2-aminopurine; and thalidomide.

f. Formulations

According to one group of embodiments, pharmacological agents capable of modulating inflammation are applied to the skin, either iontophoretically, sonophoretically, topically, or through other routes of drug administration, such as oral (PO), intraperitoneal (IP), intravenous (IV), vaginal, rectal, intramuscular (IM), aerosol, nasal spray, ocular, transdermal, colonic, and the like.

These pharmacological agents can be in a variety of forms. These include, for example, solid, semi-solid and liquid dosage forms, such as tablets, pills, powders, liquid solutions or suspensions, liposomes, injectable and infusible solutions. These agents can also be incorporated into various cosmetic and toiletry formulations, either for therapeutic usage, or to mitigate irritation (or sensitization accompanying these formulations (See Flick E. W. COSMETIC AND TOILETRY FORMULATIONS, 2nd Ed., Noyes Publications, 1989). The preferred form depends on the intended mode of administration and therapeutic application.

While it is possible to administer the active ingredient alone, it is preferable to present it as part of a pharmaceutical formulation. These formulations comprise the pharmacological agent in a therapeutically or pharmaceutically effective dose together with one or more pharmaceutically or therapeutically acceptable carriers and optionally other therapeutic ingredients. Various considerations are described, e.g., in Gilman et al. (eds) (1990) GOODMAN AND GILMAN'S: THE PHARMACOLOGICAL BASES OF THERAPEUTICS, 8th Ed., Pergamon Press; NOVEL DRUG DELIVERY SYSTEMS, 2nd Ed., Norris (ed.) Marcel Dekker Inc. (1989), and REMINGTON'S PHARMACEUTICAL SCIENCES, the full disclosures of which are incorporated herein by reference. Methods for administration are discussed therein, e.g., for oral, intravenous, intraperitoneal, or intramuscular administration, and others. Pharmaceutically acceptable carriers will include water, saline, buffers, and other compounds described, e.g., in the MERCK INDEX, Merck & Co., Rahway, N.J. See, also, BIOREVERSIBLE CARRIERS IN DRUG DESIGN, THEORY AND APPLICATION, Roche (ed.), Pergamon Press, (1987).

(1) Topical Formulations

Typically, the topical formulations will comprise a preparation for delivering a pharmacological agent directly to the affected skin comprising the pharmacological agent, typically in concentrations in the range from about 0.001% to 20%; preferably, from about 0.01 to about 10%; more preferably, from about 0.1 to about 5%; together with a non-toxic, pharmaceutically acceptable topical carrier. See DERMATOLOGICAL FORMULATIONS: PERCUTANEOUS ABSORPTION, Barry (ed.), Marcel Dekker Inc., (1983). For standard dosages of conventional pharmacological agents, see, e.g., PHYSICIANS DESK REFERENCE (1992 Edition); and American Medical Association (1992) *Drug Evaluations* (Subscriptions).

Topical preparations can be prepared by combining the pharmacological agent with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable-oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

Dosage forms for the topical administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

The pharmacological agents which are incorporated into the topical formulations described above can be any of the TNF inhibitors described above, or ion modulating agents such as $La^{+3}$. In preferred embodiments, for TNF inhibitors having one or more optical centers, a specific optical isomer of the inhibitor is used. In other preferred embodiments, the TNF inhibitor is a benzoacetonitrile, a dihydropyridine or a benzothiazepinone, more preferably as a specific optical isomer. Still further preferred are those embodiments in which a benzoacetonitrile, preferably verapamil, is present predominantly as its plus isomer. The specific optical isomer is preferably the isomer which is the less cardiovascularly active isomer. Alternatively, the specific optical isomer can be selected to provide optimal modulation of TNF production.

Additionally, other pharmacological agents which have optical isomers are also expected to show a stereoselectivity similar to that which is found with the benzoacetonitriles. Thus, the present invention also provides methods which use specific isomers of diuretics, antidiarrheals, phosphodiesterase inhibitors and β-agonists.

The TNF inhibitor, for example, (+)-verapamil can be formulated into topical preparations either for local therapy or for transdermal delivery systemically. Formulations include a therapeutically effective concentration of a TNF inhibitor, preferably (+)-verapamil, or a related analog, in a dermatological vehicle. The amount of the TNF inhibitor to be administered, and its concentration in the topical formulations, depends upon the vehicle selected, the clinical condition of the patient, the side effects and the stability of the compound in the formulation. Thus, the physician will employ the appropriate preparation containing the appropriate concentration in the formulation, as well as the amount of formulation administered, depending upon clinical experience with the patient in question or with similar patients.

One example of a topical formulation includes about 1% (+)-verapamil by weight; about 35–40% alcohol, predominantly ethanol and isopropyl alcohol; about 30% propylene glycol; about 15% polyethylene glycol 400 (PEG 400); about 10% water; and small amounts, such as about 1% or less, of each of glycerin, sodium laurel sulfate, stabilizers, preservatives, humectants, thickeners, and chemicals selected for the addition of color or scent.

(2) Oral Formulations

For delivery to the buccal membranes, typically an oral formulation, such as a lozenge, tablet, or capsule will be used. The method of manufacture of these formulations are known in the art, including but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

Colon-targeted delivery can be carried out using an oral dosage form such as that described in U.S. Pat. No. 4,111,201. These osmotic pump delivery systems for oral formulations (termed OROS™) will be particularly useful for the treatment of systemic inflammatory bowel disease. Other oral delivery systems which tend to localize or concentrate the administered drug in the colon would be quite useful for treating inflammatory bowel disease.

(3) Aerosol Formulations

For delivery to the nasal or bronchial membranes, typically an aerosol formulation will be employed. The term "aerosol" includes any gas-borne suspended phase of the pharmacological agent which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the pharmacological agent suspended in air or other carrier gas, which may be delivered by insufflation from an inhaler device, for example.

For solutions used in making aerosols, the preferred range of concentration of the pharmacological agent is 0.1–100 milligrams (mg)/milliliter (mL), more preferably 0.1–30 mg/mL, and most preferably, 1–10 mg/mL. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Jones, DRUG DELIVERY TO THE RESPIRATORY TRACT, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

Solutions of the pharmacological agent may be converted into aerosols by any of the known means routinely used for making aerosol inhalant pharmaceutical. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

(4) Solutions and Suspensions

Solutions and aqueous suspensions are the pharmaceutical forms most widely used to administer drugs that must be active on the eye surface or in the eye after passage through the cornea or conjunctiva. To increase bioavailability of drugs, to extend therapeutic efficacy, and to improve patient compliance, various dosage forms have been developed over the years. These include soluble inserts (undergoing gradual dissolution/or surface erosion), insoluble inserts (e.g., medicated contact lenses such as Ocusert®, etc.), gels (e.g., Gelrite®), liposomal and drug delivery via nanoparticles (emulsion, suspension, etc.), and ointment (See Edman, BIOPHARMACEUTICS OF OCULAR DRUG DELIVERY, CRC Press, 1993).

(5) Transdermal Patches

Pharmacological agents also may be administered via transdermal patch. Transdermal patches have the added advantage of providing controlled delivery of a pharmacological agent to the skin or body. See TRANSDERMAL DRUG DELIVERY: DEVELOPMENTAL ISSUES AND RESEARCH INITIATIVES, Hadgraft and Guy (eds.), Marcel Dekker, Inc., (1989); CONTROLLED DRUG DELIVERY: FUNDAMENTALS AND APPLICATIONS, Robinson and Lee (eds.), Marcel Dekker Inc., (1987); and TRANSDERMAL DELIVERY OF DRUGS, Vols. 1–3, Kydonieus and Berner (eds.), CRC Press, (1987). Such dosage forms can be made by dissolving, dispersing or otherwise incorporating the pharmacological agent in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

A variety of types of transdermal patches will find use in the methods described herein. For example, an adhesive patch, or adhesive matrix patch, can be prepared from a backing material and an adhesive, such as an acrylate adhesive. The pharmacological agent and any enhancer, or combination of enhancers, are formulated into the adhesive casting solution and allowed to mix thoroughly. The solution is cast directly onto the backing material and the casting solvent is evaporated in an oven, leaving an adhesive film. A release liner can be attached to complete the system. Examples of adhesive matrix-type transdermal patches are found in U.S. Pat. Nos. 5,302,395, Ebert et al.; 5,262,165, Govil et al.; 5,248,501, Parnell, F. W.; 5,232,702, Pfister et al.; 5,230,896, Yeh et al.; 5,227,169, Heiber, S., et al.; 5,212,199, Heiber et al.; 5,202,125, Ebert et al.; 5,173,302, Holmblad, et al.; 5,154,922, Govil, et al.; 5,139,786, Ferrini et al.; 5,122,383, Heiber et al.; 5,023,252, Hseih, D.; and 4,978,532, El-Rashidy, T. Each of these disclosures is incorporated herein by reference.

Alternatively, a polyurethane matrix patch can be employed to deliver the pharmacological agent. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and drug to the prepolymer results in the formation of a tacky firm elastomer that can be directly cast onto the backing material. A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer. Examples of such patches are found in U.S. Pat. Nos. 5,324,521, Gertner, et al.; 5,306,503, Muller, W.; 5,302,395, Ebert, C. D.; 5,296,230, Chien, et al.; 5,286,491, Amkraut, et al.; 5,252,334, Chiang, et al.; 5,248,501, Parnell, F. W.; 5,230,896, Yeh, et al.; 5,227,169, Heiber et al.; 5,212,199, Heiber et al.; 5,202,125, Ebert, C. D.; 5,173,302, Bergstrom, et al.; 5,171,576, Amkraut, et al.; 5,139,786, Ferrini, et al.; 5,133,972, Ferrini, et al.; 5,122,383, Heiber, et al.; 5,120,546, Hansen, J. A.; 5,118,509, Amkraut, A.; 5,077,054, Amkraut et al.; 5,066,494, Becher, F.; 5,049,387, Amkraut, A.; 5,028,435, Katz, et al.; 5,023,252, Hseih, D.; 5,000,956, Shaw, J. E.; 4,911,916, Cleary, G. W.; 4,898,734, Mathiowitz, et al.; 4,883,669, Chien, et al; 4,882,377, Sweet et al.; 4,840,796, Sweet et al.; 4,818,540, Chien et al.; 4,814,173, Song et al.; 4,806,341, Chien et al.; 4,789,547, Song et al.; 4,786,277, Powers et al.; 4,702,732, Powers et al.; 4,690,683, Chien et al.; and 4,627,429, Tsuk, A. G.; and 4,585,452, Sablotsky, S. Each of these disclosures is incorporated herein by reference.

Foam matrix patches are similar in design and components to the liquid reservoir system, except that the gelled drug solution is constrained in a thin foam layer, typically a polyurethane. This foam layer is situated between the backing and the membrane which have been heat sealed at the periphery of the patch.

The liquid reservoir patch will also find use in the methods described herein. This patch comprises an impermeable or semi-permeable, heat sealable backing material, a heat sealable membrane, an acrylate based pressure sensitive skin adhesive, and a siliconized release liner. The backing is heat sealed to the membrane to form a reservoir which can then be filled with a solution of the drug, enhancers, gelling agent, and other excipients. Such patches are described in U.S. Pat. Nos. 5,324,521, Gertner, et al.; 5,300,299, Sweet, et al.; 5,275,819, Amer, et al.; 5,246,705, Venkatraman, et al.; 5,242,111, Nakoneczny, et al.; 5,232,702, Pfister, et al.; 5,227,169, Heiber, et al.; 5,213,568, Lattin, et al.; 5,212,199, Heiber, et al.; 5,156,591, Gross, et al.; 5,122,383, Heiber, et al.; 5,108,710, Little, et al.; 5,013,552, Amer, et al.; 4,999,379, Fankhauser, P.; 4,810,499, Nuwayser, E. S.; 4,777,170, Heinrich, W. A.; and 4,687,481, Nuwayser, E. Each of these disclosures is incorporated herein by reference.

In one embodiment, a TNF inhibitor can be applied to the skin in conjunction with any device or delivery system which is attached to the skin through an adhesive, e.g., a transdermal patch or an ostomy device such as a colostomy bag. For example, a benzoacetonitrile can be incorporated into a transdermal patch, either alone or in combination with one or more different drugs, or the benzoacetonitrile can be applied to the area of the skin upon which the patch is to be placed prior to attachment of the transdermal patch to the skin. Such a combination can be used to deliver systemic anti-inflammatories or reduce the well-known problems of skin irritation caused by the attachment of a transdermal patch to the skin. The TNF inhibitors which act as anti-inflammatories can also be applied after the patch is removed to treat any sensitization or inflammation associated with the attachment of the patch.

(6) Occlusion

Occlusion comprises the application of a hydrated dressing, optionally with a pharmacological agent and a sealing material overlaid on the outside, to the area of skin to be treated. Occlusion prevents loss of the drug from the skin, promotes skin hydration, and increases skin temperature. These actions have been shown to enhance the penetration of certain medications used in the treatment of psoriasis, leg ulcers, some dermatitis and ekratodermas. TNF inhibitors can be administered using a number of different occlusive dressings, including those described below, to treat inflammatory conditions.

A variety of synthetic occlusive dressings with variable occlusive properties are now available for use in promoting topical drug absorption and wound healing. Examples include hydrocolloids, such as hydroactive particles in a hydrophobic polymer (e.g., DuoDERM® Dressing, Convatec/Division, Squibb Co., Princeton, N.J.); hydrogels, such as water and polyethylene oxide reinforced with polyethylene film (e.g., Vigilon®, Bard Home Health Division, Berkeley Heights, N.J. and Spenco 2nd Skin Dressing®, Spenco Medical Inc., Ward, Tex.); polyethylene (e.g., Glad Cling Wrap®, Union Carbide Corp., Home and Automotive Products Division, Danbury, Conn.); polyurethane (e.g., Op-Site®, Smith & Nephew, Welwyn Garden City, Hertfordshire, England; Tegaderm®, 3M Company, Medical Surgical Division, St. Paul, Minn.; Bioclusive®, Johnson & Johnson Products, New Brunswick, N.J.; and Ensure®, Becton Dickinson Acute Care/Deseret, Sandy, Utah); polyvinylidine (e.g., Saran Wrap®, Dow Chemical Co., Indianapolis, Ind.); and siloxane or silicone dressings, including dimethylpolysiloxane polymer-elastomer bonded to a finely knit nylon fabric (e.g., Biobrane®, Woodroof, Santa Ana, Calif.). See, also, American Medical Association (1992) *Drug Evaluations* (Subscriptions), Section 1.

(7) Iontophoresis

Some embodiments of the present invention will employ the use of an electric field to administer a mixture of a therapeutic agent and a TNF inhibitor. The term "electrotransport" is used to refer to methods and apparatus for transdermal delivery of therapeutic agents by means of an applied electromotive force to an electrolyte-containing reservoir. The particular therapeutic agent being delivered may be charged or uncharged, depending upon the particular method chosen.

When the therapeutic species being delivered is charged, for example potassium ion, calcium ion, or any charged atom or molecule, the process is referred to as iontophoresis. When the therapeutic species delivered is uncharged, it may be considered delivered by means of electro-osmosis techniques or other electrokinetic phenomenon such as electrohydrokinesis, electro-convection or electrically-induced osmosis. In general, these latter electrokinetic delivery processes of uncharged species into a tissue result from the migration of solvent, in which the uncharged species is dissolved, as a result of the application of electromotive force to the electrolyte reservoir. Of course during the process, some transport of charged species will take place as well.

In general, iontophoresis is an introduction, by means of electric current, of ions of soluble salts into the tissues of the body. More specifically, iontophoresis is a process and technique which involves the transfer of ionic (charged) species into a tissue (for example through the skin of a patient) by the passage of a electric current through an electrolyte solution containing ionic molecules to be delivered (or precursors for those ions), upon application of an appropriate electrode polarity. That is, ions are transferred into the tissue, from an electrolyte reservoir, by application of electromotive force to the electrolyte reservoir.

If the electrotransport method is iontophoresis, generally the active electrode includes the therapeutic species as a charged ion, or a precursor for the charged ion, and the transport occurs through application of the electromotive force to the charged therapeutic species. If other electrotransport phenomenon are involved, the therapeutic species will be delivered in an uncharged form, transfer being motivated, however, by electromotive force. For example, the applied current may induce movement of a non-therapeutic species, which carries with it water into the subject. The water may have dissolved therein the therapeutic species. Thus, electrotransport of the non-therapeutic charged species induces movement of the therapeutic but non-charged species.

Through iontophoresis, either positively charged drugs (medication) or negatively charged drugs (medication) can be readily transported through the skin and into the patient. This is done by setting up an appropriate potential between two electrode systems (anode and cathode) in electrical contact with the skin. If a positively charged drug is to be delivered through the skin, an appropriate electromotive force can be generated by orienting the positively charged drug species at a reservoir associated with the anode. Similarly, if the ion to be transferred across the skin is negatively charged, appropriate electromotive force can be generated by positioning the drug in a reservoir at the cathode. Of course, a single system can be utilized to transfer both positively charged and negatively charged drugs into a patient at a given time; and, more than one cathodic drug and/or more than one anodic drug may be delivered from a single system during a selected operation. For general discussions of iontophoresis, see, e.g., Tyle (1989) *J. Pharm. Sci.* 75:318; Burnette, *Iontophoresis* (Chapter 11) in TRANSDERMAL DRUG DELIVERY Hadgraft and Guy (eds.) Marcel Dekker, Inc.: New York, N.Y.; Phipps et al. (1988) *Solid State Ionics* 28–30:1778–1783; Phipps et al. (1989) *J. Pharm. Sciences* 78:365–369; and Chien et al. (1988) *J. Controlled Release,* 7:1–24, the full disclosures of which are incorporated herein by reference.

A wide variety of iontophoresis devices are presently known. See, e.g., Phipps et al. U.S. Pat. No. 4,744,788; Phipps et al. U.S. Pat. No. 4,747,819; Tapper et al. European Patent Application Publication No. 0318776; Jacobsen et al. European Patent Application Publication No. 0299631; Petelenz et al. U.S. Pat. No. 4,752,285; Sanderson et al. U.S. Pat. No. 4,722,726; Phipps et al. U.S. Pat. No. 5,125,894; and Parsi U.S. Pat. No. 4,731,049, the full disclosures of each which are incorporated herein by reference.

In typical, conventional, electrotransport devices, for example iontophoresis devices, two electrodes are generally used. Both electrodes are disposed so as to be in intimate electrical contact with some portion (typically skin) of the subject (human or animal) typically by means of two remote electrolyte-containing reservoirs, between which current passes as it moves between the skin and the electrodes. One electrode, generally referred to herein as the "active" electrode, is the electrode from which the substance (medicament, drug precursor or drug) is delivered or driven into the body by application of the electromotive force. The other electrode, typically referred to as an "indifferent" or "ground" electrode, serves to close the electrical circuit through the body. In some instances both electrodes may be "active", i.e. drugs may be delivered from both. Herein the term electrode, or variants thereof, when used in this context refers to an electrically conductive member, through which a current passes during operation.

A variety of electrode materials, ranging from platinum to silver-silver chloride, are available for these devices. The primary difference in these materials is not in their ability to generate an electric potential across the skin, but rather in certain nuances associated with their performance of this function. For example, platinum electrodes hydrolyze water, thus liberating hydrogen ions and subsequently, changes in pH. Obviously, changes in pH can influence the ionization state of therapeutic agents and their resulting rate of iontophoretic transport. Silver-silver chloride electrodes, on the other hand, do not hydrolyze water. However, these electrodes require the presence of chloride ion which may compete for current-induced transport.

Electrotransport devices generally require a reservoir as a source of the species (or a precursor of such species) which is to be moved or introduced into the body. The reservoir typically will comprise a pool of electrolyte solution, for example an aqueous electrolyte solution or a hydrophilic, electrolyte-containing, gel or gel matrix, semi-solid, foam, or absorbent material. Such drug reservoirs, when electrically connected to the anode or the cathode of an iontophoresis device, provide a source of one or more ionic species for electrotransport.

Generally, buffers will also be incorporated into the reservoir to maintain the reservoir environment at the same charge as the electrode. Typically, to minimize competition for the electric current, a buffer having the opposite charge to the drug will be employed. In some situations, for example, when the appropriate salt is used, the drug may act as its own buffer.

Other variables which may effect the rate of transport include drug concentration, buffer concentration, ionic strength, nonaqueous cosolvents, and any other constituents in the formulation. In general, to achieve the highest transport efficiency, the concentration of all ionic species, save the therapeutic agent itself, is minimized.

In conjunction with the patient's skin in electrical communication with the electrodes, the circuit is completed by connection of the two electrodes to a source of electrical energy as a direct current; for example, a battery or a source of appropriately modified alternating current. As an example, if the ionic substance to be driven to the body is positively charged, then the positive electrode (the anode) will be the active electrode and the negative electrode (the cathode) will serve to complete the circuit. If the ionic substance to be delivered is negatively charged, then the negative electrode (cathode) will be the active electrode and the positive electrode (anode) will be the indifferent electrode.

Chemical enhancers, vasodilators, and electroporation can also be utilized to alter the iontophoretic transport rate. For example, the coapplication of oleic acid to the skin causes a large decrease in the skin impedance or resistance which is inversely related to permeability or transport. See Potts et al. (1992) *Solid State Ionics* 53–56:165–169. Thus, instead of the current passing primarily through the shunt pathways (e.g., the follicles and sweat ducts), the ions constituting the current can more uniformly permeate the lipid milieu of the stratum corneum at a lower current density. Thus, the epidermis, as well as the peripheral neurons surrounding the hair follicles and sweat ducts, will be able to experience the electrical stimulation.

Substances which would perturb the normal structure of the stratum corneum could, in turn, disrupt the intercellular lipid organization, thus reducing its effectiveness as a dielectric barrier. These substances could include any lipid material which would partition into the stratum corneum lipids causing a direct effect or any material which would effect the proteins and cause an indirect perturbation of the lipid structure. Furthermore, solvents, such as ethanol, can remove lipids from the stratum corneum, thus destroying its lipid organization and decreasing its dielectric properties.

Examples of stratum corneum lipid perturbants include, but are not limited to, alcohol enhancers, such as alkanols with one to sixteen carbons, benzyl alcohol, butylene glycol, diethylene glycol, glycofurol, glycerides, glycerin, glycerol, phenethyl alcohol, polypropylene glycol, polyvinyl alcohol, and phenol; amide enhancers, such as N-butyl-N-dodecylacetamide, crotamiton, N,N-dimethylformamide, N,N-dimethylacetamide, N-methyl formamide, and urea; amino acids, such as L-α-amino acids and water soluble proteins; azone and azone-like compounds, such as azacycloalkanes; essential oils, such as almond oil, amyl butyrate, apricot kernel oil, avocado oil, camphor, castor oil, 1-carvone, coconut oil, corn oil, cotton seed oil, eugenol, menthol, oil of anise, oil of clove, orange oil, peanut oil, peppermint oil, rose oil, safflower oil, sesame oil, shark liver oil (squalene), soybean oil, sunflower oil, and walnut oil; vitamins and herbs, such as aloe, allantoin, black walnut extract, chamomile extract, panthenol, papain, tocopherol, and vitamin A palmitate; waxes, such as candelilla wax, carnuba wax, ceresin wax, beeswax, lanolin wax, jojoba oil, petrolatum; mixes, such as primary esters of fractionated vegetable oil fatty acids with glycerine or propylene glycol, and interesterified medium chain triglyceride oils; fatty acids and fatty acid esters, such as amyl caproate, butyl acetate, caprylic acid, cetyl ester, diethyl sebacate, dioctyl malate, elaidic acid ethyl caprylate, ethyl glycol palmitostearate, glyceryl beheate, glucose glutamate, isobutyl acetate, laureth-4, lauric acid, malic acid, methyl caprate, mineral oil, myristic acid, oleic acid, palmitic acid, PEG fatty esters, polyoxylene sorbitan monooleate, polypropylene glycols, propylene glycols, saccharose disterate, salicylic acid, sodium citrate, stearic acid, soaps, and caproic-, caprylic-, capric-, and lauric-triglycerides; macrocyclics, such as butylated hydroxyanisole, cyclopentadecanolide, cyclodextrins; phospholipid and phosphate enhancers, such as dialkylphosphates, ditetradecyl phosphate, lecithin, 2-pyrrolidone derivatives, such as alkyl pyrrolidone-5-carboxylate esters, pyroglutamic acid esters, N-methyl pyrrolidone, biodegradable soft penetration enhancers, such as dioxane derivatives and dioxolane derivatives; sulphoxide enhancers, such as dimethyl sulphoxide and decylmethyl sulphoxide; acid enhancers, such as alginic acid, sorbic acid, and succinic acid; cyclic amines; imidazolinones; imidazoles; ketones, such as acetone, dimethicone, methyl ethyl ketone, and pentanedione; lanolin derivatives, such as lanolin alcohol, PEG 16 lanolin, and acetylated lanolin; oxazolines; oxazolindinones; proline esters; pyrroles, urethanes; and surfactants, such as nonoxynols, polysorbates, polyoxylene alcohols, polyoxylene fatty acid esters, sodium lauryl sulfate, and sorbitan monostearate.

In electroporation, which may have the same net effect as the use of chemical enhancers plus conventional iontophoresis, transient pores in the lipid structure of membranes, such as the stratum corneum, are created by the applied electric field. Such a technique has been used to introduce DNA into various cells. See Chang et al. (1992) HANDBOOK OF ELECTROPORATION AND ELECTROFUSION Academic Press: New York. Generally, electroporation involves the application of infrequent, short (about 1 millisecond), high voltage (5–300 volts) electric pulses.

Therefore, according to another aspect of the present invention, the inflammation, irritation, and/or sensitization which frequently occurs with transdermal or iontophoretic delivery of drugs, and in other topical products such as cosmetics, can be ameliorated by pre-, co-, or post-administration of a TNF inhibitor. Such transdermal- and iontophoresis-related inflammation is described in, e.g., Hogan, et al., *J. Am. Acad. Dermatol.*, 22:811–814 (1991); Holdiness, *Contact Dermatitis*, 20:3–9 (1989); Ledger, *Advanced Drug Delivery Reviews*, 9:289–307 (1992); and Lynch, et al., *J. Control. Release*, 6:39–50 (1987), each of which is incorporated herein by reference.

Accordingly, the present invention includes the use of a TNF inhibitors or chemical anti-inflammatory agent in conjunction with iontophoretic delivery of drugs to reduce the above-described sensitivity and irritation which accompanies iontophoretic drug delivery. Additionally, the TNF inhibitor can be used alone or in a combination of two or more. The agent or agents may be administered to the skin prophylactically, i.e., before the application of the iontophoretic current either topically or subcutaneously, or the agent or agents may be administered contemporaneously with the iontophoretic current, for example, by inclusion of the agent or agents with the reservoir of material to be delivered to the skin.

(8) Sonophoresis

Ultrasound also has been employed as a means of transdermal drug delivery, a technique known as sonophoresis or phonophoresis (see Type, et al., "Drug Delivery by Phonophoresis" *Pharm. Res.* 6:355–361 (1989) and Bommannan, et al., "Sonophoresis I: The Use of Ultrasound to Enhance Transdermal Drug Delivery" *Pharm. Res.* 9:559–564 (1989), both of which are incorporated herein by reference). High frequency sound waves have been observed to disrupt the superficial skin layers (e.g., the stratum corneum); thereby enhancing the transport of drugs into the skin. Sonophoresis has been reported to enhance drug delivery while avoiding the problems of permeability and long lag times before achieving therapeutically useful flux associated with other methods of transdermal drug delivery (see Bommannan (1989)). Sonophoresis at a frequency of 10–16 MHz has been shown to deliver materials into the skin in as few as 5 minutes (see Bommannan, et al., *Pharmaceutical Research*, 9:8 1043–1047 (1992)). Thus, sonophoresis provides another method for the topical delivery of anti-inflammatory substances.

(9) Combinations

Combinations of the various techniques described herein, i.e., electrotransport, sonophoresis, pharmacological intervention, and occlusion, can also be utilized. For example, pharmacological agents can be administered "actively" through the use of iontophoresis, or sonophoresis, optionally with stratum corneum lipid perturbants, or "passively", for example via the topical application of pharmacological agents, alone or with stratum corneum lipid perturbants. A further embodiment will combine iontophoresis with occlusion. Other embodiments will provide for the combination of occlusion and pharmacological agents. For example, microparticle encapsulated drugs can be suspended in the hydrophilic gel of an occlusive dressing. In addition, for the treatment of animals, pharmacological intervention frequently will be combined with occlusion. Still other embodiments will include the combination of various pharmacological agents. Still further embodiments of the invention include combinations of pharmacological agents which are administered by a combination of methods, described above.

When combinations of the therapeutic methods described herein are used in the treatment of inflammatory disorders, the particular sequence of treatment may or may not be important depending on the disorder being treated. For example, iontophoresis and pharmacological intervention may be applied sequentially to the patient, with the iontophoretic therapy being administered before, during, after, or any combination thereof. Sequential administration involves treatment with both therapies HMG at least on the same day (within 24 hours) and may involve continued treatment with the pharmacological agent on days that the iontophoretic therapy is not administered. The therapies may be administered to the patient at one time or over a series of treatments.

Alternatively, the patient may receive concurrent treatments with the various therapies. For example, an occlusive dressing containing a pharmacological agent may be applied to the affected area. Alternatively, a pharmacological agent may be delivered iontophoretically.

The optimal combination of therapies and their sequence will depend upon the type of disorder to be treated, the severity and course of that disorder, previous therapy, the patient's health status and response to the drugs, and the judgment of the treating physician.

g. Dosages and Schedules

The dosage of the specific compound for treatment depends upon many factors that are well known to those skilled in the art, for example, the particular agent; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

Typically, the topical formulations will comprise a preparation for delivering a pharmacological agent directly to the affected skin comprising the pharmacological agent, typically in concentrations in the range from about 0.001% to 20%; preferably, from about 0.01 to about 10%; more preferably, from about 0.1 to about 5%; and most preferably, from about 1 to about 5%, together with a non-toxic, pharmaceutically acceptable topical carrier. See DERMATOLOGICAL FORMULATIONS: PERCUTANEOUS ABSORPTION, Barry (ed.), Marcel Dekker Inc., (1983). For standard dosages of conventional pharmacological agents, see, e.g., PHYSICIANS DESK REFERENCE (1992 Edition); and American Medical Association (1992) *Drug Evaluations* (Subscriptions).

For reasons of patient compliance, the methods for regulating the rate of lamellar body (or membrane coating granule) extrusion in mucosal membranes will typically be accomplished via pharmacological intervention. Transmucosal (i.e., sublingual, rectal, colonic, pulmonary, buccal and vaginal) drug delivery provides for an efficient entry of active substances to systemic circulation and reduce immediate metabolism by the liver and intestinal wall flora (See Chien Y. W., NOVEL DRUG DELIVERY SYSTEMS, Chapter 4 "Mucosal Drug Delivery," Marcel Dekker, Inc. (1992). Transmucosal drug dosage forms (e.g., tablet, suppository, ointment, gel, pessary, membrane, and powder) are typically held in contact with the mucosal membrane and disintegrate and/or dissolve rapidly to allow immediate local and systemic absorption.

For delivery to the buccal membranes, typically an oral formulation, such as a lozenge, tablet, or capsule will be used. The method of manufacture of these formulations are known in the art, including but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

For delivery to the nasal or bronchial membranes, typically an aerosol formulation will be employed. The term "aerosol" includes any gas-borne suspended phase of the pharmacological agent which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the pharmacological agent suspended in air or other carrier gas, which may be delivered by insufflation from an inhaler device, for example.

For solutions used in making aerosols, the preferred range of concentration of the pharmacological agent is 0.1–100 milligrams (mg)/milliliter (mL), more preferably 0.1–30 mg/mL, and most preferably, 1–10 mg/mL. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Jones, DRUG DELIVERY TO THE RESPIRATORY TRACT, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

Solutions of the pharmacological agent may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

Solutions and aqueous suspensions are the pharmaceutical forms most widely used to administer drugs that must be active on the eye surface or in the eye after passage through the cornea or conjunctiva. To increase bioavailability of drugs, to extend therapeutic efficacy, and to improve patient compliance, various dosage forms have been developed over the years. These include soluble inserts (undergoing gradual dissolution/or surface erosion), insoluble inserts (e.g., medicated contact lenses such as Ocusert®, etc.), gels (e.g., Gelrite®), liposomal and drug delivery via nanoparticles (emulsion, suspension, etc.), and ointment (See Edman, BIOPHARMACEUTICS OF OCULAR DRUG DELIVERY, CRC Press, 1993).

In one embodiment, a TNF inhibitor or an anti-inflammatory can be applied to the skin in conjunction with any device or delivery system which is attached to the skin through an adhesive, e.g., a transdermal patch or an ostomy device such as a colostomy bag. For example, an anti-inflammatory agent can be incorporated into a transdermal patch, either alone or in combination with one or more different drugs, or the TNF inhibitor or the anti-inflammatory agent can be applied to the area of the skin upon which the patch is to be placed prior to attachment of the transdermal patch to the skin. Such a combination can be used to deliver systemic TNF inhibitors or anti-inflammatories or reduce the well-known problems of skin irritation caused by the attachment of a transdermal patch to the skin. The TNF inhibitor or anti-inflammatory agent can also be applied after the patch is removed to treat any sensitization or inflammation associated with the attachment of the patch.

In other embodiments, the dosages of the calcium channel blockers, diuretics, antidiarrheals, phosphodiesterase inhibitors and β-agonists used to practice the invention include dosages effective to result in the desired anti-inflammatory effect or optimal modulation of TNF production. Estimation of appropriate dosage for the individual patient is well within the skill of the ordinary prescribing physician or other appropriate health care practitioner. As a guide, the practitioner can use conventionally available advice from a source such as the *Physician's Desk Reference,* 48th Edition, Medical Economics Data Production Co., Montvale, N.J. 07645-1742 (1994), ("PDR" hereinafter). Typically, based on the in vitro potency of the drug, for example, the concentration of the drug which provides 50% inhibition ($IC_{50}$), the goal is to deliver steady state levels of drug (for example 10 to 100 fold higher than the $IC_{50}$) to the target tissue. Further, it is known in the art that the fraction of drug absorbed is 10–100% via oral administration, 100% intravenously, and about 2–100% via topical delivery. Thus, the total amount of drug which is administered to achieve a desired therapeutic advantage can be estimated based on the fraction of drug absorbed and the potency of the drug.

It is expected that the dosages of, for example, (+)-verapamil are approximately in the ranges of those for the racemate. However, lower starting dosages are advised until the practitioner develops experience with the inventive form of the drug. Ultimately, the usual patient treated with the invention may actually tolerate higher dosages of the inventive (+)-verapamil better than the conventional racemate because of the former's reduced effect on the cardiovascular system.

An initial oral dose of about 10 to about 180 mg per day of (+)-verapamil is recommended. The dosage may be increased, usually in increments of about 10 to 100 mg, to a maximum of about 480 mg per day. When the dosage is in the high range, such as at 480 mg per day, it is preferable to provide a divided dosage of 240 mg twice a day or every 12 hours.

When verapamil is injected, such as intravenously, the usual initial dose is about 0.1 to about 10 mg as a bolus over at least 2 minutes. This dosage may be repeated in about 30 minutes after the initial dose. For pediatric patients, the intravenous dosage is about 0.01 to about 0.2 mg per kg body weight, usually given in a single dose of about 0.15 to about 2 mg over at least 2 minutes. For children, a maximum of about 0.3 mg per kg body weight is typically given. Usually, it is not advisable to exceed 10 mg as a single intravenous dose.

After oral administration, verapamil is well absorbed and is rapidly bio-transformed during its first pass through the portal circulation. Subsequent bioavailability ranges from about 20% to about 35%. After about between one and two after oral administration, peak plasma concentrations are reached. The mean elimination half-life in single-dose studies ranges from about 2.8 to about 7.4 hours. After repetitive dosing, the half-life increased to a range of from about 4.5 to about 12.0 hours.

When administered intravenously, verapamil is rapidly metabolized. It is eliminated bi-exponentially with a rapid early distribution phase having a half-life of about 4 minutes. There is a slower, terminal elimination phase having a half-life of about 2 to about 5 hours. Verapamil is extensively metabolized in the liver. About 70% of an administered dose is excreted in the urine and about 16% in the feces within about 5 days.

Preferably, the dosage is repeated daily, or sometimes twice a day, until either a therapeutic result is achieved or until side effects warrant discontinuation of therapy.

2. Occlusion

The present invention also provides methods of modulating an inflammatory or immune response using occlusion in the absence of an added therapeutic agent. The method comprises the application of a hydrated dressing and a sealing material overlaid on the outside, to the area of skin to be treated. As noted above for the use of occlusive methods with drugs, occlusion promotes skin hydration, and increases skin temperature.

3. Application of an Electric Field

Some embodiments of the present invention will employ the use of an electric field to modulate the lamellar body extrusion process. The application of an electromotive force has been discussed above in connection with iontophoretic delivery of therapeutic agents.

The use of ion currents will find use in the treatment of skin diseases. According to this embodiment the ion current can be produced by applying the anode of an iontophoretic delivery device capable of delivering an electric field with a net current typically, from about 0.01 to about 10 mA, preferably from about 0.05 to about 8 mA, more preferably from about 0.1 to about 2 mA, and most preferably from about 0.1 to about 0.5 mA, to the affected skin. Typically, the cathode reservoir comprises a conductive gel and the anode reservoir comprises an aqueous solution of the potassium chloride, magnesium chloride, calcium chloride, or other salts of these positively charged ions. The current is applied typically from about 5 to about 240 minutes, preferably, from about 5 to about 120 minutes, and most preferably, from about 20 to about 40 minutes. The skin-contacting areas of both electrodes typically comprise about 1 $cm^2$ to 200 $cm^2$, and preferably about 5 $cm^2$ to 20 $cm^2$, as described in U.S. Pat. No. 5,221,254 to-Phipps.

In some embodiment, the enhancing current will be applied by placing an electrode on the affected area and delivering an electric current, typically, from about 0.01 to about 10 mA, preferably from about 0.05 to about 8 mA, and more preferably from about 0.5 to about 2 mA. Depending on the condition being treated, this current is applied typically from about 5 to about 240 minutes, preferably, from about 5 to about 120 minutes, and most preferably, from about 20 to about 40 minutes. Moreover, since in the absence of stratum corneum lipid perturbants, the current density tends to concentrate on the shunt pathways, the release of neuropeptides and neurotransmitters can activate the keratinocytes directly, or cause mast cell degranulation and macrophage activation. The release of TNF-$\alpha$ from the skin mast cells and macrophages can further amplify the signal for keratinocyte activation induced by neuropeptides such as substance P.

Thus, the present invention contemplates the use of enhancing currents, and the associated influx of ions into the stratum corneum-granulosum junction, optionally with stratum corneum lipid perturbants, to promote wound healing, to treat skin cancers, to increase local production of cytokines in order to fight infections, or to reduce inflammation.

4. Sonophoresis

As noted above, for in discussing delivery methods for therapeutic agents, ultrasound also has been employed as a means of transdermal drug delivery. This technique is also known as sonophoresis or phonophoresis. In the absence of therapeutic agents, these methods, (i.e., sonophoresis) through disrupting stratum corneum intercellular bilayers and the epidermal calcium gradients can modulate the epidermal immune responses associated with pro-inflammatory cytokine releases from lamellar bodies (see, Menon, et al., "Sonophoresis Disrupts Corneum(SC) Intercellular Bilayers and the Epidermal Calcium Gradient", *Abstracts* 100(4):497 (April 1993), which is incorporated herein by reference.

Accordingly, the present invention provides methods for the treatment of inflammation using sonophoresis. Further, the present invention contemplates the use of sonophoresis and associated flux of ions into the stratum corneum-granulosum junction, optionally with stratum corneum lipid perturants, to promote wound healing, to treat skin cancers and to increase local production of cytokines in order to fight infection.

5. Combinations

Combinations of the various techniques described herein, i.e., electrotransport, sonophoresis, pharmacological intervention, and occlusion, can also be utilized. For example, pharmacological agents can be administered "actively" through the use of iontophoresis, or sonophoresis, optionally with stratum corneum lipid perturbants, or "passively", for example via the topical application of pharmacological agents, alone or with stratum corneum lipid perturbants. A further embodiment will combine iontophoresis with occlusion. Other embodiments will provide for the combination of occlusion and pharmacological agents. For example, microparticle encapsulated drugs can be suspended in the hydrophilic gel of an occlusive dressing. In addition, for the treatment of animals, pharmacological intervention frequently will be combined with occlusion. Still other embodiments will include the combination of various pharmacological agents.

When combinations of the therapeutic methods described herein are used in the treatment of skin disorders, the particular sequence of treatment may or may not be important depending on the disorder being treated. For example, iontophoresis and pharmacological intervention may be applied sequentially to the patient, with the iontophoretic therapy being administered before, during, after, or any combination thereof. Sequential administration involves treatment with both therapies HMG at least on the same day (within 24 hours) and may involve continued treatment with the pharmacological agent on days that the iontophoretic therapy is not administered. The therapies may be administered to the patient at one time or over a series of treatments.

Alternatively, the patient may receive concurrent treatments with the various therapies. For example, an occlusive dressing containing a pharmacological agent may be applied to the affected area. Alternatively, a pharmacological agent may be delivered iontophoretically.

The optimal combination of therapies and their sequence will depend upon the type of skin disorder to be treated, the severity and course of that disorder, previous therapy, the patient's health status and response to the drugs, and the judgment of the treating physician.

IV. Therapeutic Regimens

A. The Treatment of Sensitization. Inflammation, and Irritation Accompanying Transdermal Drug Delivery or the Delivery of Drugs Using an Electric Field It is well recognized that application of drug-delivering transdermal delivery systems to the skin can result in the development of an immediate or delayed-type contact sensitivity to the drug being delivered or even to components of the delivery system. In addition, a variety of other inflammatory/immune related side effects, including edema, erythema, urticaria, hyperpigmentation, sensitization, and the like have been reported with the use of transdermal drug delivery devices and topical drug delivery.

There are seven transdermal therapeutic systems presently on the market: scopolamine (motion sickness), nitroglycerin (angina), clonidine (hypertension), estradiol (hormone replacement), nicotine (smoking cessation), fentanyl (analgesic) and testosterone (hypogonadism). See, e.g., THE PHYSICIAN'S DESK REFERENCE ("PDR"), 48th Ed. (Medical Economic Data 1994), which is incorporated herein by reference. Among all the transdermal patch users, the prevalence of "irritation" is observed in approximately 15% to 20% of the population with various degree of severity. This number does not include those cases where the irritation was so prominent (for example, transdermal delivery systems for $\beta$-blockers such as propranolol, antihistamines, etc.) that the overall development of these patches was suspended.

Irritation developed from either acute and especially chronic use of the transdermal patches could be a result of the vehicle, enhancer, adhesive, drug, or any combinations of these components. Both irritant and allergic contact dermatitis have been observed. For example, clonidine is known to cause allergic contact dermatitis. See, PDR, supra. The methods and TNF inhibitors disclosed in this application, can be used before, during, or subsequent to the application of a transdermal patch and can be incorporated in the same patch, or in a separate dosage form. Therefore, irritation due to the patch application can either be prevented by pretreatment and/or co-administration with the transdermal candidate, or be treated by the method and agents mentioned in this application following the use of transdermal patches to further improve the safety profile and compliance of any given transdermal product.

Methods of pretreatment include applying one or more of the compounds described above to the skin in the form of a topical preparation such as an ointment, gel or cream about 1 to 2 hours prior to the administration of the transdermal patch.

The generation of pain and burns also has been reported during electrotransport treatments. Erythema, a primary cutaneous reaction to irritant stimuli, has been frequently noted as a reaction to electrotransport but usually resolves without sequelae and is not necessarily associated with any permanent damage to the skin. Erythema associated with electrotransport can arise as a result of mild, non-specific irritation, for example, delivery of an irritant drug. However, the possibility of direct electric stimulation of erythema exists through activation of the C-fibers as discussed above.

The methods claimed herein provide means for controlling the sensitization, inflammation, and/or irritation accompanying transdermal drug delivery. Specifically, by maintaining the lamellar body extrusion process, the accelerated release of proinflammatory cytokines can be prevented. Additionally, by preventing the change in the neural polarity of the C-fibers, typically resulting from electrotransport, the release of neuropeptides and/or neurotransmitters from the afferent neurons and hence, the release of proinflammatory mediators can be prevented.

Typically, electrotransport with electrotransport and pharmacological intervention, either through the application of the necessary ions to maintain the homeostatic concentrations or a pharmacological agent to counteract the effects of the proinflammatory cytokines or MHC Class II antigen expression will be utilized. As noted above, the agents of the present invention may be used before, during or following the application of electrotransport to reduce irritation and sensitization resulting from such application.

B. The Treatment of Skin Diseases

One of the common clinical manifestations in skin diseases of diverse origins is compromised skin barrier function as evidenced by an increase in the transepidermal water loss (i.e., $\geq 10\%$ normal, as measured with an electric water analyzer, see, e.g., Grubauer et al. (1989) *J. Lipid Res.* 30:323–334). Barrier formation is a key responsibility of the epidermis, and abrogation of the lipid producing capacity of keratinocytes contributes to many skin diseases. For example, in psoriasis, a hyperproliferative epidermis is accompanied by an altered barrier function within the lesional plaque and a distinctive compartmentalization of cytokines in the epidermis and dermis has been observed. Cytokines that have been found to be elevated include transforming growth factor-alpha (TGF-$\alpha$), tumor necrosis factor-alpha (TFN), gamma interferon (IFN-$\gamma$), and IL-8.

The methods described herein will find use in the treatment of a variety of skin disorders, including those associated with differentiation and proliferation, for example, allergic dermatitis, psoriasis, eczematous or atopic dermatitis, acne vulgaris, comedones, polymorphs, nodulokystic acne, conglobata, senile acne, secondary acne such as solar acne, medicinal acne, irritant contact dermatitis or professional acne; other types of keratinization disorders, for example, ichthyoses, ichthyosiform conditions, Darier malady, palmoplantary keratodermies, leucoplasies and leucoplasiform conditions and lichen; other dermatologic disorders such as cutaneous T-cell lymphoma, blistery dermatoses and collagen maladies; and ageing of the skin, be it photoinduced or not.

Examples of specific skin diseases amenable to treatment with the methods described herein include psoriasis, eczematous dermatitis and all TNF-mediated skin disorders. Psoriasis is a common, idiopathic chronic skin disease characterized by inflamed, scaling, skin lesions containing infiltrates of neutrophils, lymphocytes and monocytes. According to the present invention, the term "psoriasis" is intended to embraces all forms of psoriasis, be they cutaneous, mucosal, or ungual, and even psoriatic rheumatism. The most effective treatment in the control of localized psoriasis, for most patients, is the use of topical corticosteroids and topical coal-tar preparations. With certain patients who have generalized psoriasis, it has been necessary to use a variety of systemic chemotherapeutic agents, especially methotrexate, which has the capacity to inhibit cell replication without a proportionate inhibition of cell function, i.e, keratinization.

Eczematous dermatitis is not a specific disease entity but a characteristic inflammatory response of the skin. Eczematous dermatitis is sufficiently serious to account for the highest incidence of skin disease. Approximately one-third of all patients in the United States seen by dermatologists have eczema. This category of skin disease includes atopic dermatitis, lichen simplex chronicus, prurigo nodularis, stasis dermatitis, nummular eczematous dermatitis, dyshidrotic eczematous dermatitis, seborrheic dermatitis, and "eczematous-like" eruptions often accompanying systemic diseases such as Wiskott-Aldrich syndrome, X-linked agammaglobulinemia, phenylketonuria, ahistidinemia, Hurler's syndrome, Hartnup disease, and acrodermatitis enteropathica. In addition, this category includes eczematous dermatitis caused by allergic contact, photoallergic contact, and polymorphous light-induced eruption, as well as infections eczematoid dermatitis and eczematous dermatophytosis.

For acute diseases such as allergic and irritant contact dermatitis, the inflammatory reaction can be prevented by prophylactic application of suitable pharmacological agents, either alone or in combination with a penetration blocking agent. Examples of suitable pharmacological agents include immunosuppressants, TNF-inhibitors, ion modulators, antihistamines, cAMP modulating agents, and neuropeptide and neurotransmitter antagonists. In a preferred embodiment, IFN-$\alpha$ or IFN-$\alpha_2$ is administered in combination with iontophoresis to provide additional therapeutic advantages. IFN-$\alpha$ serves to counteract the TNF that is secreted from the lamellar bodies and that can exacerbate the symptoms of skin disease. Additionally, the iontophoresis and/or the pharmacological intervention can be combined with occlusion. In another preferred embodiment, a diuretic such as furosemide or spironolactone is administered in a topical preparation to afflicted skin. In still another preferred embodiment a TNF-inhibitor such as verapamil or isradipine is administered topically to diseased skin. Also in a preferred embodiment anti-diarrheal agents such as loperamide or diphenoxylate is administered topically to diseased skin or use as prophylactic regimen.

In additon, skin disease is frequently associated with perturbations of the skin's barrier properties and hence, elevated levels of water loss. As described above, this water loss may serve to accelerate the lamellar body extrusion process and hence, the cellular growth rate associated with skin diseases. Without being limited to a particular mechanism, the therapeutical goal in the treatment of certain skin diseases may involve stabilizing the lamellar body extrusion process and/or homeostatic intracellular ion concentrations, so that the epidermal barrier can gradually recover, preventing further water loss and thus, maintaining local ion concentration and the rate of lamellar body extrusion, and keeping the skin inflammatory/immunological responses at quiescent state. This stabilization can be brought about through the use of suppressing ion current electrotransport therapy, sonophoresis, and/or pharmacological intervention.

C. The Treatment of Skin Cancers

The methods described herein can be applied to the treatment for a variety of dermal or epidermal skin cancers, that are benign or malignant, of viral origin, bacterial, or other origin, including but not limited to primary malignant melanoma, basal cell carcinoma, squamous cell carcinoma, mycosis fungoides lymphoma, and Kaposi's sarcoma.

Primary malignant melanoma of the skin is the leading cause of death from all diseases arising in the skin. There has been a disturbing increase in the incidence of primary melanoma of the skin. The rate has doubled in the past 10 years, possible due to increased "weekend" exposure to sunlight. Primary cutaneous malignant melanoma, moreover, does not respond or responds only poorly to chemotherapy or radiation therapy, and, so far, hope for survival has been based on surgical excision during the very primary stages before deep invasion occurs.

Basal cell carcinoma accounts for over 75% of all skin cancers. These carcinomas arise from the epidermis, cytologically resemble the normal basal cells, and show little tendency to undergo the usual differentiation into squamous cells which produce keratins. Although these tumors very rarely metastasize, they are locally invasive and, if neglected, may invade widely and deeply into underlying structures, including nerves, bone, and brain.

Squamous cell carcinoma also arises from the epidermis but shows significant squamous differentiation and usually keratin production. These tumors have a variable tendency to metastasize, depending upon their size, extent of invasion, location, and whether they arise from a premalignant lesion, a burn scar, a chronic inflammatory condition, or from apparently normal skin.

Mycosis fungoides lymphoma is the most common lymphoma of the skin and begins with cutaneous lesions, usually with no evidence of visceral infiltration for several years. The initial lesions may be clinically confused with eczema, contact dermatitis, or psoriasis.

Kaposi's sarcoma is a frequent skin neoplasm that occurs in humans infected with HIV-1. It is a complex neoplasm that includes proliferating endothelial cells accompanied by large numbers of factor 13 positive dermal dendrocytes (see Nickoloff (1989) *Science* 243:1736–1737). Kaposi's sarcoma may result from a disordered cytokine network. See Nickoloff (1989) *Autoimmunity Forum* 1:2–5. Hence, connecting this cytokine network may result in regression of the angiogenic tissue response and the accumulation of factor 13a positive dermal dendrocytes. It is known that Kaposi's sarcoma lesions are responsive to the rise of interferon injections.

Thus, the methods of the present invention provide for the local activation of keratinocytes can initiate the natural defense mechanism to treat abnormal cell growth (various cancers and tumors) of the skin. In addition, the lamellar body extrusion process may also increase the rate of release of preformed proinflammatory cytokines, such as IL-1 and TNF, and thus, decrease the rate of neoplastic cellular growth. This can be accomplished by modulating the ion flux, ion gradients, or cellular concentrations of ions in the skin, for example, by using electrotransport, or sonophoresis, or with pharmacological intervention or with combination of pharmacological agents and iontophoresis, or with sonophoresis. In addition, several different compounds are said to work in synergy with TNF, e.g., $\gamma$-interferon, histamine, substance P, leukotriene B4, and the like. The co-administration of these synergistic substances with an enhancing electric current will provide an effective method for treating skin cancers.

D. The Treatment of Wounds

The major cause of chronic wounds is poor local blood circulation (ischemia) which leads to tissue infarction followed by secondary infection. A partial list of the causes of chronic ulcers of the skin includes circulatory disturbances, such as varicose veins and obliterative arterial disease, extensive injury from frostbite or burns, trophic changes accompanying many neurologic disorders, bedsores or decubiti, systemic diseases such as sickle cell disease, neoplasms, diabetes and various infections. See PROGRESS IN CLINICAL AND BIOLOGICAL RESEARCH, Vol. 365, "Clinical and Experimental Approaches to Dermal and Epidermal Repair: Normal and Chronic Wounds", Barbul et al. (eds.), Wiley-Liss, Inc., (1991). No matter what the underlying cause, secondary infection is very likely to occur and to interfere with healing, complicate grafting or other restorative procedures, or produce extension of the process.

Current therapies for chronic wounds include debridement to remove the necrotic and possibly infected tissue and subsequently, promoting wound repair. Another therapeutic regimen which is presently under clinical development is skin or epidermal allographs. These treatment regimens involve major surgical procedures and significant medical costs and health risks.

The methods described herein provide a low-cost, non-surgical procedure for the treatment of wounds. Specifically, the release of neuropeptides and neurotransmitters from peripheral free nerve endings and the activation of the keratinocytes by either pharmacological means (e.g. digoxin) or electrical means will initiate antigen-independent local skin inflammatory responses and the release of proinflammatory cytokines from lamellar granules. The release of TNF and IL-1 by the activated keratinocytes further leads to the production of TGF-$\alpha$ (transforming growth factor-alpha) which up regulates keratinocyte growth and thus, regeneration of the epidermis. The release of TNF also can induce the local angiogenesis process. In addition, IL-1 is a potent growth factor for both keratinocytes and fibroblasts. When applied exogenously, IL-1 stimulates both partial and full thickness wound repair in pigs via inducing the re-epithelization process.

The release of these proinflammatory cytokines can be accomplished by using sonophoresis, iontophoresis with an enhancing current, either alone or in combination with other pharmacologically active agents (e.g., growth factors such as fibroblast growth factor, epidermal growth factor, platelet-derived growth factor, and other therapeutic agents which mimic the biological function of these factors, and antibiotics).

Since the goal in treatment of wounds is to achieve the normal epidermal/dermal homeostasis, in some embodiments, the above methods frequently will be combined with the means for maintaining the lamellar body extrusion rate as described above. Specifically, occlusion or the modulation of local ion concentration (either actively via electrical mobilization from the device, passively by incorporating of specific ions into the occlusive dressing, or actively followed by passively for maintenance therapy) or the co-administration of pharmacological agents capable of regulating the local ion flux, ion gradients, or cellular concentrations of ions, such as channel blockers or channel openers, will be utilized in conjunction with the methods described above.

E. The Treatment of Ocular Inflammation

The TNF inhibitors described above, can also be applied to the treatment of ocular inflammation, including inflammation accompanying the administration of various irritating ophthalmic solutions (see e.g., PCT Patent Application No. WO 93/1876 to Giovanoni, which is incorporated herein by reference). The agents discussed herein may be applied to the eye before the application of the irritating ophthalmic solution, included with the irritating ophthalmic solution being applied or applied after the onset of an ocular inflammatory response associated with the irritating ophthalmic solution.

The TNF inhibitors may be applied to the eye in the form of a solution, suspension, ointment, in a pack, by intracameral, subconjunctival or retrobulbar injection, or iontophoretically. Typically, a solution is preferred, the solution having a viscosity between about 15–25 centipoise for patient comfort. The solution, suspension or ointment will typically include a sterile, isotonic solution which may further include preservatives and/or antioxidants. Typical solutions are made from sodium chloride or boric acid, benzalkonium chloride, phenylmercuric nitrate, sodium EDTA or disodium phosphate, and sterile distilled water. In addition, the pH will be adjusted to provide optimal stability and patient comfort. The solution is then sterilized using standard procedures (see, e.g., REMINGTON'S PHARMACEUTICAL SCIENCES, supra).

The solution may contain additionally a variety of substances directed to specific applications, such as, but not limited to, diagnostic aids (e.g., dyes for visualizing structures and abnormalities not readily visible upon inspection), anesthetics (e.g. benoxinate hydrochloride, proparacaine hydrochloride and tetracaine hydrochloride), mydriatics (substances which dilate the pupil such as, e.g., atropine sulfate, homatropine hydrobromide, phenylephrine, scopolamine hydrobromide and cylcopentolate), miotics (agents which constrict the pupil, such as, e.g., demecarium bromide, echothiophate iodide and pilocarpine hydrochloride or nitrate), astringents, demulcents (agents which sooth or relieve irritation) and lubricants. Other substances will be apparent to those of skill in the art.

F. Treatment of Inflammation Associated With Cosmetics or Skin Care Products The compounds of the invention can also be used to alleviate skin sensitization, irritation or inflammation associated with cosmetics or skin care products. Preferably the compounds are TNF-inhibitors or ion modulating agents such as $La^{+3}$. The TNF inhibitors or antiinflammatory agents described herein can be used before, during or in response to skin sensitization, irritation or inflammation associated with cosmetics or skin care products.

Typical skin care products and cosmetics which may cause adverse skin reactions such as sensitization, irritation or inflammation include depilatories such as described in U.S. Pat. Nos. 5,271,942 and 5,296,472; hair color treatments such as described in U.S. Pat. No. 5,318,776; antiperspirants such as disclosed in U.S. Pat. No. 5,298,236; fragrances, such as discussed in U.S. Pat. No. 5,297,732 and 5,278,141. Each of these patent disclosures is incorporated herein by reference. Other cosmetics include, e.g., creams, lotions, sunscreens, make-up preparations, face powders, lipsticks, mascaras, eye shadows, nail products, hair preparations, bath products, shaving preparations, soaps, and toothpastes. These compositions are formed using methods well known in the chemical arts see, e.g., THEe KIRK-OTHMER ENCYCLOPEDIA OF CHEMICAL TECHNOLOGY, 3rd Ed., Vol. 7 (Wiley Interscience 1979), which is incorporated herein by reference.

G. The Treatment of Systemic Inflammatory Conditions

While the pathogenesis of various systemic inflammatory disorder is still unknown, it has been shown by many studies that the proinflammatory cytokine TNF is the key mediator orchestrating the inflammatory and the immunological components of these diseases. These systemic conditions include rheumatoid arthritis (RA), inflammatory bowel diseases (IBD), transplantation, graft-versus-host reactions, cachexia (wasting syndrome) associated with cancer and AIDS, etc.

For example, RA is a common systemic, autoimmune, inflammatory disorder expressed most commonly in the joints. As a highly variable disease, clinical manifestation ranges from a mild paucistricular form of brief duration to a relentless, progressive, destructive polyarthritis associated with systemic features. Frequently, RA is heralded by prodromal symptoms, such as fatigue, anorexia, weakness, and generally aching and stiffness that are not clearly localized to the articular structure. Elevated levels of inflammatory and proinflammatory mediators have been found in the inflamed joints of patients with RA. On the other hand, IBD, including ulcerative colitis and Crohn's disease, which affects children and adolescent population, is largely associated with pain, distressing toilet habits, retardation of growth and suppression of pubertal development. Similar to RA, various inflammatory and proinflammatory mediators are found in the intestinal mucosa, and in the feces of patients with IBD. However, recent clinical results demonstrate a clear resolution of both severe RA and IBD upon administration of anti-TNF antibody. Another systemic condition, i.e., cachexia (wasting syndrome) has an adverse impact on the lives of many patients in the advanced stage of cancer and AIDS. Pentoxifylline and thalidomide have both been shown to be effective in reducing TNF activities in vitro and were both effective in vivo in improving cachexia conditions in cancer and AIDS patients respectively. Therefore, TNF has been found to be the key mediator in many systemic inflammatory conditions including RA, IBD, cachexia, infection, adult respiratory distress syndrome, asthma and others.

The methods of the present invention provide means for suppressing TNF production in various systemic pathological conditions using the compounds identified herein.

In order that the invention described herein may be more fully understood, the following examples are set forth. It should be understood that these examples are for illustrative purposes only, and are not to be construed as limiting this invention in any manner. Those skilled in the art will readily appreciate a variety of noncritical parameters which could be changed or modified to yield essentially similar results.

V. EXAMPLES

A. Animal Models

Example: Induction of Skin Inflammation and Hyperplastic Responses by Topical TPA Treatment The effects of the application of TPA to the skin have been well characterized in the literature. This activator of protein kinase C results in an inflammatory response that persists for 72 hours or more. It is characterized initially by edema formation and at later time points by epidermal hyperplasia and grossly evident redness and scaling. The biochemical and morphologic alterations accompanying TPA treatment bear many similarities to psoriasis.

The ability of TPA treatment to stimulate the expression of cytokine messenger RNA (mRNA) in hairless mouse skin was examined in a preliminary time course study. The results of this experiment were analyzed by standard RT-PCR techniques on mRNA extracted from whole skin. The expression of $\beta$-actin, a housekeeping gene whose expression is relatively constant under treatment conditions, was measured to provide a baseline against which the TNF mRNA could be quantitated. As compared to $\beta$-actin levels, which remained essentially constant throughout the experimental time course, TNF mRNA expression showed marked differences at various time points. TNF mRNA levels were elevated at 2 hours, with peak expression was seen at 5 hours, and a return to control levels was observed by 20 hours.

The ability of TPA to upregulate the mRNA expression of other proinflammatory mediators was also evaluated. For IL-1$\alpha$, no change in mRNA levels was evident at the 2 hour time point, but a marked elevation was detected at 5 hours. A similar profile of mRNA expression was observed for KC, a mediator thought to be the murine equivalent of IL-8 (a lymphocyte and neutrophil chemoattractant). KC mRNA levels were also unchanged at 2 hours, but were substantially elevated at 5 hours. Like TNF, the mRNA levels of IL-1$\alpha$ and KC had returned to background levels at a 20 hour time point. Interestingly, mRNA for IL-10, a cytokine with anti-inflammatory properties, was not detectable at any of the time points examined. Lastly, TPA treatment of the skin caused the induction of ICAM-1 protein expression. Frozen skin sections were immunostained with a specific anti-ICAM-1 antibody and showed little or no expression of ICAM-1 at the 2 and 5 hour time points, but were strongly positive for ICAM-1 at the later time points, 20 and 44 hours post-TPA treatment.

Because of its extensive characterization in the literature, its similarity to psoriasis, and the relative ease with which the experiments can be performed, the TPA treatment protocol was pursued as a model of skin inflammation. Detailed time course studies were therefore performed to determine the time point after TPA treatment at which TNF mRNA levels are maximal. This is of importance since TNF mRNA expression kinetics characteristically show a rapid induction phase, followed by a rapid disappearance. In an experiment examining the 0.5, 1, 2, 3, and 4 hour time points, TPA-induced mRNA levels reached a peak at the 3 hour time point and were on the decline by 4 hours. The 3 hour time point was therefore chosen for use in further studies.

In addition to assessing the cytokine mRNA levels, the time course of the TPA-induced increase in skin thickness was also evaluated. This measurement was made with a micrometer using skin excised from euthanized mice. While a minimal change in skin thickness was evident at the 2 hour and 4 hour time points, a dramatic increase was observed 6 hours after TPA treatment. Further increases were typically seen 8 hours with this response being maintained through the 24 hour time point.

The time course of cytokine protein production in response to application of TPA to hairless mouse skin was also evaluated. Skin samples excised from euthanized mice were flash frozen and stored at −70° C. until analysis. To process the tissue, it was homogenized and sonicated on ice in phosphate buffered saline containing a mixture of protease inhibitors. Particulate material was pelleted by centrifugation and the supernatant was analyzed by specific ELISAs for murine TNF and IL-1$\beta$. As compared to vehicle-treated tissue, the TPA treated skin showed little change in TNF content through the 6 hour time point. At 8 hours, however, a large increase in the TNF concentration of the homogenized skin was observed (approximately 300 pg/mL TNF) with lower levels of TNF being observed at the 16 hour and 24 hour time points (approximately 175 pg/ml).

The profile of expression of IL-1$\beta$ protein in TPA-treated skin was slightly different. Increases in IL-1$\beta$ concentrations were gradually evident at 4 hours and 6 hours post-TPA, with the greatest increase being evident at the 8 hour time point (approximately 425 pg/ml). This IL-1$\beta$ concentration was maintained at 16 hours and declined by approximately half at 24 hours.

As a confirmation of the above-described protocol, in vivo experiments were conducted with hairless mice in an effort to inhibit TPA-induced inflammation with verapamil. After a pilot study showed a reduction in TPA-induced TNF mRNA expression upon verapamil treatment in a single mouse, a larger study was conducted using 4 mice with 3 sites each being treated as 1) control, 2) vehicle, 3) verapamil alone (4% w/v in ethanol), 4) TPA alone, and 5) TPA+verapamil. Verapamil was applied to the skin the afternoon prior to the experiment, 2–3 hours before the application of TPA, and concomitant with TPA application. Three of the mice were euthanized at the 3 hour time point, and the treated sites were analyzed for TNF mRNA by RT-PCR. The fourth mouse was euthanized at a 24 hour time point, and the thickness of the treated areas of skin was measured using a micrometer.

The results of the RT-PCR analysis demonstrate that the low levels of TNF mRNA expression in control skin were unchanged or slightly reduced by treatment of the skin with vehicle (2.5% DMSO in ethanol) or verapamil alone. Application of TPA to the skin caused a substantial increase (104%–163%) of the TNF mRNA levels. Treatment of the TPA sites with verapamil resulted in a significant reduction (p<0.01, paired Student's t test) in skin TNF mRNA levels as compared to TPA alone. In addition, the RNA samples from one of the three mice were also analyzed for the presence of IL-1$\alpha$ and KC mRNA by RT-PCR. These results showed that, similar to the TNF mRNA results, verapamil caused some reduction in TPA-induced IL-1$\alpha$ mRNA expression and a significant suppression (p=0.04, paired Student's t test) in KC mRNA levels. Twenty-four hours after TPA application to the skin, the TPA sites looked markedly swollen and edematous as compared to the control sites, while the TPA+verapamil sites were more normal in appearance. These visual observations were confirmed by the micrometer measurements, which demonstrated that verapamil afforded a substantial reduction in the extent of TPA-induced increase in skin thickness. Compared to skin treated with TPA alone, combined treatment with TPA+ verapamil resulted complete suppression of skin swelling response.

Figure 2:
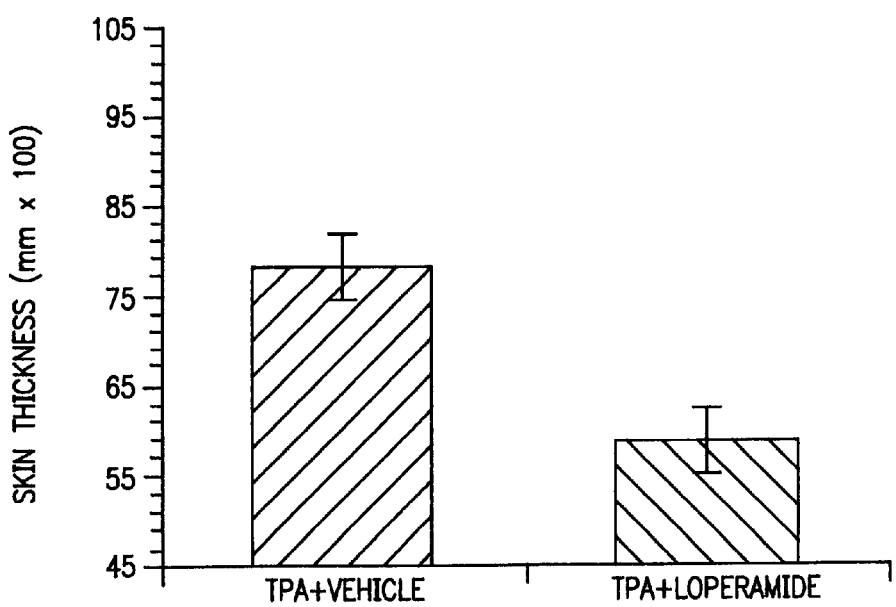
FIG. 2 illustrates the ability of loperamide to suppress inflammation in TPA-treated mouse skin.

A slightly different protocol was used in an effort to determine whether the drug loperamide would also exert an anti-inflammatory effect on TPA-treated hairless mouse skin. Loperamide (7.5% solution in 70% propylene glycol/ 30% ethanol) was applied the afternoon before, 2 hours before, and just after application of TPA. At the 8 hours time point, the mice were euthanized, the treated areas of skin were excised, and the thickness of the skin was measured using a micrometer. The results demonstrated that the thickness of skin treated with loperamide alone was unchanged as compared to vehicle-treated skin. A substantial increase in skin swelling was observed upon TPA treatment, with a thickness of 0.56 mm being measured for the TPA sites as compared to 0.36 mm for vehicle-treated sites. Application of loperamide to TPA-treated skin sites was found to completely inhibit the TPA-induced increase in skin thickness at the 8 hour time point, with a 0.39 mm thickness being measured for the TPA+loperamide group (not statistically different from the vehicle-treated skin). The anti-inflammatory effects of loperamide were confirmed in a second experiment. In this study, skin thickness was observed to increase from 0.39 mm for vehicle-treated skin to 0.89 mm for the TPA-treated sites. Application of loperamide inhibited the TPA-induced swelling response by 64%, with a thickness of 0.57 mm being observed for this group (p<0.01 vs. TPA alone, Student's t test). See FIG. 2. Similarly, application of furosemide inhibited TPA-induced swelling response.

Example: Induction of Hypersensitivity in Mice Using DNCB

Allergic contact hypersensitivity (CH) is a clinically important type of dermatitis that can occur as a result of exposure to occupational or environmental agents. A number of chemicals can be used to experimentally reproduce this phenomenon. The sequence of events following initial application of a contact allergen to the skin (sensitization phase) is thought to involve presentation of the allergen in association with MHC class II molecules by the Langerhans cells (LCs). The LC migrate to the regional lymph nodes where they stimulate antigen-specific T cell proliferation. When the allergen is reapplied to the skin several days later (challenge phase), an allergic reaction occurs that takes 24–48 hours to develop. This type of response is termed delayed type hypersensitivity in contrast to the immediate hypersensitivity mediated by mast cell degranulation.

Numerous studies in the literature have described CH in mice as well as the ability of drugs to inhibit it, with ear thickness and histologic appearance of the ear tissue being the primary endpoints examined. Similar to what has been commonly reported by other investigators, the specific protocol used in these studies involved the application of DNCB (in an acetone:olive oil 4:1 vehicle) to the skin on the posterior portion of the back of hairless mice. Five days later, DNCB was applied to the dorsal surface of the ears. At the indicated time point, the mice were euthanized, ear thickness was measured, and the samples were processed for either RNA extraction, protein analysis, or histology.

Figure 3:
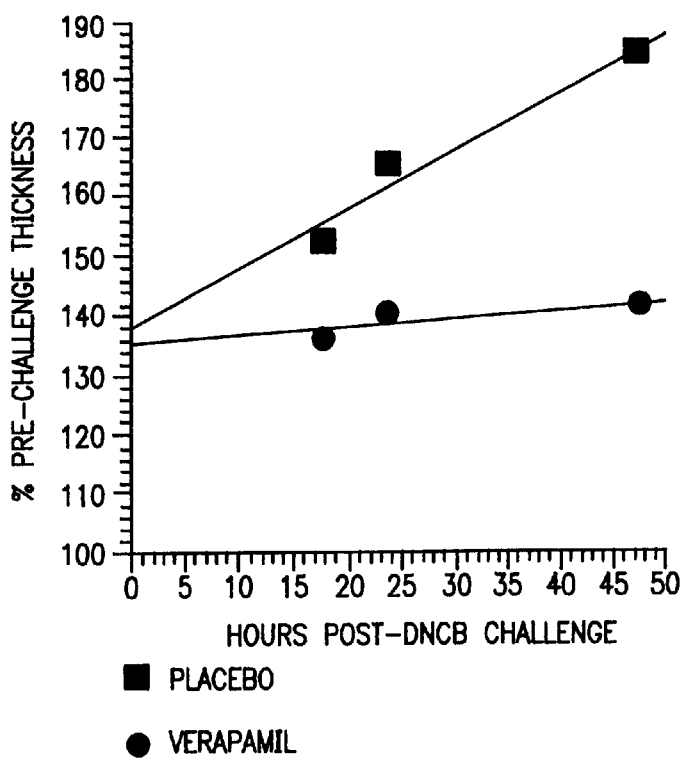
FIG. 3 illustrates the ability of verapamil to suppress inflammation in DNCB-treated mouse skin.

Experiments were carried out in an effort to inhibit the DNCB-induced immune reaction with various drugs. An initial experiment was performed in which verapamil (4% w/v in 70% propylene glycol:30% ethanol) was applied to the dorsal and ventral surfaces of the right ear 2 hours before, 1 hour after, and 6 hours after DNCB challenge. The left ear was similarly treated with vehicle. The results showed some suppression in swelling of the right ear. A repeated experiment, using a larger number of mice (n=6) and a slightly higher concentration of verapamil (5% w/v), showed that ear swelling was significantly reduced. See FIG. 3.

Figure 4:
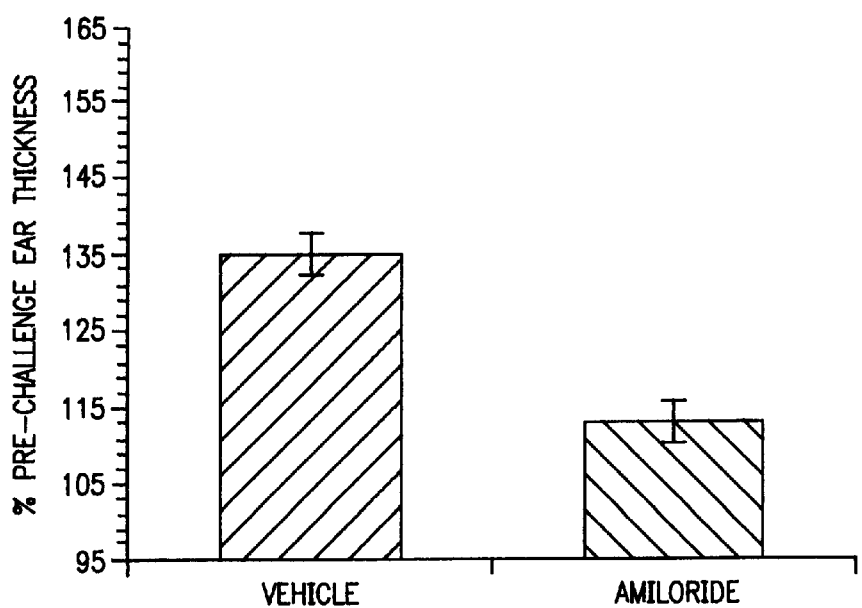
FIG. 4 illustrates the ability of amiloride to suppress inflammation in DNCB-treated mouse skin.

The ability of amiloride to suppress DNCB-induced ear swelling was also examined. In these experiments, mice were sensitized with DNCB, and, five days later, amiloride (2% w/v in 70% propylene glycol: 30% ethanol) was applied to the right ear and vehicle to the left ear 30 minutes and 8 hours after DNCB challenge. The drug was found to cause a significant decrease in the extent of DNCB-induced ear swelling (p<0.002, paired Student's t test), with ear thickness measurements of 135% of pre-challenge values for the ears treated with DNCB alone and 113% for ears treated with DNCB+amiloride. See FIG. 4.

Additional experiments were performed in which BALB/c mice were used to carefully evaluate the time course of ear swelling as well as the time course of cytokine protein expression in the DNCB contact hypersensitivity model. In these experiments, a significant increase in ear thickness was observed 18 hours post-DNCB challenge, peak swelling occurred at 30 hours, and the response was maintained through a 72 hour time course. These ear samples were homogenized and sonicated in the presence of protease inhibitors and analyzed for TNF and IL-1β by specific ELISA. The time course of cytokine expression was somewhat different from that of the ear swelling response. As compared to the contralateral ear treated with DNCB vehicle, the DNCB-treated ears showed the greatest elevations in TNF concentrations at the 48–60 hour time points, with a decline being evident at the 72 hour time point. A similar profile was seen for IL-1β protein expression. The highest concentrations were observed to occur 48–60 hours post-DNCB treatment, with lower levels being expressed 72 hours post-challenge.

Example: Compromised Skin Barrier Model: Acetone Treatment and Detection of TNF mRNA levels by RT-PCR Hairless mice between 2–3 months of age were obtained from Simonsen Laboratories (Gilroy, Calif.). The animals were housed under standard conditions with a 12 hour light/dark cycle and free access to food and water. The mice were anesthetized with an intraperitoneal (IP) injection of a mixture of Anased and Ketaset (0.15 mg and 3 mg per mouse, respectively). Cotton balls were soaked in acetone and gently rolled along the right flank for approximately 10 minutes. The left flank was similarly treated with a saline-soaked cotton ball. At a 2 hour time point, the mouse was euthanized by carbon dioxide asphyxiation. The control and acetone-treated areas of skin were removed and frozen on dry ice. RNA was extracted from the skin, and TNF mRNA levels were analyzed by standard RT-PCR-procedures as described above. The expression of β-actin was also examined by RT-PCR, with this control gene being used to correct for the quantity of mRNA used in the reactions. The results of the acetone treatment demonstrated that, at a 2 hour time point, saline-treated skin showed little or no TNF mRNA expression, while a marked induction of TNF mRNA was evident in the acetone-treated skin.

B. Determination of Ton Concentrations

The quantities of ions at each stratum of the skin (one micron, horizontal cryo-sections) can be analyzed either with elemental analysis, via atomic absorption spectroscopy, or through electron probe analysis in conjunction with analytical electron microscopy. See, e.g., Warner et al. (1988) *J. Invest. Dermatol.* 90:78–85.

C. Determination of Cytokine Levels

The level of the proinflammatory cytokines, e.g., IL-1 and TNF, at each stratum of the skin can be measured semi-quantitatively by immunohistochemical staining of the whole skin tissue or quantitatively using standard, commercially available ELISA kits (Genzyme Cambridge, Mass. or R&D Systems, Minneapolis, Minn.). Quantitative measurement of cytokines at the protein level can also be accomplished by Western blot analyses. The actual biological activities of these cytokines can be characterized using the established cytotoxicity assays specific for TNF (e.g., WEHI-164 cell line) and IL-1, respectively. In addition, the level of TNF production may be determined by measuring the level of the mRNA corresponding to TNF using PCR and Northern blot techniques as described above. Generally, the skin is challenged to produce an inflammatory response and the levels of cytokines are measured. Three examples of these techniques are provided below.

Example: Isolation of Lamellar Bodies (LB) and the Detection of TNF and IL-1α in LBs and Skin
LB Isolation One hundred fifty to two hundred neonatal ICR Swiss albino mice (born within 24 hours) were injected with 20–25 µg each of pure staphylococcal exfoliative toxin (Toxin Technology Inc.) in DEH solution (10 mM EDTA; 20 mM HEPES(N-(2-Hydroxyethyl)piperazine-N'-(2-ethanesulfonic acid)) (Sigma); 1 mM phenyl methyl sulfonyl fluoride (Sigma) in Dulbecco's modified Eagle's medium (DMEM, Gibco) pH 6.5) and incubated at 34° C. for 1–2 hours. Outer epidermal sheets were collected in DEH on ice and quickly drained of excess liquid. The sheets were placed on a covered plastic petri dish filled with ice and diced fine with a razor blade. The diced sheets were homogenized in an ice-cold, loose-fitting glass homogenizer with approx. 30 mL DEH. After filtering through cheese cloth, the filtrate was ruptured in a Stansted cell disrupter at 5000 pounds-per-square-inch. The post-Stansted homogenate was centrifuged at 700 g for 10 minutes and the supernatant passed through a glass fiber pre-filter and a series of nucleopore filters of: 8.0, 3.0, 1.0, 0.8, 0.6 and 0.4 µm pore size. The final filtrate was pelleted at 20,000 g for 25 minutes.

Detection of TNF in the LB

In a typical experiment, LB fractions were solubilized in sodium dodecyl sulfate-polyacrylamide gel electrophoresis (SDS-PAGE) sample buffer which was incubated at 100° C. for 5 minutes and the insoluble material pelleted by centrifugation in a microphage. Solubilized fractions were run on 15% polyacrylamide gels by standard SDS-PAGE procedures and then transblotted onto nylon membranes. The transferred proteins were subjected to incubation with anti-TNF antibody according to typical Western blotting protocols and bands demonstrating specific antibody binding were visualized by a peroxidase-induced color reaction product (nitroblue tetrazolium, magnesium chloride and 5-bromo-4chloro-3-indoyl phosphate; BioRad).

The results of these studies demonstrated the presence of a 17 kD (kiloDalton) band in the LB solubilized proteins, which represents the mature form, i.e., the secretory form, of TNF. The specificity of the 17 kD band was confirmed by molecular weight standards and comparison to recombinant TNF expressed by *Escherichia coli* run parallel on the same blot. Lipopolysaccharide (LPS)-stimulated RAW cells were characterized by a band at 17 kD as well as one at 26 kD; the band at 26 kD represents the membrane-bound precursor form of TNF. In contrast, RAW cell medium contains only the 17 kD, secretory form. LB's appear, also, to be lacking the membrane-bound form. These results suggest that LB's contain TNF packaged in its mature and secretory form, thus facilitating the release of active, soluble TNF into the SC/SG interface immediately upon LB fusion with the apical plasma membrane of the outermost granular cells.

Detection of IL-1α in LB

Transblots of the same protein samples as above are used for the determination of IL-1α. Both RAW cells and LB displayed immunoreactive bands at approximately 15 kD and 23 kD. The LB preparation, in addition showed a band at approximately 17–18 kD, whereas the RAW cells were characterized by a heavily labeled band at 32 kD. The 15 kD band is very likely a proteolytic cleavage product and the 17–18 kD band, the native mature form of IL-1α. The 23 kD band is considered to be the membrane-bound form of IL-1α and the 32 kD band the precursor form of IL-1α. These results indicate that LBs contain the secretory form as well the membrane-bound form of IL-1α; whereas, RAW cells contain the membrane-bound form as well as the precursor form of IL-1α.

Immunohistochemical Localization of TNF in Phorbol Ester-Stimulated Murine Skin

Hairless mouse skin was treated topically with TPA in DMSO/ethanol for various lengths of time, or with DMSO/ethanol alone, and was subsequently biopsied and either frozen immediately in a polyvinyl alcohol based embedding medium (OCT compound, Miles) and stored at −70° C. or fixed in 2% paraformaldehyde, lysine, sodium metaperiodate in cacodylate buffer (PLC) for 2 hours, followed by immersion in a cryoprotectant buffer (e.g., 7% sucrose, 10% glycerol in cacodylate buffer) before freezing in OCT. The skin samples were sectioned in a cryostat and were used for immunohistochemical localization of TNF. A polyclonal rabbit anti-mouse TNF antibody (Genzyme) was used to localize TNF. The antibody was employed at titers of 1:100–1:10,000, along with the Vectastain ABC elite kit (Vector laboratories) and either AEC (3-amino9-ethylcarbazole), DAB (3,3'-diaminobenzidine), or silver-enhanced Auroprobe streptavidin (Amersham) end products. Slides were visualized and photographed in a Nikon Optiphot light microscope.

The results demonstrated striking differential labeling patterns suggesting: (1) dense outer epidermal localization consistent with LB localization, (2) dermal/epidermal junction labeling, and (3) labeling of follicles, sebaceous glands, endothelial cells and dermal dendritic cells. The dramatic modulation in labelling pattern after TPA treatment, from a strictly SC/SG localization to a more diffuse epidermal localization, along with the lack of labeling in control sections treated with normal rabbit IgG instead of antiserum, suggests that the label is due solely to antibody binding.

Immunohistochemical Localization of IL-1α in Phorbol Ester-Stimulated Murine Skin The same tissue sections used above showed similar labeling patterns when incubated with a polyclonal anti-mouse IL-1α antibody (Genzyme). The localization, in untreated samples, of label to the SC/SG interface was perhaps more striking than for TNF. A similar loss of density in the SC/SG region following TPA treatment with a concomitant increase deeper into the nucleated cell layers suggests a similar mode of action for these two cytokines following TPA treatment. Like TNF, IL-1α demonstrated also an increased density in the outer epidermis after 8 hours of TPA treatment. TPA-treated or untreated control samples demonstrated low background levels of labeling after incubation with a normal rabbit IgG instead of antiserum.

D. Induction of Transepidermal Water Loss

To determine the ability of compounds or methods described herein to increase or decrease the rate of barrier recovery during transepidermal water loss (TEWL), and thereby measure the "quality" of the skin with respect to the passage of water, and standard procedures used to disrupt the stratum corneum layer of the skin (e.g., the application of acetone to the skin). The time required for restoration of normal barrier function was also determined. Treatment of skin with sodium laurel sulfate (SLS) under occlusion (1.5 mg/cm$^2$ in saline) for a period of 7 to 20 hours was found to produce 20- to 200-fold increases in TEWL. Overnight exposure to SLS was found to be preferred. Barrier recovery was determined to be about 50% completed within two days following exposure.

E. Inhibition of Proinflammatory Cytokine Production in Cells

The abilities of several compounds to inhibit TNF, IL-1α and IL-1β release in stimulated cells, including THP-1 cells, RAW cells and HEK cells were examined using methods described below. The results are summarized in Table I below for the inhibition of TNF. The compounds studied included verapamil, nicardipine, isradipine, RO 20-1724, loperamide, Rec 15/2375, diphenoxylate, amiloride, spironolactone, thalidomide, pentoxifylline, terbutaline and furosemide. A control (dexamethasone) was included.

1. Inhibition of LPS-stimulated TNF Production in the Human Monocytic Cell Line, THP-1 Cell Culture Materials and Methods Cells were obtained from ATCC and cultured in RPMI containing 10% fetal bovine serum, 2 mM L-glutamine, 25 mM HEPES, and 50 μM 2-mercaptoethanol. Cultures were maintained by the addition of fresh growth medium to a T-75 or T-150 flask of cells in suspension, or by pelleting the cells and re-suspending them in the appropriate volume of fresh medium. Maximum cell density was $1.0 \times 10^6$ cells per mL and cultures were seeded at a minimum density of $0.2 \times 10^6$ cells per ml.

Experimental Conditions

THP-1 cells were plated into 24well plates at a density of $1.0 \times 10^6$ cells per mL in 0.5 mL medium per well. For measurement of TNF production, THP-1 cells were typically incubated with 1 μg/mL LPS, with and without a test compound, for a 6-hr period at the end of which the cell suspensions were spun down to retrieve the cell-free supernatant for subsequent measurement of secreted TNF. For measurement of IL-1α and IL-1β production, THP-1 cells were incubated with 500 ng/mL or 50 ng/mL LPS and incubated for 16 hours. Levels of secreted cytokine were measured in cell supernatants as for TNF. Cell-associated species were measured in cell lysates which were prepared by repetitive freeze-thawing of cells. For in vitro screening, drugs at 10 μM concentration were co-administered with LPS. The corticosteroid, dexamethasone, a known efficacious anti-inflammatory drug, was used as a positive control for inhibition of the LPS response in our experiments. Drug effects on cell viability were assessed by the MTT assay. Drugs were prepared in a vehicle which allows for their complete dissolution, such as DMSO (for amiloride, for example) or ethanol (for verapamil, for example). Water-soluble drugs were dissolved in aqueous solutions such as RPMI or deionized H$_2$O. The final concentration of DMSO in the incubation medium was at or below 0.01% and that of ethanol was at or below 0.1%. The effect on cell viability was evaluated by the MTT assay.

Results

A number of drugs belonging to a variety of classes were tested for their effects on TNF production by LPS-stimulated THP-1 cells. These drugs included diuretics, calcium channel blockers, antidiarrheals, a specific inhibitor cAMP phosphodiesterase type IV inhibitor, calmodulin antagonists, and antitumor drugs. With respect to the inhibition of TNF production, amiloride (a potassium-sparing diuretic), (±)verapamil (a calcium channel blocker), loperamide (an antidiarrheal), and RO-20-1724 generated the most substantial and reproducible effects: a 40% inhibition by 10 μM amiloride, 54% inhibition by 10 μM (±)verapamil, 58% inhibition by 10 μM loperamide and 55% inhibition by RO-20-1724. The average inhibition achieved by the control drug, 10 μM dexamethasone, was 67%.

The effects of amiloride and verapamil on IL-1 production by THP-1 cells were also tested. Amiloride at a concentration of 10 μM was found to reduce the level of cell-associated and secreted IL-1α and IL-1β. (±)Verapamil was roughly equivalent on both the secreted and cell-associated forms of IL-1α and IL-1β (with a 40–50% inhibition of IL-1α levels and ~33% inhibition of IL-1β levels). Except for 10 μM dexamethasone and 10 μM hydrocortisone (another anti-inflammatory corticosteroid) which proved equally effective in both assays, the inhibitory effects of drugs were generally more extensive against LPS-stimulated production of TNF than IL-1α or IL-1β. Loperanide, (±)verapamil and amiloride did not impact on THP-1 cell viability at the highest dose tested, as indicated by MTT assay. Spironolactone (10 μM) was as effective as amiloride at inhibiting the THP-1 response to LPS for the production of TNF.

Further, nicardipine proved as effective as verapamil when tested once in THP-1 cells against LPS stimulated TNF production (56% inhibition). Nifedipine and diltiazem were much less effective upon initial testing whereas nimodipine was considered marginally effective at 10 μM concentration.

Compound RO-20-1724 (PDE IV inhibitor) on average produced a 55% inhibition of TNF levels in LPS-treated cells and, hence, appears comparable to verapamil and loperamide in its inhibitory activity. RO-20-1724 has been screened for its effect of IL-1 production by THP-1 cells stimulated with 50 ng/mL LPS and the resulting levels of secreted and cell-associated IL-1α and IL-1β indicated a 20 to 30% decrease compared to control (LPS alone).

A number of compounds with calmodulin antagonistic activity were also screened at 10 μM concentration in THP-1 cells, including W-7, calmidazolium and the anti-tumor drugs tamoxifen and nafoxidine. A reduction in secreted TNF levels by 40 to 50% was observed for W-7 and calmidazolium.

The inhibitory effects of verapamil as a function of drug dose were examined and indicated that 50% of the maximal inhibition achieved by verapamil (as defined by its effects at 10 μM) was reached at a dose of between about $1-5\times10^{-5}$ M ($IC_{50}$ value). The $IC_{50}$ values for amiloride and loperamide were found to occur within the same range.

2. Inhibition of LPS-stimulated TNF Production in the Mouse Macrophage Line, RAW 264.7 Cell Culture

Materials and Methods

RAW 264.7 cells were obtained from ATCC and cultured in DMEM, supplemented with 10% fetal calf serum and 25 mM HEPES in T-75 and T-150 flasks. Cells were passaged at confluence by scraping and routinely plated at a density of $0.25\times10^6$ and $0.5\times10^6$ cells per T-75 and T-150, respectively.

Experimental Conditions

Typically, RAW cells were plated at $0.25\times10^6$ cells per well of a 24-well plate, in 0.5 mL media per well on the day prior to experimentation. Drugs were prepared in a vehicle which allowed for their complete dissolution, such as DMSO (for amiloride, for example) or ethanol (for verapamil, for example). Water-soluble drugs were dissolved in aqueous solutions such as RPMI or deionized $H_2O$. The final concentration of DMSO in the incubation medium was at or below 0.03% and that of ethanol was at or below 0.1%. Drugs were co-administered with the stimulant, LPS. After a 6-hr incubation period with LPS±drug (n=3–4), the media from the experimental wells was harvested, the cells were removed by microcentrifugation, and the media assayed for TNF by ELISA. Drugs were screened at 10 μM for their ability to alter TNF production by cells stimulated with 1 μg/mL or 10 ng/mL LPS. Dexamethasone, an anti-inflammatory corticosteroid, served as the reference for inhibition of the LPS response. Compounds shown to produce a significant amount of inhibition of the LPS-induced response were subjected to further testing to determine the dose dependence of their effect.

Results

TNF was not detected in unstimulated RAW 264.7 cells. RAW 264.7 cells treated with LPS were stimulated to secrete TNF in a dose dependent fashion; cells treated with 1 μg/mL LPS produced on the order of 40 ng/mL to 150 ng/mL of secreted TNF as measured by ELISA. The results from in vitro screening experiments indicated that, in general, test compounds (as well as dexamethasone) were more effective at inhibiting the response elicited by the lower dose of 10 ng/mL LPS than the higher dose of 1 μg/ml.

The well-known and efficacious corticosteroid dexamethasone reproducibly inhibited the stimulated production of TNF in RAW cells, though not completely. On average, dexamethasone decreased the levels of secreted TNF by 60% compared to cells treated with LPS alone. Of the calcium channel blockers screened, the greatest inhibition was achieved by isradipine and nimodipine both of which appeared to be as effective as dexamethasone. Verapamil, nicardipine, and diltiazem produced a 40% to 50% inhibition of the response. Nifedipine was the least effective at the tested dose. Thus, we observed clear differences in the degree of inhibition achieved by the drugs in this class in LPS-stimulated RAW cells. In addition, the degree of inhibition achieved at 10 μM concentration of drug appeared also to be a function of the cell type. Hence, unlike what was observed in RAW cells, isradipine, nimodipine and diltiazem were much less effective as antagonists of the LPS stimulated production of TNF in THP-1 cells. On the other hand, verapamil (racemic and stereoisomers) was generally more effective as an inhibitor of the LPS-stimulated response in THP-1 cells than RAW cells. The difference in the inhibitory effects of drugs as a function of cell type (keratinocyte vs. monocyte vs. macrophage) may therefore be an important consideration with respect to the assessment of their therapeutic applicability given that the roles played by these various cells differs amongst the disease states being targeted.

A number of drugs classified as diuretics were also tested, and just as was found for the calcium channel blockers, considerable differences were seen amongst drugs of this class both within and between cell types used in the in vitro screen. For example, whereas amiloride was moderately effective in its inhibition of the LPS response in RAW cells, it was comparatively more effective in LPS-stimulated THP-1 cells at inhibiting TNF production. Unlike its effect in an initial THP-1 cell screen, minimal inhibition of TNF production was observed with bumetanide (a loop diuretic) in RAW cells. A tremendous decrease in the amount of TNF secreted by RAW cells was observed when hexamethylamiloride was co-administered with LPS.

Another amiloride congener, dimethylamiloride, achieved the same extent of inhibition as amiloride when screened side by side. Furosemide, another diuretic, was also comparable to amiloride in achieving inhibition of TNF secretion in stimulated RAW cells. Treatment of RAW cells with loperamide at 10 μM concentration also resulted in a lowering of TNF levels in RAW cell supernatants, though to a lesser degree than that which was observed in the THP-1 cells.

A number of drugs tested at 10 μM concentration achieved substantial inhibition of LPS (10 ng/ml)-stimulated TNF secretion by RAW264.7 cells, even comparable to that achieved by dexamethasone as indicated by the results of an initial screen. These include pentoxifylline (an inhibitor of cAMP phosphodiesterase; 57% inhibition), compound RO-20-1724 (47% inhibition; this is an average of three experiments), tamoxifen and nafoxidine (~65% inhibition by each), thioridazine and pimozide (anti-psychotic drugs; 60–70% inhibition), flunarizine (63% inhibition) and dithranol (an anti-psoriatic drug, and an inhibitor of leukotriene synthesis; 67% inhibition).

The $IC_{50}$ value for the inhibition of LPS-stimulated TNF production for compound RO-20-1724 appeared to lie between 1 nM and 10 nM in RAW cells. The $IC_{50}$ value for loperamide appears to lie below $1\times10^{-6}$ M since the degree of inhibition at that dose was equivalent to that achieved by the drug at 10 μM (highest dose tested).

3. Keratinocytes

Materials and Methods

Keratinocytes from neonatal foreskin were obtained from commercial sources (Cascade Biologics, Portland, Ore.; Clonetics Corporation, San Diego, Calif.) or primary cultures of keratinocytes were established from freshly procured neonatal human foreskin by overnight treatment in 0.25% trypsin at 4° C. and for 1 hour at 37° C., to enable removal of the stratum corneum, separation of epidermal from dermal tissue and isolation of basal/suprabasal cells.

The keratinocytes were maintained in culture in KGM growth medium supplemented with bovine pituitary extract from Clonetics (San Diego, Calif.) or M154 growth media supplemented with HKGS (Human Keratinocyte Growth Supplement) from Cascade Biologics (Portland, Ore.). Keratinocytes were passaged at 60–70% confluency by trypsinization and were subcultured at a minimum density of $0.25 \times 10^6$ cells per T-75 flask. Cells were maintained in culture for approximately 3 to 5 passages prior to being used in experiments or frozen down for storage. When frozen stocks were used in experiments, cells were thawed and plated at $0.5 \times 10^6$ cells per T75 and grown to approximately 60% to 70% confluency prior to splitting into experimental wells.

Experimental Conditions

Typically, keratinocytes were plated at a density of $1 \times 10^5$ cells per well with 0.5 mL growth medium in 24-well plates or at $5 \times 10^5$ cells per well with 2 mL of growth medium in 6-well plates, or $0.5 \times 10^5$ cell per well in 96-well plates with 0.25 mL media per well. Cells were subsequently incubated in hydrocortisone- and EGF-free HKGS in M154 medium for 24 to 48 hours prior to experimentation. Cultures were generally fully confluent at the start of the experiment and culture media was aspirated and replaced with 10 ng/mL TPA (Calbiochem-Novabiochem, La Jolla, Calif.) with or without test drug at 10 µM concentration in hydrocortisone- and EGF-free medium (for control, cells were incubated in fresh medium alone or with vehicle, and stimulus plus vehicle). Other stimulating agents used were retinoic acid (RA) and lipopolysaccharide (LPS) at 1 µM and 100 µg/ml, respectively. Dexamethasone, a well-known and efficacious anti-inflammatory corticosteroid drug, was included as a control drug in our in vitro screens. TPA stock solutions were prepared in tissue culture grade dimethyl sulfoxide (DMSO) at 1 mg/mL and stored in aliquots at –20° C. Drugs were prepared in a vehicle which allows for their complete dissolution, such as DMSO (e.g., amiloride) or ethanol (e.g., verapamil). Water-soluble drugs were dissolved in aqueous solutions such as RPMI or deionized $H_2O$. The final concentration of DMSO in the incubation medium was at or below 0.03% and that of ethanol was at or below 0.2%. Drugs were screened for their ability to alter stimulated TNF secretion and/or IL-1 production over a 24-hr or 48-hr incubation period. At the end of the experiment, the incubation medium was harvested from the cells and microcentrifuged to pellet down contaminating cells. The resulting cell-free "supernatant" was then tested for the presence of TNF by immunological means (ELISA). Nucleic acid extracts were prepared from the keratinocytes remaining in the wells and processed for isolation of RNA, followed by RT-PCR for detection of TNF-specific mRNA (PCR analysis of the housekeeping gene, β-actin, was used as a control to normalize for RNA content of sample). Treatment of cells with 10 nM or 50 nM TPA produced a maximal increase in TNF mRNA levels by 50% at the 2-hour time point which declined over the following 10 hours.

Results

In a drug screen, loperamide, (±)verapamil and amiloride, each at 10 µM concentration, were tested for possible effects on TPA-stimulated production of TNF in keratinocytes. These drugs were of particular interest in light of their effects on LPS stimulated cytokine production in RAW and THP-1 cells. Hexamethylamiloride, an analog of amiloride, was also included. Untreated cells produced very little TNF, but were stimulated to produce ~250 pg/mL TNF upon treatment with 10 ng/mL TPA. The response to TPA was inhibited by more than 55% by 10 µM dexamethasone. In this initial screen, loperamide was very effective at lowering TPA-stimulated levels of TNF in human keratinocytes, which is consistent with its effects on LPS-stimulated TNF production in THP-1 and RAW264.7 cells. On the other hand, the level of TNF in the supernatants of cells treated with TPA and 10 µM hexamethylamiloride were several fold higher than in cells treated with TPA alone, a result which is the reverse of what we observed for the LPS stimulated response in THP-1 and RAW264.7 cells.

With respect to IL-1 production by keratinocytes, untreated cells appeared to produce a significant amount of secreted and cell-associated IL-1α, with values in the range between 150 pg/mL and 200 pg/mL. However, incubation with TPA (10 ng/mL), retinoic acid (RA; 1 µM), or LPS (100 µg/mL) resulted in an enhancement of the levels of the cell-associated form for the incubation times chosen (24-, 36- and 48 hours). TPA was the most powerful inducer of the agents tested and its effects appeared to be most pronounced at 24 hrs, at which point the average amount of cell-associated IL-1α detected was ~1800 pg/mL (a 6-fold increase). The maximum effect of 1 µM RA was a ~3-fold increase at the 48 hr time point and that for 100 µg/mL LPS was ~4-fold at the 36-hr time point.

TABLE I

Inhibition of Stimulated* Cytokine Production in Human Cells by Various Drugs

| DRUG [10 µM] | TNF LEVEL % Control (LPS alone); Ave. ± S.D. | | |
| --- | --- | --- | --- |
| | HEK cells | RAW cells | THP-1 cells |
| (±)-Verapamil | 53 ± 11 | 36 ± 1 | 46 ± 9 |
| (−)-Verapamil | | | 53 ± 3 |
| (+)-Verapamil | | | 51 ± 2 |
| Nicardipine | | 59 ± 35 | 44 ± 1 |
| Nimodipine | 15 ± 3 | 37 ± 3 | 81 ± 4 |
| Nifedipine | 88 ± 40 | 79 ± 24 | 119 ± 13 |
| Bepridil | | 40 ± 4 | 77 ± 9 |
| Diltiazem | | 47 ± 1 | 86 ± 16 |
| Isradipine | 60 ± 7 | 34 ± 0.1 | 77 ± 8 |
| RO 20-1724 | | 47 ± 23 | 45 ± 34 |
| Loperamide | | 62 ± 32 | 42 ± 22 |
| Amiloride | ≧100 | 75 ± 25 | 56 ± 15 |
| Furosemide | | 49 ± 4 | |
| Diphenoxylate | 68 ± 10 | | |
| Thalidomide | ≧100 | 67 ± 37 | 78 ± 9 |
| Terbutaline | 36 ± 8 | 33 ± 9 | 12 ± 4 |
| Arterenol | 47 ± 10 | 38 ± 4 | 1 ± 0.2 |
| Pentoxifylline | | 43 ± 2 | ≧100 |
| Spironolactone | | | 54 ± 8 |
| Dexamethasone | 48 ± 12 | 39 ± 27 | 33 ± 14 |
| Rec 15/2375 | | 33 ± 1 | 57 ± 15 |

*For human epidermal keratinocytes (HEK), stimulation of TNF production was provided by TPA at a dose of 10 ng/mL. For THP-1 cells, stimulation was provided by an LPS dose of 1 µg/mL. For RAW cells, stimulation was provided by LPS at 10 ng/mL.

F. Evaluation and Diagnosis

The methods described herein will find use in the treatment of a variety of skin disorders having an inflammatory and/or immunological component. In order to employ the optimal therapeutic method, the skin disorder should first be properly diagnosed. In addition, subsequent to the application of the methods described herein to the affected skin, an evaluation of the affected skin must be made in order to determine the efficacy of the treatment.

Generally, the evaluation and diagnosis of a skin disorder is performed by compiling the patient's description of their symptoms, i.e., the patient's sensations related to the condition, such as pain or itching. The care giver also compiles their observations of the patient's signs based on the data obtained by the care giver's examination of the patient, e.g., observations of redness, swelling, or elevated temperature associated with the disorder. Usually such observations will be visual, with the care giver assimilating the data supplied by the patient and their own observations in an effort to recognize a pattern which identifies the disorder.

Many skin disorders can be diagnosed by physical examination alone. The patient will typically undress and undergo a complete examination as some signs may not be visible to the patient on self-examination. The oral mucosa, anogenital area, scalp, and nails are especially relevant areas of examination. A biopsy of the may be required for more detailed information of the affected tissue, especially if the condition is chronic. If a fungal infection is suspected, a scraping or culture may be taken for evaluation. The care giver will pay particular attention to certain signs and symptoms which identify especially serious conditions such as cancer or AIDS. The signs and symptoms for skin disorders are well-known and have been complied in such references as THE MERCK MANUAL, 16th Ed. (Merck & Co., Inc. 1992), which is incorporated herein by reference.

Typically, the parameters which will be assessed before and after treatment include the size of the affected area, the degree of erythema, edema, and/or ulceration, the relative height or thickness of any lesions, and the amount of itching, pain, or other evaluations of patient discomfort. A further parameter for evaluation is TEWL. According to some aspects of this invention, a treatment regimen can be said to be efficacious if after treatment, the TEWL of the affected area is less than or equal to 20% of normal or healthy skin, i.e., those areas not affected by the condition. More definitive assessments of both the diagnosis of a disease and the efficacy of a given treatment protocol can be made using punch biopsy techniques that are known in the art.

More specifically, one embodiment of this invention is drawn to the treatment of psoriasis with iontophoresis, optionally in combination with pharmacological intervention and/or occlusion. Psoriasis is characterized by symmetrical erythematous, scaling plaques on the skin surface. The involved (lesional) skin is thickened and may be mildly pruritic. It is upon these physical parameters and symptoms that a diagnosis of psoriasis is typically made. An efficacious treatment for psoriasis would involve the reduction of the scaling, redness, and itching, as well as a thinning of the plaques. As typically, erythema is the last parameter to resolve, it may still persist at the termination of the treatment period. Clinically most investigators use the PASI score (psoriasis area and severity index) which takes into account the total body surface area of lesional skin, as well as the degree of erythema, scaling, and thickness to evaluate the efficacy of any given therapeutic protocol. See, e.g., Fredriksson et al. (1978) *Dermatoly.* 157:238–244 which is incorporated herein by reference.

A further embodiment of this invention provides for methods for treating wounds, and particularly, decubitus ulcers, Decubitus ulcers represent impaired blood supply to the skin. There is ischemic necrosis of the epidermis with underlying acute and chronic inflammation. The edge of the ulceration is tender, erythematous, and may become secondarily infected by bacteria. A diagnosis for decubitus ulcers would be based upon these physical manifestations of the disorder. Upon treatment, there is the appearance of granulation tissue, followed by re-epithelialzation of the ulcer surface.

Another embodiment of this invention is drawn to methods for treating skin cancers and particularly, basal cell carcinoma. Basel cell carcinomas clinically appear as pearly papules with telangiectasis. They can be both small papules or larger nodules with or without erythema and ulceration. Clinical parameters to be assessed before and after treatment include: change in the size of the lesion, degree of erythema/ ulceration, and relative thickness or height of elevated lesions. With successful therapy, there may be slight residual fibrosis, erythema and chronic inflammation. A more definitive assessment can be made by taking a small (about 2 mm) punch biopsy before and after the treatment. See Albright (1982) *J. Amer. Acad. Dermatol.* 7:143–171, the full disclosure of which is incorporated herein by reference.

References useful in the diagnosis of skin disorders and evaluation of therapeutic treatments for skin disorders include HARRISON'S PRINCIPLES OF INTERNAL MEDICINE, Braunwald et al. (eds.), 11th Ed., McGraw-Hill Book Company (1987), especially pages 226–262; ROBBINS PATHOLOGIC BASIS OF DISEASE, Cotran et al. (eds.), 4th Ed., W. B. Saunders Company (1989), especially pages 1277–1315; TEXTBOOK OF DERMATOLOGY, Champion et al. (eds.) supra; and SKIN PHARMACOLOGY AND TOXICOLOGY: RECENT ADVANCES, Galli et al. (eds.), NATO ASI Series, Plenum Press, (1990), the full disclosures of which are incorporated herein by reference.

G. The Treatment of Skin Inflammatory Diseases with a Solution of Ions using Iontophoresis This therapeutic regimen is applicable to skin conditions or diseases having an inflammatory and/or immunoallergic component. In addition, these methods may find use for acute relief from flare-ups and in conjunction with other drug therapies.

A device capable of providing a constant operating current range between 0.01 and 10 milliamperes (mA) with a power source requirement up to 100 volts is connected to two electrodes. The anode and cathode will be formed from materials suitable for administering the desired current and compatible with the pharmacological agent. Typically, a silver-silver chloride system or platinum electrodes will be used. These electrodes are placed in a pliable reservoir (typically, 2–10 milliliters (ml)) having a semipermeable membrane for placement next to the skin.

The donor compartment is filled with an ion solution. The return compartment is filled with a conventional conductive gel, electrolyte-containing gel or gel matrix or absorbent material, as are commonly used in electrotransport. Typically, this ion solution will comprise an aqueous solution of the chloride or other salt of potassium, magnesium, or calcium in the concentration range of from about 0.1 to 120 millimolar (mM). Solutions of $Ca^{++}$ are preferably 0.1–20 mM, more preferably 1–5 mM. Solutions of $Mg^{++}$ are preferably 0.1–20 mM, more preferably 1–5 mM. Solutions of $K^+$ are preferably 5–90 mM, more preferably 60–80 mM.

The ion solution is placed into the donor reservoir which is then placed over the affected area. A current of from about 0.01 to about 10 mA, preferably from about 0.05 to about 8 mA, more preferably from about 0.1 to about 2 mA, and most preferably from about 0.1 to about 0.5 mA, is applied from about 5 to about 240 minutes, preferably, from about 5 to about 120 minutes, and most preferably, from about 20 to about 40 minutes. The area is then occluded with a water impermeable dressing. The therapy is repeated as necessary.

After one day of therapy, the TEWL of the skin over the affected area is measured using a standard electrolytic device. If the TEWL is less than or equal to 20% of normal or healthy skin, i.e., those areas not affected by the condition, then the ionic solution is combined with a combination of glycerin/oleyl alcohol, or other stratum corneum perturbants, so as to not change the final ion concentration of the solution. Preferred combinations of glycerin and oleyl alcohol in percent by weight will include 0.1–15 percent glycerin and 0.05–10 percent oleyl alcohol. More preferably the combinations will include 0.25–2 percent glycerin and 0.1–5 percent oleyl alcohol.

The solution containing the ions and the stratum corneum perturbant is then applied topically to the affected area 5 to 10 minutes prior to administration of the iontophoretic device. The iontophoretic treatment described above is then repeated. This combination of topical and iontophoretic treatments can be repeated as necessary.

H. The Reduction of Irritation in Conjunction with Topical Drug Administration The above procedure is followed except that an aqueous solution or gel of sodium phosphate (pH 4–9) is also prepared at a concentration from about 10 to about 200 mM, preferably from about 30 to about 150 mM, and more preferably, from about 60 to about 80 mM. This phosphate solution is placed in the donor reservoir. The return electrode is filled with a conductive gel, electrolyte-containing gel or gel matrix or absorbent material, as are commonly used in electrotransport. The donor electrode containing the phosphate solution is situated over the affected area. A current, as described in examples above, is applied for about 5 to about 10 minutes during the interludes between treatment periods wherein the affected area is treated with a drug delivered topically or via a transdermal delivery device. The affected area is not occluded. It is possible to repeat this therapy up to 10 times in a 24 hour period.

I. Treatment of Superficial Wounds and External Cancers

As described in Example B above, a device capable of providing a constant current between about 0.01 and 20 mA is connected to two silver-silver chloride electrodes. An aqueous solution of sodium chloride, typically with a concentration from about 1 to about 200 mM, preferably from about 5 to about 135 mM, and more preferably from about 20 to about 80 mM, is placed in the donor compartment. The electrode is then located on the affected area. The return electrode is filled with a conductive gel. A current of about 0.1 to about 20 mA, preferably from about 0.5 to about 10 mA, more preferably from about 1 to about 5 mA, is applied from about 5 to about 120 minutes, preferably from about 5 to about 60 minutes, and more preferably from about 10 to about 30 minutes. The treatment may be repeated as necessary.

J. Topical Formulations

Therapeutic formulations containing the compounds described above and that are applicable to skin conditions or diseases having an inflammatory and/or immunoallergic component are included in the present invention. Such formulations are useful for relief from chronic and acute conditions, flare-ups and in conjunction with other drug therapies. As an example, a cream, ointment and gel formulations including loperamide are described below. Formulations including one or more of the compounds described herein may be made by analogy to the following examples.

Cream Containing Loperamide

A cream containing formulation of loperamide was prepared containing stearic acid (15.0%), cetyl alcohol (1.0%), white petroleum (3.0%), polyoxy 40 stearate (4.0%), methyl paraben (0.025%), propyl paraben (0.015%), bumetanide (2.0%), propylene glycol (9.5%), sorbitol (7.5%) with water making up the remainder.

Loperamide-Containing Ointment

A loperamide ointment was prepared containing, in percent by weight, Miglyol™ 840-B Gel (10.0%), Eutanol G-Octyldodecanol (17.0%), Cril 6-Glyceryl isostearate (3.0%), hard paraffin wax (3.0%), zinc stearate (1.0%), Amphisol K (0.5%), Germaben II (1.0%), magnesium sulfate (0.2%), urea (10.0%), loperamide (2.0%) with water making up the remainder.

Loperamide-Containing Gel

A loperamide gel was prepared containing, in percent by weight, loperamide (2.0%), Carbopol 940™ (1.5%), triethanolamine (1.5%) with water making up the remainder.

K. Topical Skin Delivery of Verapamil Formulations

Various verapamil formulations (at 80% verapamil saturation) were prepared (see Table) and topical skin delivery (i.e., verapamil delivered to the epidermis and dermis) from these formulations to excised human skin was accessed using flow-through diffusion apparatus. Verapamil formulation (50 $\mu$l/cm$^2$) was applied topically three times during the 24-hour delivery experiment. Prior to each application, residual formulation was removed with a cotton swab. At the end of the study, skin was removed from the diffusion cell, excess formulation was wiped off the surface, the stratum corneum was stripped off the skin by tape, and the remaining epidermis and dermis was weighed. Total verapamil delivered to the epidermis and dermis was extracted by ethanol and was quantitated by high-performance liquid chromatography. The concentration of verapamil in the skin was calculated based on the amount of verapamil extracted and the total weight of the sample. From the data shown in the following Table, the gel formulation delivers the highest quantity of verapamil to the human skin.

| No. # | Formulation | VRP (conc.) in 80% Sat'd mg/mL | VRP/ Skin Mean $\mu$M |
|---|---|---|---|
| | Summary of Skin Delivery Profile from Various Verapamil Formulations | | |
| | Solution | | |
| 1 | GP/water (30/70) | 59.7 | 856.09 |
| 2 | ETOH/water (50/50) | 375.5 | 254.86 |
| 3 | Glycerin/water (50/50) | 15.9 | 515.48 |
| 4 | PEG 400/water (50/50) | 89.7 | 1419.46 |
| 5 | ETOH/water/oleic acid (50/49.75/0.25) | 307.6 | 2081.73 |

Summary of Skin Delivery Profile from Various Verapamil Formulations

| No. # | Formulation | VRP (conc.) in 80% Sat'd mg/mL | VRP/ Skin Mean µM |
|---|---|---|---|
| 6 | Glycerin/water/oleic acid (50/49.75/0.25) Gel | 15.4 | 691.74 |
| 7 | ETOH/PEG 300/PG/natrasal/ carbopol/water (20/10/20/0.4/1/48.6) Ointment | 259.4 | 3771.47 |
| 8 | White petrolatum/light mineral oil (55/45) | 100.0 | 955.26 |

L. Prevention or Reduction of Transdermal Drug Delivery System-Induced Irritation It has been well documented that transdermal therapeutic systems cause 15–20% local irritation, and occasionally, contact hypersensitivity reactions. For example, moderate irritation and allergic contact dermatitis are known to develop during 21-day consecutive usage of clonidine transdermal patches in man (Catapres-TTS®) (Maibach HI, *Contact Dermatitis* 12:192–195 (1985)).

To prevent or to reduce these local adverse reactions due to the use of transdermal patches, a TNF-inhibitor formulation including agents such as diuretics (e.g., furosemide, spironolactone), antidiarrheal agents (e.g., loperamide, diphenoxylate) or calcium channel blockers (e.g., isradipine, nicardipine, verapamil, etc.) or ion modulating agents ($La^{+3}$) is formulated in topical gel dosage form (Table). This gel is administered in conjunction with a transdermal patch such as a clonidine transdermal patch (Catapres-TTS®). Skin is pretreated with the anti-inflammatory formulation at a 50–200 µl per $cm^2$ dose for three times over the day prior to the application of the patch.

The anti-inflammatory formulation can also be applied about two hours prior to the application of the patch at the same skin site as well as following the removal of the patch. Local adverse skin reactions, i.e., relative irritancy potential (21-day cumulative irritancy assay) and allergic contact dermatitis potential (Draize repeat insult patch test assay) of the clonidine patches with and without co-administration of an anti-inflammatory formulation is compared. Various combinations of pre-, co- and/or post-treatment regimen are tested to achieve the best result with respect to minimize these adverse skin reactions.

M. The Use of Specific Isomers of Calcium Channel Blockers to Modulate TNF-Mediated Conditions

1. Inhibition of TNF Release in Stimulated Cells using (+)-Verapamil

This example illustrates the ability of (+)-verapamil to inhibit TNF release in stimulated cells. A comparison of (+)-verapamil with a number of anti-inflammatory agents is provided in Table I. A control (dexamethasone) was included.

As the results in Table I demonstrate, surprisingly, most calcium channel blockers (i.e., (±), (−) and (+)-verapamil, nicardipine, isradipine and Rec 15/2375 are effective in inhibiting the release of TNF in stimulated cells, and (+)-verapamil is much more effective than thalidomide or pentoxifylline.

2. Verapamil for the Prevention of Skin Inflammation in Mice

This example illustrates the ability of (±)-verapamil to prevent skin inflammation induced by 2% sodium lauryl sulfate (SLS) in mice.

Flanks of mice were exposed to either 150 µL of 2% SLS or the same concentration of SLS containing near saturated levels of verapamil for 24 hours under occlusion in a Hilltop chamber. Following the 24 hour exposure, the Hilltop chambers were removed and, after 18 hours, skin thickness readings were taken. The results indicate that within minutes of removing the 2% SLS chambers, a discolored wound was detected on the mice. For the flanks exposed to SLS and verapamil, no effects of SLS irritation were observed. The skin thickness measurements for the treated flanks as well as for untreated skin are provided in the table below.

TABLE
Verapamil Prevention of Skin Inflammation

| Treatment | Visual Observation | Skin Thickness (mm, n = 4) |
|---|---|---|
| 2% SLS | Wound | 1.23 ± 0.11 |
| 2% SLS/Verapamil | Normal | 0.65 ± 0.09 |
| Untreated Skin | Normal | 0.59 ± 0.08 |

As the results in the table indicate, edema developed in the SLS-treated sites but was absent in the SLS/verapamil-treated sites. Thus, verapamil was effective in preventing the development of skin inflammatory responses in mice.

3. Use of Verapamil for the Treatment of Skin Inflammation in Humans

This example illustrates the use of (±)-verapamil for the treatment of skin inflammation models in humans.

Human skin inflammation was elicited by either 2% sodium laurel sulfate in normal volunteers (irritant contact dermatitis) or by 5% nickel sulfate in nickel-sensitive individuals (allergic contact dermatitis) using a 24 hour patch test. Following the elicitation, either topical verapamil formulation or a placebo formulation was applied three times daily for two consecutive days on two respective sites. At the end of the two-day topical treatment, the degree of skin inflammation (i.e., erythema, edema and blister formation was assessed by a trained dermatologist. Skin biopsies were taken from the placebo and the active sites and analyzed for skin thickness and TNF levels using immunohistochemical techniques.

Figure 5:
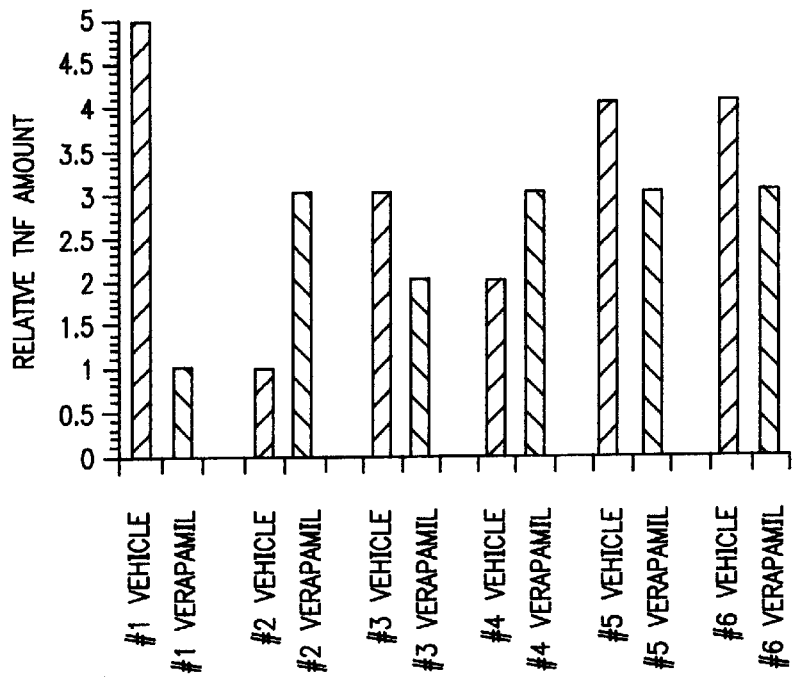
FIG. 5 illustrates the ability of verapamil to suppress TNF expression in a skin inflammation model in man.
Figure 6:
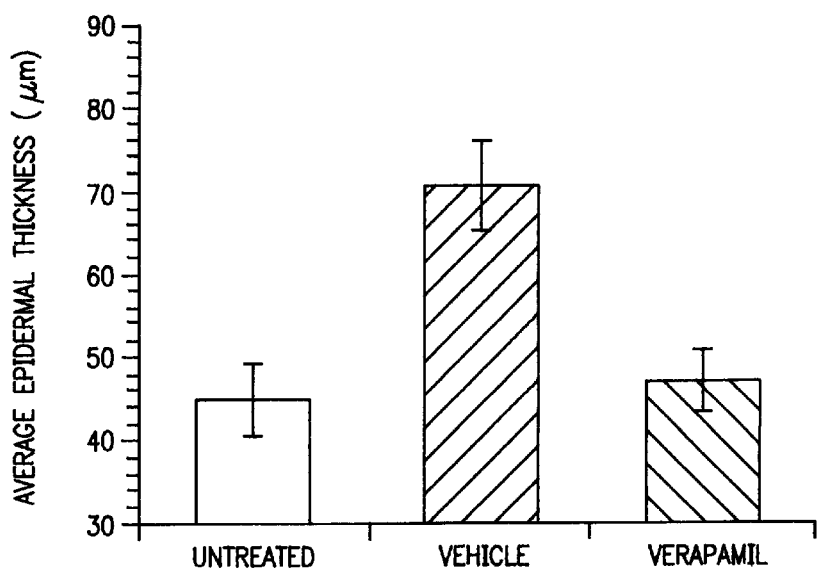
FIG. 6 illustrates the ability of verapamil to suppress epidermal swelling in a skin inflammation model in man.

The results of the biopsy analysis indicated that there is an increase in the TNF protein level and skin thickness of biopsies derived from the placebo sites in 50% of the patients and that TNF protein is mainly localized in the basel layer of the epidermis. In comparison with the placebo sites, 4 out of 6 patients (2 out of 3 for each test) treated with verapamil showed less TNF in the skin biopsies (see FIG. 5). Further, skin thickness was less in 4 out of 6 patients on verapamil-treated sites than that of the placebo sites (see FIG. 6). Thus, verapamil was found to suppress irritant and allergen-induced increases in TNF production and skin thickness in humans.

Additionally, dermatitis was also found to resolve faster on verapamil treated sites in 2 out of 3 patients challenged with 2% sodium laurel sulfate. In summary, verapamil suppresses pro-inflammatory cytokine TNF production, mitigates hyperproliferative responses and demonstrates anti-inflammatory properties in a skin inflammation model in man.

4. Use of (+)-verapamil for the Treatment of Atopic Dermatitis

An adult patient having severe cutaneous manifestations of atopic dermatitis is selected for therapy. The patient is evaluated with screening tests including vital signs with special attention to blood pressure and any tendency to orthostasis, a complete blood count, a urine analysis, and peripheral blood tests for blood urea nitrogen, sodium, potassium, calcium, and creatinine. A chest x-ray (CXR) and electrocardiogram (EKG) are also performed. The practitioner makes notations of the severity and extent of the pruritus, erythema and induration and performs biopsies if indicated. Additionally, lichenification and scaling/dryness are also rated.

The patient is treated with (+)-verapamil topically three times daily until a benefit is achieved. (+)-Verapamil is supplied in a semi-solid topical formulation, either cream, ointment or a spray. Once a benefit has been demonstrated, the topical application is administered less frequently, as needed, to maintain the benefit. Further, the (+)-verapamil formulation can also be used as adjuvant or maintenance therapy following a full-course of other treatments.

5. The use of (+)-Verapamil in a Topical Formulation to Treat Psoriasis

An adult patient having severe cutaneous manifestations of psoriasis is selected for therapy. The patient is evaluated with screening tests including vital signs with special attention to blood pressure and any tendency to orthostasis, a complete blood count, a urine analysis, and peripheral blood tests for blood urea nitrogen, sodium, potassium, calcium, and creatinine. A chest x-ray (CXR) and electrocardiogram (EKG) are also performed. The practitioner makes notations of the severity and extent of the dermal psoriatic plaques and performs biopsies if indicated.

The patient is treated with topical (+)-verapamil in a topical vehicle applied directly to the psoriatic skin areas three to four times a day until a therapeutic benefit is achieved. Thereafter, the formulation is applied less frequently, as needed, to maintain the benefit. Further, the (+)-verapamil formulation can also be used as adjuvant or maintenance therapy following a full-course of other anti-psoriasis treatments.

6. The Use of (+)-Verapamil for the Treatment and Prevention of UV-induced Inflammation An adult patient suffering from severe UV-induced inflammation is selected for therapy. The patient is treated with topical (+)-verapamil in a cream vehicle of concentration 1% (weight/volume) applied directly to the afflicted skin areas twice a day until a therapeutic benefit is achieved. Thereafter, the cream is applied less frequently, as needed, to maintain the benefit and to provide prevention for subsequent exposure to UV irradiation.

7. The Use of (+)-Verapamil in Combination with Retin-A for the Treatment of Dermatitis An adult patient suffering from severe cutaneous manifestations of dermatitis is selected for therapy. The patient is evaluated according to the procedures described above. The patient is treated topically with a preparation of 0.1% (weight/volume) all-trans retinoic acid (Retin-A) and 2% (weight/volume) (+)-verapamil in a cream vehicle. The preparation is applied directly to the afflicted skin areas twice a day. Applications are continued until a therapeutic benefit is achieved. Thereafter, the cream is applied less frequently, as needed, to maintain the benefit. The combination formulation of Retin-A and (+)-verapamil can also be used as adjuvant or maintenance therapy following a full-course of other anti-dermatitis treatments.

8. The Use of (+)-Verapamil to Treat Rheumatoid Arthritis, a Systemic Inflammatory Condition An adult patient having rheumatoid arthritis involving multiple small joints, several large joints, and intermittent debilitating systemic symptoms is selected for treatment. Screening tests as in Example 3 are performed. At the practitioner's discretion, the patient's current medications can be continued, and oral (+)-verapamil is added to the current regimen. The (+)-verapamil is started at 20 mg twice a day. If tolerated, the dosage is increased in increments of 20 mg daily until a therapeutic benefit is achieved.

If needed, (+)-verapamil is injected directly into joints which are especially problematic. An aqueous concentration of 10 mg/mL is used, and each joint treated is injected with 20–40 mg of (+)-verapamil. The injection is repeated weekly if needed. Suitable formulations of (+)-verapamil can also be used as adjuvant or maintenance therapy associated with other forms of rheumatoid arthritis treatments.

9. The Use of (+)-Verapamil as a Second Active Agent in a Transdermal Patch

A patient is selected for treatment with a transdermal patch including a first active agent which is not verapamil. Because the patient has, in the past, experienced unacceptable local irritation from a transdermal patch, (+)-verapamil is incorporated into the patch as a second active agent for its anti-inflammatory effects. The concentration of (+)-verapamil in the patch is about 0.5% by weight. The patch is applied according to the requirements of the first active agent. Because of the addition of (+)-verapamil to the patch, the patient does not experience unacceptable local skin irritation at the site of application of the patch.

10. The Use of (+)-Verapamil to Treat Inflammatory Bowel Diseases

Patients having a definite diagnosis of Crohn's disease or ulcerative colitis (based on radiological and histologic findings) are further examined via colonoscopy and barium imaging. (+)-Verapamil is administered twice or three times daily, either orally, or other means of delivery until a therapeutic benefit is achieved. Disease activity is assessed on the basis of reported symptoms, changes in weight, and other laboratory testings. Further, (+)-verapamil can be used as adjuvant or maintenance therapy of corticosteroid and other treatment regimens.

11. The Use of (+)-Verapamil to Treat Cachexia (Wasting Syndrome) Associated with Cancer or AIDS Patients Patients having AIDS and suffering from the weight loss associated with AIDS are screened using complete blood cell counts (CBCs), TNF mRNA, CD4 counts, chemistries (fasting triglycerides, creatinine, bilirubin, transaminases, and CPK), neopterin, $\beta_2$-microglobulin, and quantitative HIV cultures.

The patients are administered (+)-verapamil in a controlled-release formulation (i.e., OROS™) three times daily with meals. Treatment is continued until no further benefit is observed.

All publications, patents and patent applications mentioned in this specification are herein incorporated by reference into the specification to the same extent as if each individual publication, patent or patent application was specifically and individually indicated to be incorporated herein by reference.

The above description is illustrative and not restrictive. Many variations of the invention will become apparent to those of skill in the art upon review of this disclosure. Merely by way of example a variety of formulations, dosages, and protocols for treatment may be used without departing from the scope of the invention. The scope of the invention should, therefore, be determined not with reference to the above description, but instead should be determined with reference to the appended claims along with their full scope of equivalents.

What is claimed is:

1. A composition formulated for topical administration, comprising loperamide in a non-aqueous-based vehicle suitable for topical application to the skin.

2. The composition of claim 1, wherein loperamide is present in an anti-inflammatory effective amount.

3. A composition formulated for topical administration, comprising loperamide in a vehicle suitable for topical application to the skin, wherein the composition is formulated as a gel.

4. A composition formulated for topical administration, comprising loperamide in a vehicle suitable for topical application to the skin, wherein the composition is formulated as a lotion.

5. A composition formulated for topical administration, comprising loperamide in a vehicle suitable for topical application to the skin, wherein the composition is formulated as a cream.

* * * * *

UNITED STATES PATENT AND TRADEMARK OFFICE
CERTIFICATE OF CORRECTION

PATENT NO. : 5,962,477
DATED : Oct. 5, 1999
INVENTOR(S) : Mak

It is certified that error appears in the above-identified patent and that said Letters Patent is hereby corrected as shown below:

IN THE TITLE PAGE:

In item [75] entitled Inventor, please replace "Vivian" with —Vivien—;

Signed and Sealed this

Twenty-eighth Day of March, 2000

Attest:

Q. TODD DICKINSON

Attesting Officer

Commissioner of Patents and Trademarks